(12) United States Patent
Kufe et al.

(10) Patent No.: US 8,952,054 B2
(45) Date of Patent: Feb. 10, 2015

(54) SMALL MOLECULE INHIBITORS OF MUC1 AND METHODS OF IDENTIFYING THE SAME

(75) Inventors: Donald W. Kufe, Wellesley, MA (US); Surender Kharbanda, Natick, MA (US)

(73) Assignees: Dana-Farber Cancer Institute, Inc., Boston, MA (US); Genus Oncology, LLC, Chicago, IL (US)

( * ) Notice: Subject to any disclaimer, the term of this patent is extended or adjusted under 35 U.S.C. 154(b) by 410 days.

(21) Appl. No.: 13/045,033

(22) Filed: Mar. 10, 2011

(65) Prior Publication Data

US 2011/0251246 A1    Oct. 13, 2011

Related U.S. Application Data

(60) Provisional application No. 61/313,996, filed on Mar. 15, 2010.

(51) Int. Cl.

| | | |
|---|---|---|
| A61K 31/35 | (2006.01) | |
| C07K 5/103 | (2006.01) | |
| C07D 311/02 | (2006.01) | |
| A61K 31/353 | (2006.01) | |
| C07K 5/083 | (2006.01) | |
| C07K 7/06 | (2006.01) | |
| G01N 33/50 | (2006.01) | |
| G01N 33/574 | (2006.01) | |
| G01N 33/68 | (2006.01) | |

(52) U.S. Cl.
CPC ............ *C07K 5/1013* (2013.01); *C07D 311/02* (2013.01); *A61K 31/35* (2013.01); *A61K 31/353* (2013.01); *C07K 5/081* (2013.01); *C07K 7/06* (2013.01); *G01N 33/5011* (2013.01); *G01N 33/57496* (2013.01); *G01N 33/6872* (2013.01); *G01N 2333/4725* (2013.01); *G01N 2500/04* (2013.01)
USPC ........... 514/453; 549/356; 549/381; 549/416; 549/420

(58) Field of Classification Search
None
See application file for complete search history.

(56) References Cited

U.S. PATENT DOCUMENTS

2010/0069480 A1* 3/2010 Cohen .......................... 514/456

FOREIGN PATENT DOCUMENTS

| WO | WO 2010/012037 | 2/2010 |
|---|---|---|
| WO | WO 2010/045586 | 4/2010 |

OTHER PUBLICATIONS

Liang, Yu-Chih et al; "Supression of inducible cyclooxygenase and inducible nitric oxide synthase by apigenin and related flavonoids in mouse macrophages." Carcinogenesis (1999) 20(10) p. 1945-1952.*
Lloyd, Kenneth O. et al; "Comparison of o-linked carbohydrate chains in MUC-1 mucin from normal breast epithelial cell lines and breast cancer carcinoma cell lines." J. Biol. Chem. (1996) 271(52) p. 33325-33334.*
Patel, Deendayal et al; "Apigenin and cancer chemoprevention: progress, potential, and promise." Int. J. Oncol. (2007) 30 p. 233-245.*
Liang, Yu Chih et al; "Suppression of inducible cyclooxygenase and inducible nitric oxide synthase by apigenin and related flavonoids in mouse macrophages." Carcinogenesis (1999) 20(10) p. 1945-1952.*
Kim, Hyun Pyo et al; "Anti-inflammatory plant flavonoids and cellular action mechamism." J. Pharmacol. Sci. (2004) 96 p. 229-245.*
Pierce biotechnology biotin labeling reagents web page (http://www.piercenet.com/cat/biotin-labeling-reagents-proteins), downloaded Mar. 7, 2014.*
Online definition of reduction (http://www.chemteam.info/Redox/Meaning-of-Redox.html) downloaded Mar. 7, 2014.*
Nucleophylic acyl substitutions class notes (http://www.vanderbilt.edu/AnS/Chemistry/Rizzo/Chem220b/Ch20.pdf), downloaded Mar. 10, 2014.*
Kato, Kosuke et al; "PHoshpinositide 3-kinase is activated by muc1 but not responsible for muc1—induced suppression of toll-like receptor 5 signaling." Am. J. Physiol. Lung. Cell. Mol. Physiol. (2007) 293 p. L686-L692.*
Patel, Deendayal et al; "Apigenin and cancer chemoprevention: progress, potential and promise (review)." Int. J. Oncol. (2007) 30 p. 233-245.*
De Bolòs, Carme et al; "Muc6 expression in breast tissues and cultured cells: abnormal expression in tumors and regulation by steroid hormones." Int. J. Cancer (1998) 77 p. 193-199.*
Liang, Yu-Chih et al; "Suprression of inducible cyclooxygenase and inducible nitric oxice synthase by apigenin and related flavonoids in mouse macrophages." Carcinogenesis (1999) 20(10) p. 1945-1952.*
Kim, Hyun Pyo et al; "Anti-inflammatory plant flavonoids and cellular action mechanisms." J. Pharmacol. Sci. (2004) 96 p. 229-245.*
USPTO Subject Matter Eligibility Guidance Update, "Myriad-Mayo Guidance", publicly available on Mar. 4, 2014.*
"Apigenin," Wikipedia, available online at http://en.eikipedia.org/wiki/Apigenin, accessed on Mar. 2, 2010.
Ahmad et al., "Combining the FLT3 inhibitor PKC412 and the triterpenoid CDDO-Me synergistically induces apoptosis in acute myeloid leukemia with the internal tandem duplication mutation.," *Mol Cancer Res.*, 8(7):986-93, 2010.
Ahmad et al., "MUC1-C oncoprotein functions as a direct activator of the nuclear factor-kappaB p65 transcription factor," *Cancer Res.*, 69(17):7013-7021, 2009.

(Continued)

*Primary Examiner* — James H Alstrum Acevedo
*Assistant Examiner* — Fred Reynolds
(74) *Attorney, Agent, or Firm* — Parker Highlander PLLC

(57) ABSTRACT

The invention provides methods for the identification of small molecules that inhibit MUC1 oligomerization, and the functions flowing therefrom. In addition, small molecules that prevent MUC1 oligomerization are disclosed. Identified molecules will find use in treating a variety of MUC1-related inflammatory conditions, including MUC1-related cancers.

22 Claims, 32 Drawing Sheets

(56) References Cited

OTHER PUBLICATIONS

Ahmad et al., "MUC1-C oncoprotein promotes STAT3 activation in an autoinductive regulatory loop", *Sci Signal.*, 4(160): ra9, 2011.

Huang et al., "MUC1-C Oncoprotein Interacts Directly with ATM and Promotes the DNA Damage Response to Ionizing Radiation," *Genes Cancer*, 1(3):239-250, 2010.

Joshi et al., "MUC1 oncoprotein is a druggable target in human prostate cancer cells," *Mol Cancer Ther.*, 8(11):3056-65, 2009.

Kufe, "Mucins in cancer: function, prognosis and therapy," *Nature Rev. Cancer*, 9:874-885, 2009.

Leng et al., "Nuclear Import of the MUC1-C Oncoprotein Is Mediated by Nucleoporin Nup62," *J. Biol. Chem.*, 282:19321-19330, 2007.

Raina et al., "Dependence on the MUC1-C Oncoprotein in Non-Small Cell Lung Cancer Cells," *Mol Cancer Ther.*, 10(5):806-16, 2011.

Raina et al., "Direct targeting of the mucin 1 oncoprotein blocks survival and tumorigenicity of human breast carcinoma cells," *Cancer Res.*, 69(12):5133-5141, 2009.

Reiners Jr. et al., "PD98059 is an equipotent antagonist of the Aryl Hydrocarbon receptor and inhibitor of mitogen-activated protein kinase kinase," *Molecular Pharmacology*, 53:438-445, 1998.

Yin et al., "MUC1 oncoprotein promotes autophagy in a survival response to glucose deprivation," *Int J Oncol.*, 34(6):1691-9, 2009.

Yin et al., "MUC1-C oncoprotein suppresses reactive oxygen species-induced terminal differentiation of acute myelogenous leukemia cells," *Blood*, 117(18):4863-70, 2011.

Yin et al., "Survival of human multiple myeloma cells is dependent on MUC1 C-terminal transmembrane subunit oncoprotein function," *Mol Pharmacol.*, 78(2):166-74, 2010.

Yin et al., "Terminal differentiation of chronic myelogenous leukemia cells is induced by targeting of the MUC1-C oncoprotein," *Cancer Biol Ther.*, 10(5):483-91, 2010.

Partial Search Report and Invitation to Pay Fees, issued in International Patent Application No. PCT/US2011/027970, mailed on Jul. 15, 2011.

Chu et al., "Induction of apoptosis by esculetin in human leukemia cells," *European Journal of Pharmacology*, 416(1, 2):25-32, 2001.

Chuang et al., "Coumarin Induces Cell Cycle Arrest and Apoptosis in Human Cervical Cancer HeLa Cells through a Mitochondria- and Caspase-3 Dependent Mechanism and NF-κB Down-regulation," *In Vivo*, 21(6):1003-1009, 2007.

Hamalainen et al., "Anti-inflammatory effects of flavonoids: genistein, kaempferol, quercetin and daidzein inhibit STAT-1 and NF-kappa B activations, whereas flavones, isorhamnetin, naringenin and pelargonidin inhibit only NF-kappa B activation along with their inhibitory effect on iNOS expression and NO production in," *Mediators of Inflammation*, Article ID 45673, 10 pages, 2007.

Hsieh et al., "Baicalein inhibits IL-1β- and TNF-α-induced inflammatory cytokine production from human mast cells via regulation of the NF-κB pathway," *Clinical and Molecular Allergy*, 5(1):p. 5, 2007.

International Search Report and Written Opinion, issued in International Patent Application No. PCT/US2011/027970, mailed Nov. 21, 2011.

Lin et al., "Luteolin, a flavonoid with potential for cancer prevention and therapy," *Current Cancer Drug Targets*, 8(7):634-646, 2008.

Moon et al., "Use of scopoletin to inhibit the production of inflammatory cytokines through inhibition of the IκB/NF-κB signal cascade in the human mast cell line HMC-1," *European Journal of Pharmacology*, 555(2-3):218-225, 2007.

Patel at al., "Apigenin and cancer chemoprevention: progress, potential and promise (review)," *International Journal of Oncology*, 30(1):233-245, 2007.

Ruela-De-Sousa et al., "Cytotoxicity of apigenin on leukemia cell lines: implications for prevention and therapy," *Cell Death and Disease*, 1:E19, 2010.

Wu et al., "Naturally occurring flavonoids attenuate high glucose-induced expression of proinflammatory cytokines in human monocytic THP-1 cells," *Molecular Nutrition and Food Research*, 53(8):984-995, 2009.

Zhou et al., "Mucin 1 C-Terminal subunit oncoprotein is a target for small-molecule inhibitors," *Molecular Pharmacology*, 79(5):886-893, 2011.

* cited by examiner

B.

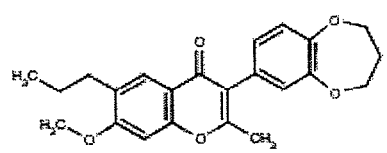
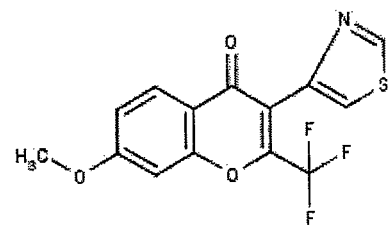
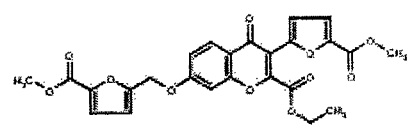
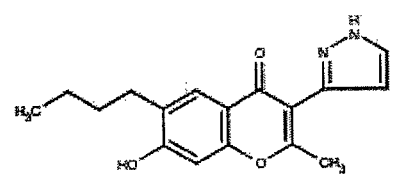
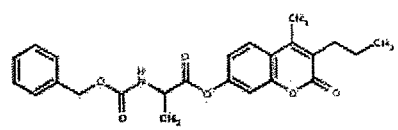
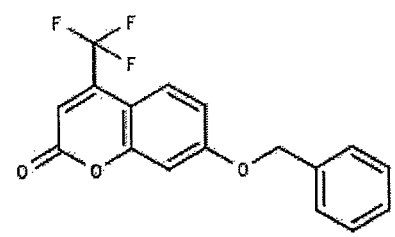
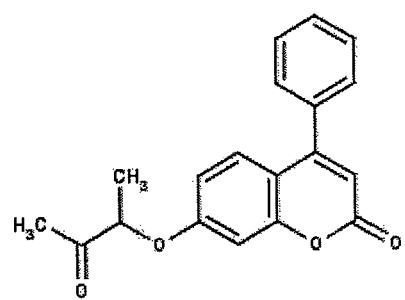
FIG. 10

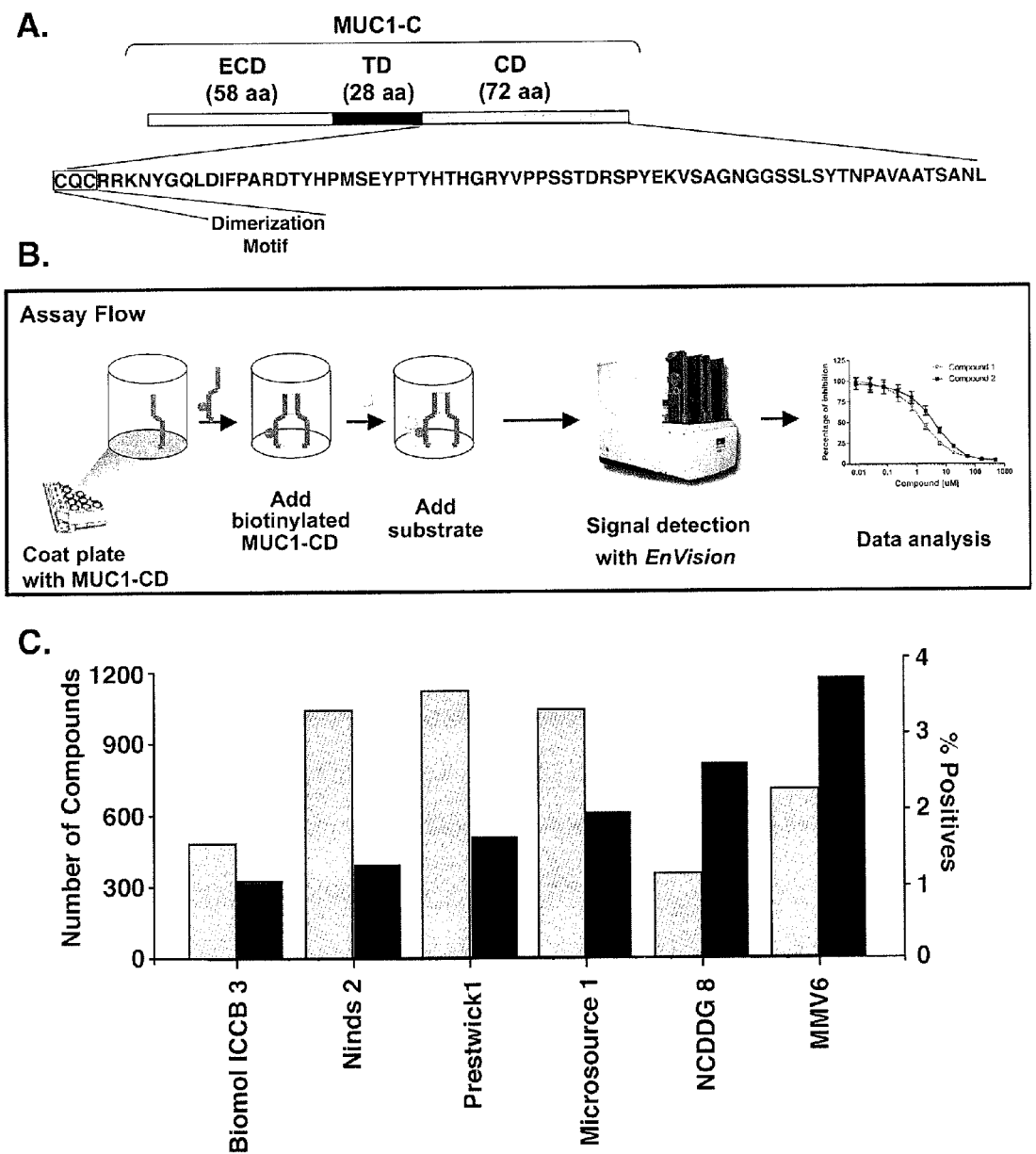
FIG. 11A–C

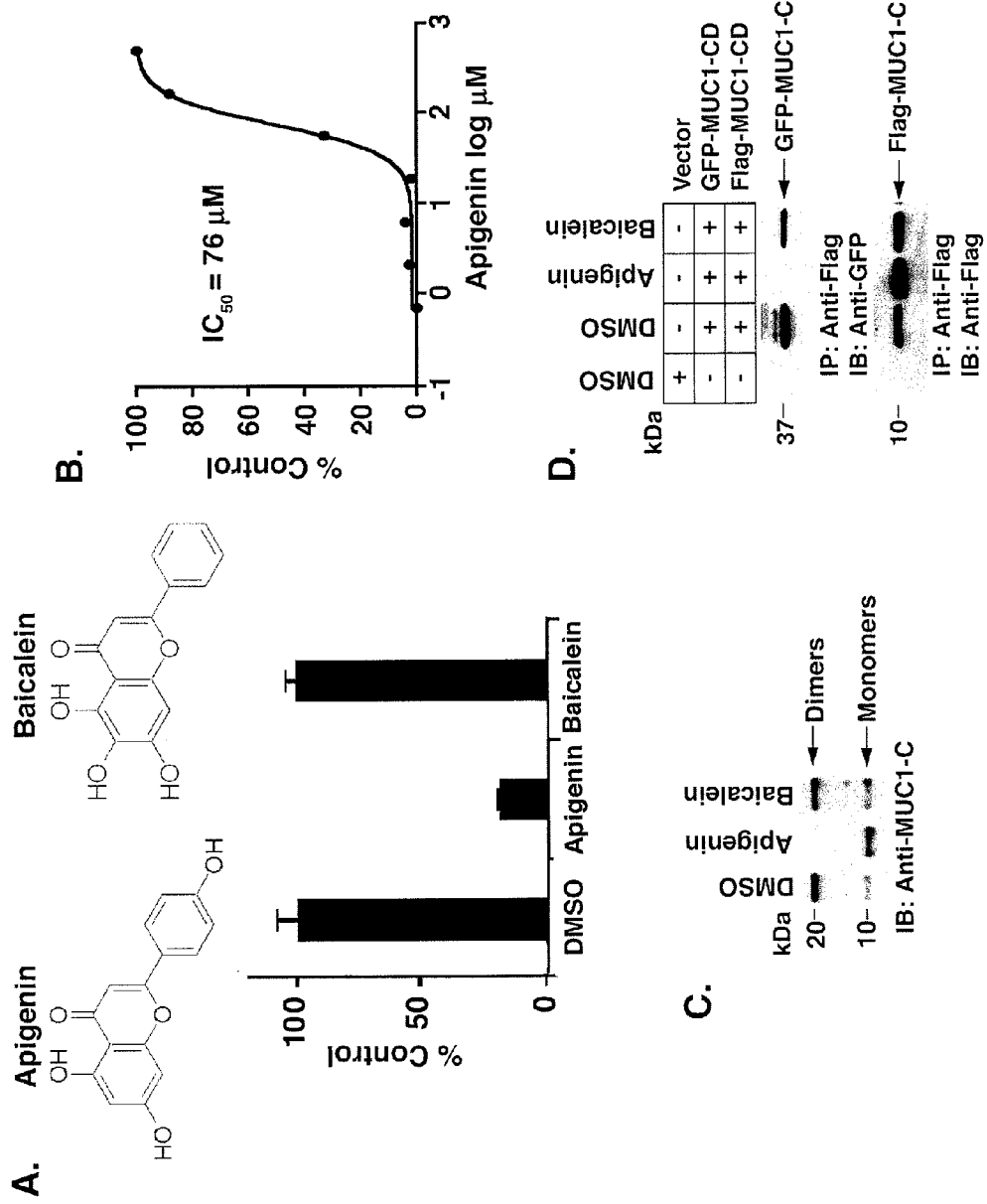
FIG. 12A-D

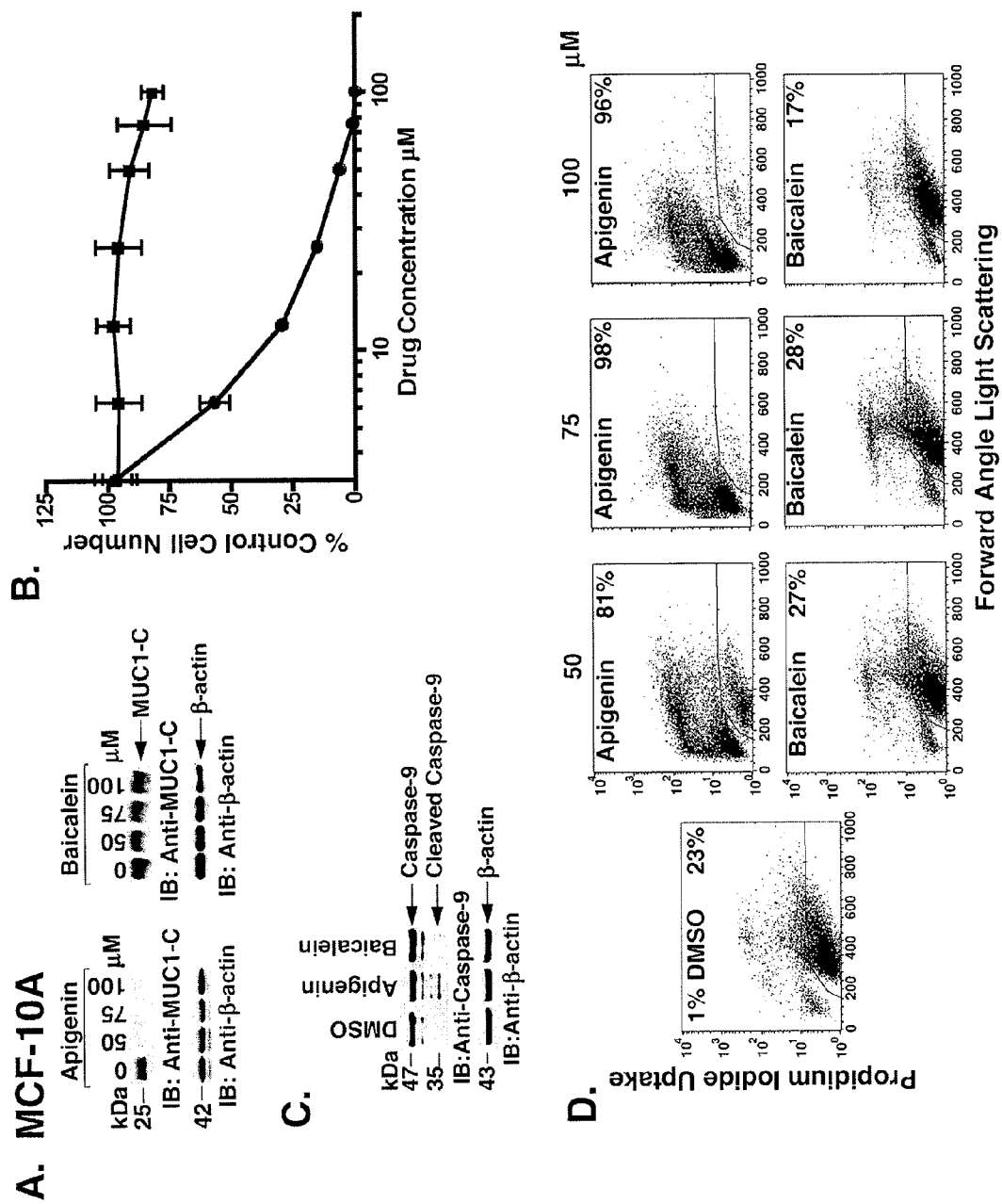
FIG. 13A-D

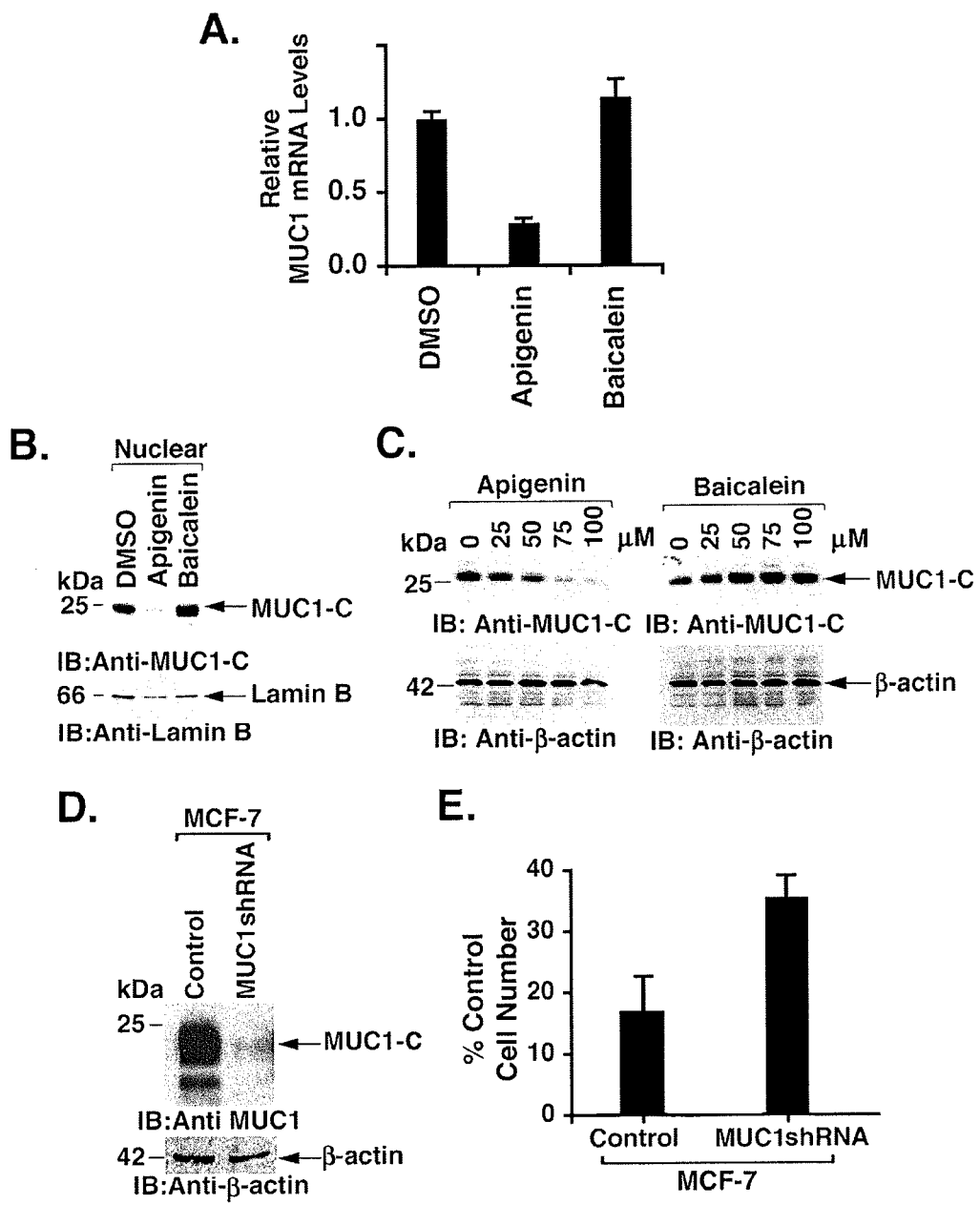
FIG. 14A-E

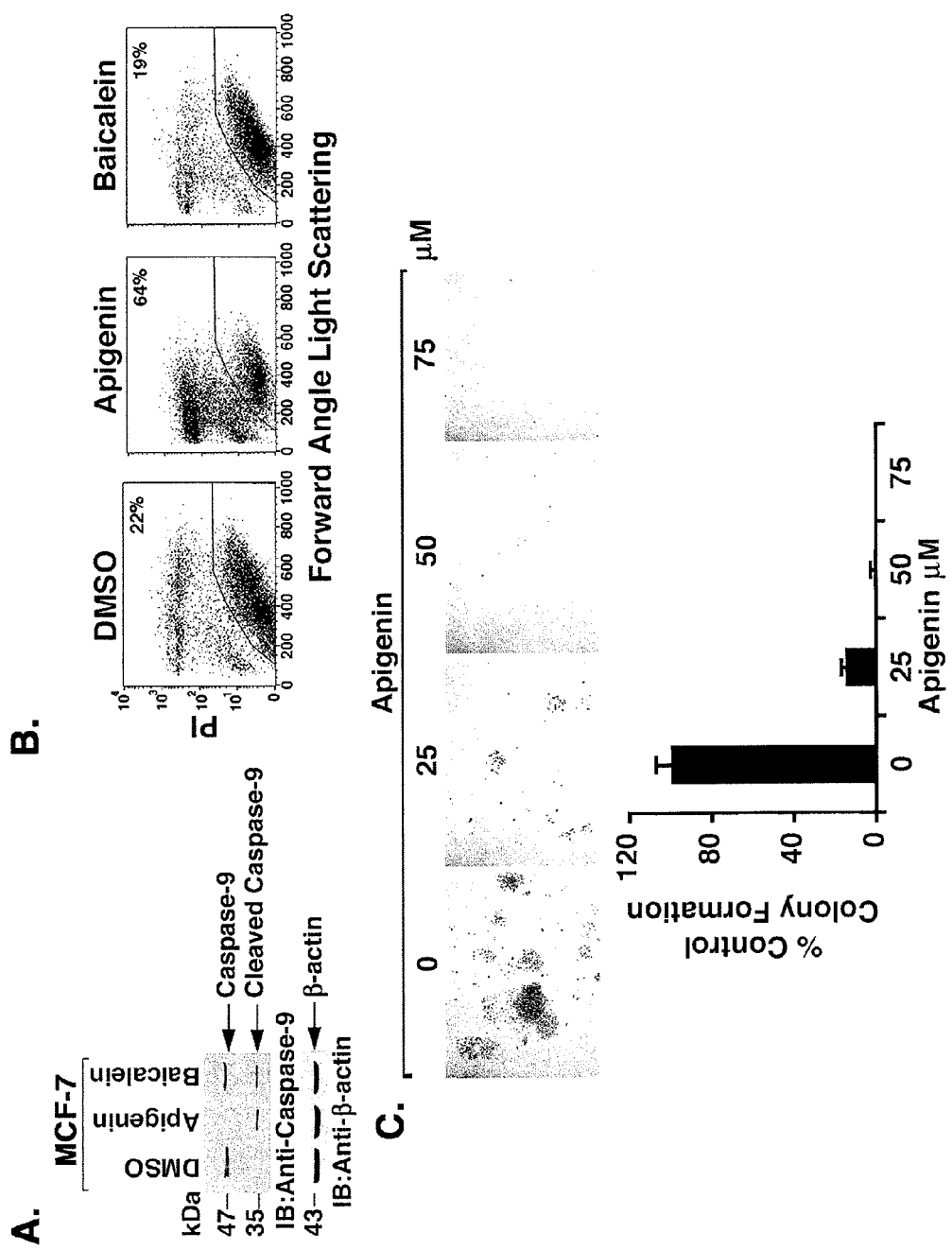
FIG. 15A-C

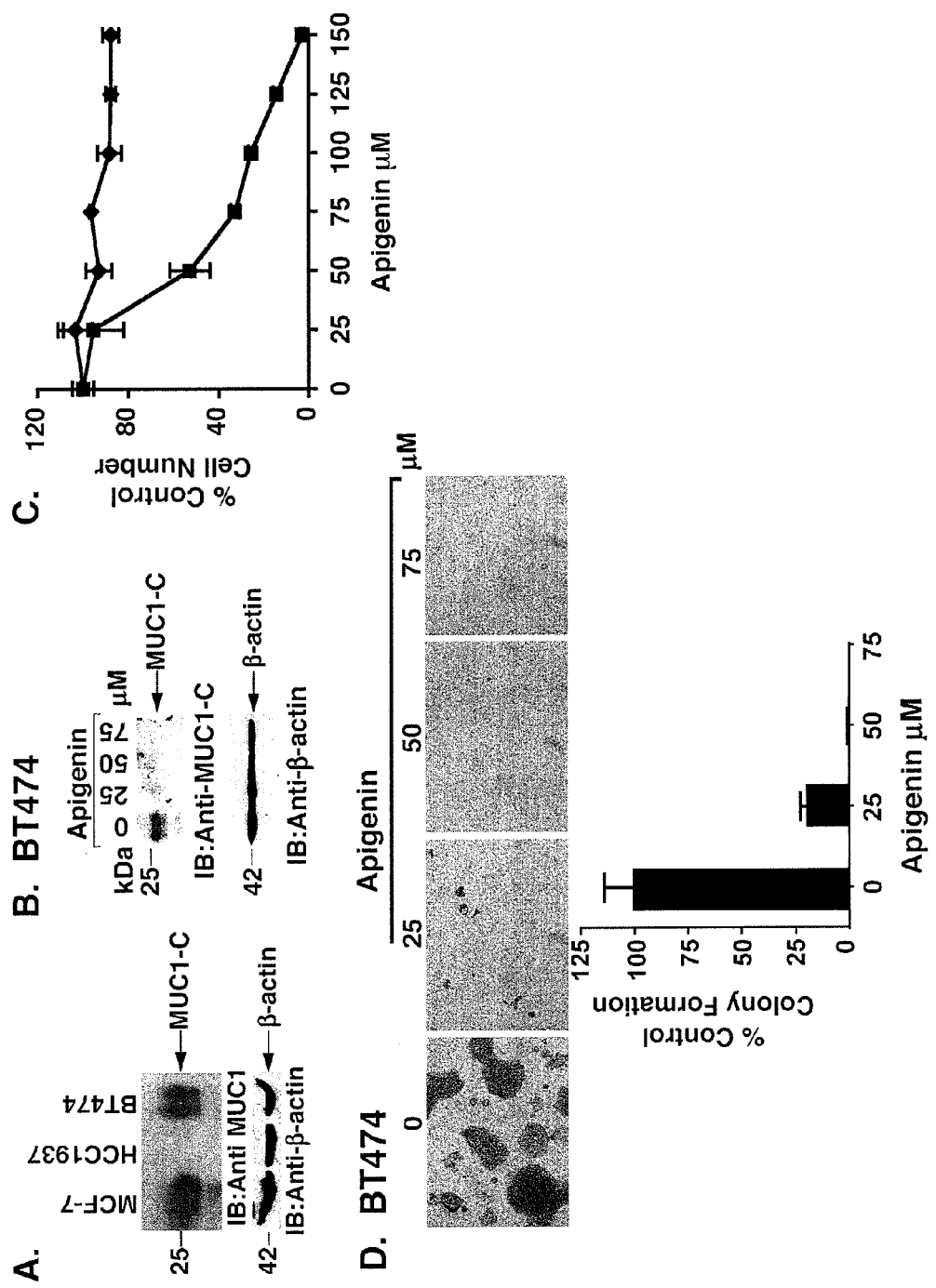
FIG. 16A-D

SMALL MOLECULE INHIBITORS OF MUC1 AND METHODS OF IDENTIFYING THE SAME

This application claims benefit of priority to U.S. Provisional Application Ser. No. 61/313,996, filed Mar. 15, 2010, the entire contents of which are hereby incorporated by reference.

BACKGROUND OF THE INVENTION

1. Field of the Invention

This invention relates to regulation of identification of inhibitors of MUC1 inflammatory signaling. In particular, MUC1 peptides derived from a particular region of the MUC1 cytoplasmic domain have been shown to inhibit MUC1 oligomerization, and thus provide a model system for identifying and characterizing inhibitors of this event. Through the use of such screening methods, small molecule inhibitors of MUC1 oligomerization are identified. These inhibitors will find use in treating a variety of MUC1-related inflammatory disorders, including MUC1-related cancers.

2. Related Art

A. MUC1 in Cancer

Mucins are extensively O-glycosylated proteins that are predominantly expressed by epithelial cells. The secreted and membrane-bound mucins form a physical barrier that protects the apical borders of epithelial cells from damage induced by toxins, microorganisms and other forms of stress that occur at the interface with the external environment. The transmembrane mucin 1 (MUC1) can also signal to the interior of the cell through its cytoplasmic domain. MUC1 has no sequence similarity with other membrane-bound mucins, except for the presence of a sea urchin sperm protein-enterokinase-agrin (SEA) domain (Duraisamy et al., 2006). In that regard, MUC1 is translated as a single polypeptide and then undergoes autocleavage at the SEA domain (Macao, 2006).

The MUC1 N-terminal subunit (MUC1-N) contains variable numbers of tandem repeats with a high proportion of serines and threonines that are modified by O-glycosylation (Siddiqui, 1988). MUC1-N extends beyond the glycocalyx of the cell and is tethered to the cell surface through noncovalent binding to the transmembrane MUC1 C-terminal subunit (MUC1-C) (Merlo, 1989). MUC1-C consists of a 58-amino acid extracellular domain, a 28-amino acid transmembrane domain and a 72-amino acid cytoplasmic domain that interacts with diverse signaling molecules (Kufe, 2008). Shedding of MUC1-N into the protective physical barrier leaves MUC1-C at the cell surface as a putative receptor to transduce intracellular signals that confer growth and survival (Ramasamy et al., 2007; Ahmad et al., 2007).

Available evidence indicates that human carcinomas have exploited MUC1 function in promoting tumorigencity. In this context, with transformation and loss of polarity, MUC1 is expressed at high levels on the entire cell surface in carcinomas of the breast and other epithelia (Kufe, 1984). Other work has shown that overexpression of MUC1 confers anchorage-independent growth and tumorigenicity (Li et al., 2003a; Raina et al., 2004; Ren et al., 2004; Wei et al., 2005), at least in part through stabilization of β-catenin (Huang et al., 2005). Moreover, consistent with a survival function for normal epithelial cells, overexpression of MUC1 confers resistance of carcinoma cells to stress-induced apoptosis (Ren et al., 2004; Yin and Kufe, 2003; Yin et al., 2004; Yin et al., 2007).

Loss of restriction to the apical membrane allows for the formation of complexes with the epidermal growth factor receptor (EGFR) and coactivation of EGFR-mediated signaling (Li et al., 2001; Ramasamy et al., 2007). Overexpression of MUC1 by carcinoma cells is also associated with accumulation of the MUC1-C in the cytosol and targeting of this subunit to the nucleus (Li et al., 2003b; Li et al., 2003c) and mitochondria (Ren et al., 2004; Ren et al., 2006). Importantly, oligomerization of MUC1-C is necessary for its nuclear targeting and interaction with diverse effectors (Leng et al., 2007). For example, the MUC1-C cytoplasmic domain (MUC1-CD) functions as a substrate for c-Src (Li et al., 2001), c-Abl (Raina et al., 2006), protein kinase Cδ (Ren et al., 2002) and glycogen synthase kinase 3β (Li et al., 1998) and interacts directly with the Wnt pathway effector, β-catenin (Yamamoto et al., 1997; Huang et al., 2005), and the p53 tumor suppressor (Wei et al., 2005). Thus, while oligomerization appears to be important, there has been no direct evidence that interference with MUC1 oligomer formation would have any beneficial effects in tumor cells, much less how this might be accomplished.

B. MUC1 as an Inflammatory Signaling Agent

The NF-κB proteins (RelA/p65, RelB, c-Rel, NF-κB1/p50 and NF-κB2/p52) are ubiquitously expressed transcription factors. In the absence of stimulation, NF-κB proteins localize to the cytoplasm in complexes with IκBα and other members of the IκB family of inhibitor proteins (Hayden & Ghosh, 2008). Phosphorylation of IκBα by the high molecular weight IκB kinase (IKKα, IKKβ, IKKγ) complex induces ubiquitination and degradation of IκBα, and thereby release of NF-κB for nuclear translocation. In turn, activation of NF-κB target genes contributes to tumor development through regulation of inflammatory responses, cellular proliferation and survival (Karin & Lin, 2002). NF-κB p65, like other members of the family, contains an N-terminal Rel homology domain (MID) that is responsible for dimerization and DNA binding. The RHD also functions as a binding site for ankyrin repeats in the IκBα protein, which blocks the NF-κB p65 nuclear localization signal (NLS). The NF-κB-IκBα complexes shuttle between the nucleus and cytoplasm (Hayden & Ghosh, 2008). Activation of the canonical NF-κB pathway, for example in the cellular response to tumor necrosis α (TNFα), induces IKKβ-mediated phosphorylation of IκBα and its degradation, with a shift in the balance of NF-κB p65 to the nucleus. The nuclear NF-κB dimers engage κB consensus sequences, as well as degenerate variants, in promoter and enhancer regions (Hoffman et al., 2006; Gilmore, 2008). Activation of NF-κB target genes is then further regulated by posttranslational modification of NF-κB p65 and its interaction with transcriptional coactivators (Hayden & Ghosh, 2008). One of the many NF-κB target genes is IκBα, the activation of which results in de novo synthesis of IκBα and termination of the NF-κB transcriptional response.

The transmembrane MUC1 C-terminal subunit (MUC1-C) functions as a receptor (Ramasamy et al., 2007) and contains a 72-amino acid cytoplasmic domain (MUC1-CD) that is sufficient for inducing transformation (Huang et al., 2005). The MUC1-C subunit is also targeted to the nucleus by a process dependent on its oligomerization (Leng et al., 2007). MUC1-CD functions as a substrate for phosphorylation by the epidermal growth factor receptor (Li et al. 2001), c-Src (Li et al., 2001), glycogen synthase kinase 3β (GSK3β) (Li et al., 1998) and c-Abl (Ahmad et al., 2006). MUC1-CD also stabilizes the Wnt effector, β-catenin, through a direct interaction and thereby contributes to transformation (Huang et al., 2005). Other studies have demonstrated that MUC1-CD interacts directly with IKKβ and IKKγ, and contributes to activation of the IKK complex (Ahmad et al., 2007). Significantly, constitutive activation of NF-κB p65 in human carcinoma cells is downregulated by silencing MUC1, indicating that MUC1-CD has a functional role in regulation of the NF-κB p65 pathway (Ahmad et al., 2007). These findings have also suggested that MUC1-CD function could be targeted with small molecules to disrupt NF-κB signaling in carcinoma cells. However, to date, there are no reports of MUC1 antagonists that impact the signaling of NF-κB.

Members of the signal transducer and activator of transcription (STAT) family also have been implicated in transformation, tumor cell survival, invasion and metastasis (Yu and Jove, 2004). The STAT3 transcription factor was identified as an effector of the interleukin-6 (IL-6) inflammatory response (Wegenka, 1994). STAT3 is activated by Janus-activated kinase (JAK)-1 phosphorylation of the IL-6 receptor, recruitment of STAT3 and then phosphorylation of STAT3 on a conserved tyrosine at position 705 (Yu and Jove, 2004). Activation of the epidermal growth factor receptor is also associated with direct phosphorylation of STAT3 on Tyr-705. In turn, phosphorylated STAT3 undergoes dimerization, translocates to the nucleus and induces activation of STAT3 target genes, which encode regulators of cell cycle progression (cyclin D1 and c-Myc) and inhibitors of apoptosis (survivin and Bcl-xL) (Alvarez, 2005; Alvarez, 2006). Activated STAT3 induces transformation (Bromberg, 1999). Moreover, STAT3 activation has been detected in diverse carcinomas and hematologic malignancies (Aaronson and Horvath, 2002; Bowman, 2000; Yu and Jove, 2004), consistent with involvement of STAT3 in the transcription of genes that control growth and survival. In this regard, small molecule inhibitors of the JAK-1→STAT3 pathway have anti-cancer activity in vitro and in animal models (Song, 2005; Siddiquee, 2007; Ahmad, 2008; Germain and Frank, 2007). In addition, aptamers that block EGFR signaling to STAT3 inhibit growth of malignant epithelial and hematologic cells (Buerger, 2003). These findings have collectively supported the importance of the STAT3 pathway in linking inflammation with tumorigenesis.

SUMMARY OF THE INVENTION

Thus, in accordance with the present invention, there is provided a method of identifying a MUC1-oligomerization inhibitory substance comprising (a) providing a first MUC1 peptide comprising at least 4 consecutive MUC1 residues and no more than about 75 consecutive MUC1 residues and comprising the sequence CQC, wherein the amino-terminal cysteine of CQC is covered on its $NH_2$-terminus by at least one amino acid residue that need not correspond to the native MUC-1 transmembrane sequence; (b) providing a second MUC1 peptide comprising at least 4 consecutive MUC1 residues and no more than about 75 consecutive MUC1 residues and comprising the sequence CQC, wherein the amino-terminal cysteine of CQC is covered on its $NH_2$-terminus by at least one amino acid residue that need not correspond to the native MUC-1 transmembrane sequence; (c) contacting said first peptide with said second peptide in the presence of a candidate inhibitory substance; and (d) measuring the amount of oligomer formation, wherein a reduction in the amount of oligomer formation, as compared to the amount of oligomer formation in the absence of said candidate inhibitory substance, indicates that said candidate inhibitory substance is a MUC1-oligomerization inhibitory substance.

The first and second peptides may, independently, comprise at least 5, 6 or 7 consecutive MUC1 residues, such as CQCR (SEQ ID NO:4), CQCRR (SEQ ID NO:5), CQCRRR (SEQ ID NO:6), CQCRRRR (SEQ ID NO:7), CQCRRK (SEQ ID NO:8), or CQCRRKN (SEQ ID NO:9). The first and/or second peptide may contain no more than 10 consecutive residues, 11 consecutive residues, 12 consecutive residues, 13 consecutive residues, 14 consecutive residues, 15 consecutive residues, 20 consecutive residues, 25 consecutive residues, 30 consecutive residues, 40 consecutive residues, 50 consecutive residues, 60 consecutive residues, 70 consecutive residues, or 75 consecutive residues of MUC1. The first and/or second peptide may contain no more than 10 residues, 11 residues, 12 residues, 13 residues, 14 residues, 15 residues, 20 residues, 25 residues, 30 residues, 40 residues, 50 residues, 60 residues, 70 residues or 75 residues. The first and second peptides both comprise the MUC1 cytoplasmic domain (CD).

The method may further comprise measuring oligomer formation in the absence of said candidate inhibitory substance. The method may also further comprise performing a positive control reaction that measures the amount of oligomer formation in the absence of a known inhibitory substance. The method may further comprise, following step (d), a secondary screen that measures the ability of said candidate inhibitory substance to impair the growth or viability of a MUC1-expressing cancer cell.

The first peptide may be labeled with a detectable molecule and the second peptide may be fixed to a support, and wherein a reduction in the amount of said detectable molecule bound to said support, as compared to the amount of said detectable molecule bound to said support in the absence of said candidate inhibitory substance, indicates that said candidate inhibitory substance is a MUC1-oligomerization inhibitory substance. The support may selected from the group consisting of a plate, a well, filter paper, a bead, a dipstick or a nanoparticle. The detectable molecule may be a fluorescent label, a radiolabel, an enzyme, a chromophore, a chemiluminescent label, or a FRET label.

The first and second peptides may be mixed in solution in the presence of said inhibitor, and oligomerization is measured by gel electrophoresis. The first and second peptides may be mixed in solution in the presence of said inhibitor, and oligomerization is measured by column separation. The first and second peptides may be mixed in solution in the presence of said inhibitor, and said peptides are labeled with FRET labels, and oligomerization is measured by FRET.

In another embodiment, there is provided a method of identifying a MUC1-oligomerization inhibitory substance comprising (a) providing an expression construct encoding a first MUC1 peptide under the control of a promoter, said peptide comprising at least 4 consecutive MUC1 residues and no more than about 75 consecutive MUC1 residues and comprising the sequence CQC, wherein the amino-terminal cysteine of CQC is covered on its $NH_2$-terminus by at least one amino acid residue that need not correspond to the native MUC-1 transmembrane sequence; (b) providing an expression construct encoding a second MUC1 peptide under the control of a promoter, said peptide comprising at least 4 consecutive MUC1 residues and no more than about 75 consecutive MUC1 residues and comprising the sequence CQC, wherein the amino-terminal cysteine of CQC is covered on its $NH_2$-terminus by at least one amino acid residue that need not correspond to the native MUC-1 transmembrane sequence; (c) expressing first and second peptides in the same host cell in the presence of a candidate inhibitory substance; and (d) measuring the amount of oligomer formation, wherein a reduction in the amount of oligomer formation, as compared to the amount of oligomer formation in the absence of said candidate inhibitory substance, indicates that said candidate inhibitory substance is a MUC1-oligomerization inhibitory substance.

In yet another embodiment, there is provided a method of inhibiting inflammatory signaling in a cell comprising contacting said cell with a flavone having the structure of:

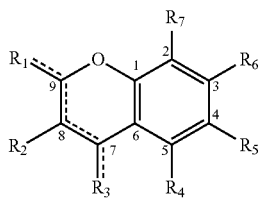

or a salt thereof, wherein
- $R_1$ is H, —OH, =O, substituted or unsubstituted alkyl ($C_{1-8}$), alkoxy($C_{1-8}$), haloalkyl($C_{1-8}$), substituted phenyl or unsubstituted phenyl, wherein if $R_1$ is =O, $C_7$-$C_8$ is a double bond;
- $R_2$ is H, —OH, alkyl($C_{1-8}$), substituted phenyl, unsubstituted phenyl, phenyl, phenyl thiazole, imidazole, pyrazole or furan;
- $R_3$ is H, —OH, =O, halogen, haloalkyl($C_{1-8}$), substituted or unsubstituted alkyl($C_{1-8}$), substituted phenyl or unsubstituted phenyl, wherein if $R_3$ is =O, $C_8$-$C_9$ is a double bond;
- $R_4$ is H or —OH;
- $R_5$ is H, —OH, substituted or unsubstituted alkyl($C_{1-8}$) or alkoxy($C_{1-8}$), or $OR_8$, wherein $R_8$ is alkyl($C_{1-8}$), an ester or an amide;
- $R_6$ is H, —OH, substituted or unsubstituted alkyl($C_{1-8}$) or alkoxy($C_{1-8}$), or $OR_8$, wherein $R_8$ is alkyl($C_{1-8}$), an ester or an amide; and
- $R_7$ is H, —OH, or substituted or unsubstituted alkyl($C_{1-8}$), with the proviso that $R_1$ and $R_3$ cannot both be =O.

$R_1$ may be =O. $R_3$ may be =O. The flavone in Morin, Apigenin, Kaempferol, Fisetin, PD98059, 7-(benzyloxy)-4-(trifluoromethyl)-2H-chromen-2-one or 7-[(3-oxobutan-2-yl)oxy]-4-phenyl-2H-chromen-2-one, or a salt of any of the foregoing.

The cell may be a tumor cell, an endothelial cell or an inflammatory cell, such as a macrophage, a B cell, at T cell, a dendritic cell, a myeloid-derived suppressor cell, an NK cell or a neutrophil. In particular, the cell may be a cancer/tumor cell. The tumor cell may be a MUC1-positive cancer cell, such as a solid tumor cell. The solid tumor cell may be a lung cancer cell, a brain cancer cell, a head & neck cancer cell, a breast cancer cell, a skin cancer cell, a liver cancer cell, a pancreatic cancer cell, a stomach cancer cell, a colon cancer cell, a rectal cancer cell, a uterine cancer cell, a cervical cancer cell, an ovarian cancer cell, a testicular cancer cell, a skin cancer cell or a esophageal cancer cell. The cancer cell may be located in a subject, including a human subject. The cancer subject may receive a second cancer therapy, such as chemotherapy, radiotherapy, immunotherapy, toxin therapy, hormone therapy, gene therapy or surgery. The second therapy may be given at the same time as said flavones, or may be given before or after said flavone. The subject may also suffer from sepsis, an autoimmune disease, acute pancreatitis, burns, cardiovascular disease, ischemia-reperfusion injury, inflammation caused by chemotherapy, radiotherapy or cytokine therapy or acute respiratory distress syndrome.

The method may further comprise contacting said cell with a second anti-inflammatory agent, such as a steroid or a COX-2 inhibitor. The second anti-inflammatory agent may be contacted prior to said compound, after said compound, or at the same time as said compound. The inflammatory signaling may comprise NF-κB-mediated signaling or STAT-mediated signaling, where NF-κB-mediated signaling may comprise NF-κB activation of a target gene selected from the group consisting of Bcl-xL and MUC1, and STAT-mediated signaling may comprise STAT3 activation, including STAT3 activation of a target gene selected from the group consisting of cyclin D1, survivin, Idp1, Idp2, Cdkn1C, Lefty1, Mest, Aes1, Zfp57, Zfp3611, Sh3 bp1, Ccnd3 and MUC1.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed.

(FIG. 1A) Schematic representation of the MUC1-C subunit and the 72-amino acid sequence of MUC1-CD (SEQ ID NO: 1) are shown. The N-terminal 15 amino acids (shaded sequence) MUC1/CQC (SEQ ID NO: 10) and mutated MUC1/AQA (SEQ ID NO: 11) peptides were synthesized with the poly-dArg transduction domain. (FIG. 1B) His-MUC1-CD (1.4 mg/ml) was immobilized on a sensor chip in a BIAcore. MUC1/CQC was injected over the chip at 10 μM. Raw binding data were analyzed by BIAevaluation software version 3.0 and fit to a 1:1 Languir binding model. (FIG. 1C) Purified His-MUC1-CD (1.5 mg/ml) was incubated with PBS, 200 μM MUC1/CQC or 200 μM MUC1/AQA for 1 h at room temperature. The proteins were separated in a non-reducing SDS-polyacrylamide gel and analyzed by immunoblotting with anti-MUC1-C. (FIG. 1D) 293 cells were transiently transfected to express an empty vector or GFP-MUC1-CD and Flag-MUC1-CD. At 48 h after transfection, the cells were treated with 5 μM MUC1/CQC or MUC1/AQA for 3 d. The cells were then harvested for immunoblotting with anti-MUC1-C (left panel). Whole cell lysates were also precipitated with anti-Flag and the precipitates were immunoblotted with the indicated antibodies (right panels).

(FIG. 2A) ZR-75-1 cells were incubated with 5 μM FITC-labeled MUC1/CQC peptide for the indicated times and then analyzed by flow cytometry. The mean fluorescence index (MFI) is included in each of the panels. (FIGS. 2B-C) ZR-75-1 (FIG. 2B) and MCF-7 (FIG. 2C) cells were incubated in the presence of 5 μM MUC1/CQC or MUC1/AQA peptide for 3 d. Whole cell lysates (WCL) (left panels) and nuclear lysates (right panels) were immunoblotted with the indicated antibodies.

(FIG. 4A) ZR-75-1 cells were stably infected with an empty lentivirus (vector) or one expressing a MUC1 siRNA. Lysates for the infected cells were immunoblotted with the indicated antibodies. (FIG. 4B) ZR-75-1/vector cells were left untreated (diamonds), and ZR-75-1/vector (squares) and ZR-75-1/MUC1 siRNA (triangles) cells were treated with 5 µM MUC1/CQC peptide for the indicated times. Viable cell number was determined by trypan blue exclusion. (FIG. 4C) 293 cells were left untreated (diamonds), and treated with 5 µM MUC1/CQC (squares) or MUC1/AQA (triangles) for the indicated times. Viable cell number was determined by trypan blue exclusion. (FIG. 4D) MCF-10A cells were left untreated (left panel), and treated with 5 µM MUC1/CQC (middle panel) or MUC1/AQA (right panel). At 3 d, cells were analyzed for cell cycle distribution. (FIG. 4E) MCF-10A cells were left untreated (diamonds), and treated with 5 µM MUC1/CQC (squares) or MUC1/AQA (triangles) for the indicated times. Viable cell number was determined by trypan blue exclusion.

(FIG. 5A) Four to six week-old female Balb-c nu/nu mice were implanted with 17-β-estradiol plugs. After 24 h, ZR-75-1 breast cancer cells (imbedded in matrigel) were injected subcutaneously in the flank. When tumors were ~150 mm3, the mice were paired matched into groups and injected intraperitoneally with PBS (vehicle control; closed squares), 50 mg/kg MUC1/AQA peptide (control peptide; open squares) or 10 mg/kg MUC1/CQC peptide (closed triangles) daily for 21 d. Another group was treated with 50 mg/kg MUC1/CQC peptide daily for 6 d (open triangles). Mice were weighed twice weekly and tumor measurements were performed every 4 d. (FIGS. 5B and 5C). On day 24 (asterisk), tumors harvested from the control group and the group treated with 50 mg/kg/d×6 d were stained with H&E (FIG. 5B) and with an antibody against MUC1 (FIG. 5C).

FIG. 8—293 cells transiently transfected to express an empty vector or GFP-MUC1-CD and Flag-MUC1-CD. At 48 he after transfection, cells were left untreated (control), or treated with 5 µmol/L GO-201 or CP-1 each day for 3 days. The cells were then harvested for immunoblotting with anti-MUC1-C (left). Whole-cell lysates were also precipitated with anti-Flag and the precipitates were immunoblotted with the indicated antibodies (right).

FIG. 10—Hits from Secondary Screen of a 500+ Flavone Library.

FIGS. 11A-C—Identification of MUC1-CD dimerization inhibitors in a small molecule screen. (FIG. 11A) Schematic representation of the MUC1-C subunit with the 58 amino acid (aa) extracellular domain (ECD), the 28 aa transmembrane domain (TD) and the 72 aa cytoplasmic domain (CD; SEQ ID NO: 1). The sequence of MUC1-CD is included with highlighting of the CQC dimerization motif. (FIG. 11B) The assay for identification of MUC1-CD dimerization inhibitors is depicted with the following steps: (i) coating of MUC1-CD onto a microplate, (ii) adding soluble biotinylated MUC1-C and 100 IIM compound, and (iii) addition of streptavidin-HRP and then peroxide with conversion by HRP to a blue color. The signal is measured by EnVision and proportional to the amount of bound biotin-labeled MUC1-CD. (FIG. 11C) The number of compounds (shaded bars) screened from the indicated libraries is shown with the percentage of positive hits (solid bars) as determined by greater than 50% inhibition of MUC1-CD dimerization.

FIGS. 12A-D—Apigenin is an inhibitor of MUC1-CD dimerization in vitro and in cells. (FIG. 12A) Structures of apigenin and its analogue baicalein. Using the in vitro screening assay, dimerization of MUC1-CD was assessed in the presence of 100 µM apigenin or 100 µM baicalein each dissolved in 0.1% DMSO. The results (mean±SD of 3 determinations) are expressed as percentage of control dimerization in the presence of DMSO alone. (FIG. 12B) MUC1-CD dimerization was assessed in the presence of the indicated concentrations of apigenin in the in vitro screening assay. The results are expressed as the percentage of inhibition with a calculated IC50 of 76 µM. (FIG. 12C) Soluble MUC1-CD was incubated in the presence of 1% DMSO, 1 mM apigenin or 1 mM baicalein for 1 h at room temperature. Monomers and dimmers were assessed by electrophoresis in a non-reducing gel and immunoblotting with anti-MUC1-C. (FIG. 12D) 293 cells were transiently transfected to express an empty vector or GFP-MUC1-CD and Flag-MUC1-CD. At six hours after transfection, the cells were left untreated, and treated with 75 µM apigenin or baicalein for 3 days. Whole-cell lysates were precipitated with anti-Flag, and the precipitates were immunoblotted with the indicated antibodies.

FIGS. 13A-D—Apigenin downregulates MUC1 and confers death of MCF-10A cells. (FIG. 13A) MCF-10A cells were treated with the indicated concentrations of apigenin and baicalein for 3 d, washed and then treated for an additional 3 d. Lysates were immunoblotted with the indicated antibodies. (FIG. 13B) MCF-10A cells were treated with the indicated concentrations apigenin (circles) and baicalein (squares) for 3 d. Viable cell number was determined by the MTS assay. The results (mean+SD of 3 determinations) are expressed as percentage of control growth in the presence of DMSO. (FIG. 13C) MCF-10A cells were treated with DMSO, 75 µM apigenin or 75 µM baicalein for 3 d. Lysates were subjected to immunoblotting with the indicated antibodies. (FIG. 13D) MCF-10A cells were treated with DMSO, 75 µM apigenin or 75 µM baicalein for 3 d, stained with propidium iodide and analyzed by flow cytometry. The percentage of cells with loss of cell membrane integrity is included in the panels.

FIGS. 14A-E—Apigenin suppresses MUC1 expression in MCF-7 cells. (FIG. 14A) MCF-7 cells were treated with DMSO vehicle, 75 µM apigenin or 75 µM baicalein for 3 d. Total RNA was assayed for MUC1 mRNA levels by qRT-PCR. The results (mean+SD of 3 determinations) are expressed as relative MUC1 mRNA levels as compared to that obtained in cells treated with DMSO. (FIGS. 14B-C) MCF-7 cells were treated with the indicated concentrations of apigenin and baicalein for 3 days. Nuclear (FIG. 14B) and whole cell lysates (FIG. 14C) were immunoblotted with the indicated antibodies. D. Lysates from MCF-7 cells were infected to stably express a control lentivirus and one with a MUC1 shRNA were immunoblotted with the indicated antibodies. (FIG. 14E) The indicated MCF-7 cells were treated with 75 mM apigenin for 3 d. Viable cell number was determined by the MTS assay. The results (mean+SD of 3 determinations) are expressed as percentage of control growth in the presence of DMSO.

FIGS. 15A-C—Apigenin inhibits MCF-7 clonogenic survival. (FIG. 15A) MCF-7 cells were treated with DMSO, 75 µM apigenin or 75 µM baicalein for 3 d. Lysates were immunoblotted with the indicated antibodies. (FIG. 15B) MCF-7 cells were treated with DMSO, 75 µM apigenin or 75 µM baicalein for 3 d, stained with propidium iodide and analyzed by flow cytometry. The percentage of cells with loss of cell membrane integrity is included in the panels. (FIG. 15C) MCF-7 cells were plated at a density of 1000 cells/6 cm dish. At 24 h after seeding, DMSO or apigenin at concentrations of 25, 50 and 75 µM was added to the medium. After 2 weeks, colonies were stained with crystal violet. The results (mean+SD of 3 determinations) are expressed as percentage of control colony formation in the presence of DMSO.

FIGS. 16A-D—Effects of apigenin on breast cancer cells without and with endogenous MUC1 expression. (FIG. 16A) Lysates from human MCF-7, HCC1937 and BT474 cells were immunoblotted with the indicated antibodies. (FIG. 16B) BT474 cells were treated with indicated concentrations of apigenin and baicalein for 3 d, washed and then treated for an additional 3 d. Lysates were immunoblotted with the indicated antibodies. (FIG. 16C) BT474 (triangles) and HCC1937 (squares) cells were treated with apigenin for 3 d. Viable cell numbers were determined by MTS assay. The results (mean+SD of 3 determinations) are expressed as percentage of control growth in the presence of DMSO. (FIG. 16D) BT474 cells were plated at a density of 5000 cells/6 cm dish. At 24 h after seeding, DMSO or apigenin at concentrations of 25, 50 and 75 µM was added to the medium. After 2 weeks, colonies were stained with crystal violet. The results (mean+SD of 3 determinations) are expressed as percentage of control colony formation in the presence of DMSO.

DESCRIPTION OF ILLUSTRATIVE EMBODIMENTS

Figure 1A:
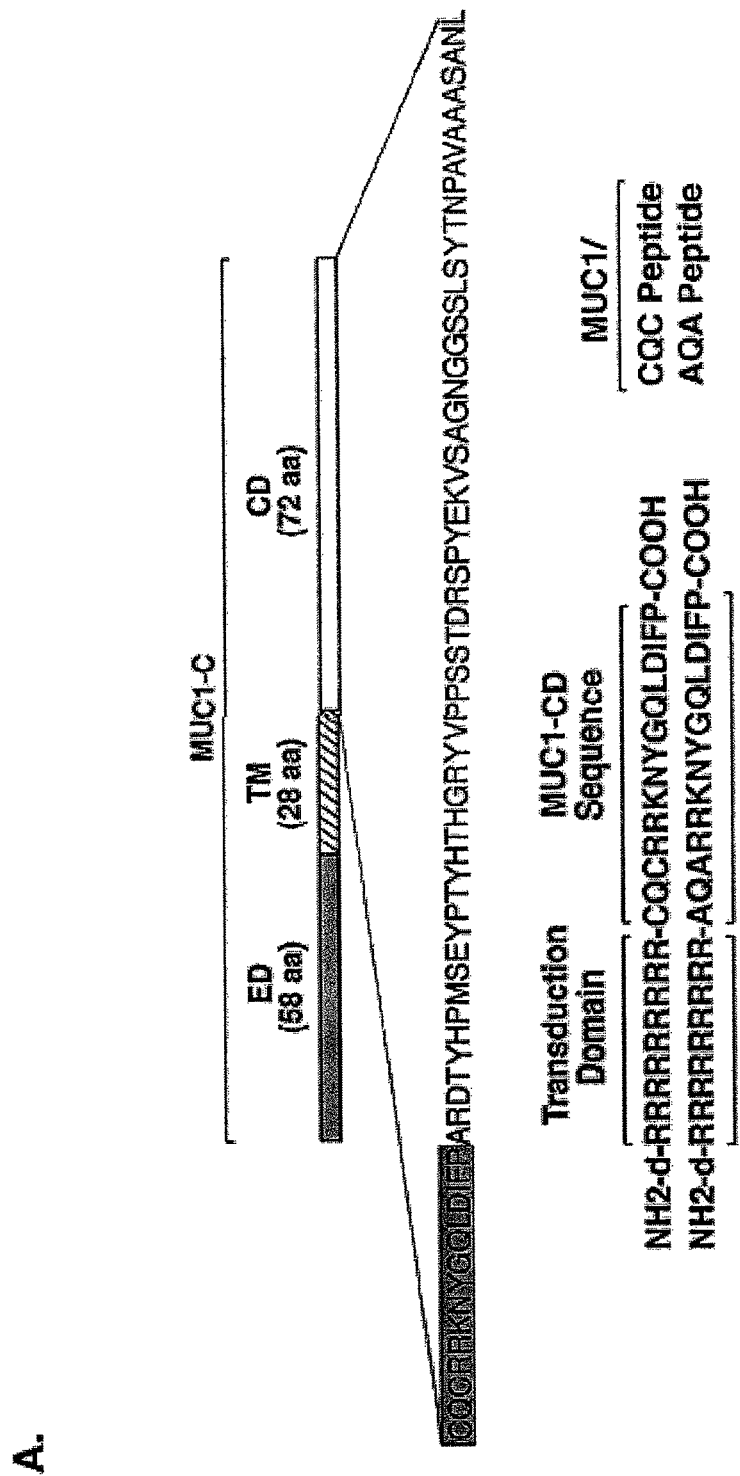
FIGS. 1A-D. MUC1/CQC peptide blocks MUC1 oligomerization.
Figure 1B:
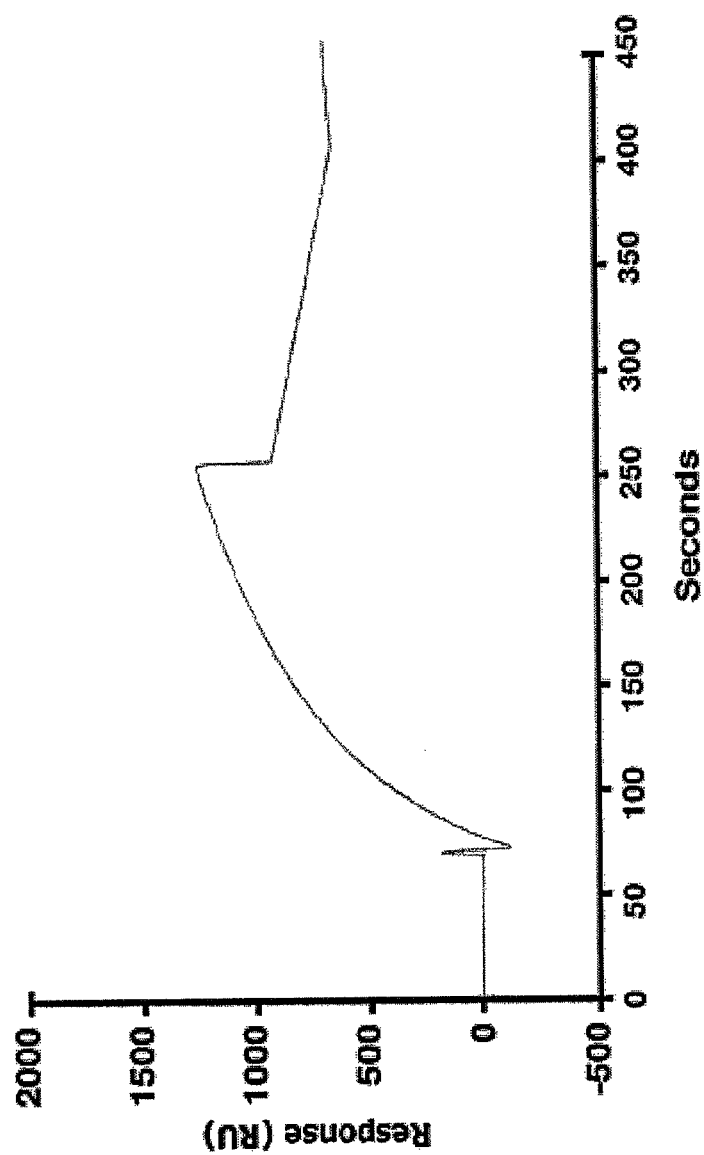

MUC1 has been studied extensively by the inventors and others for its role in cancer. As discussed above, human MUC1 is heterodimeric glycoprotein, translated as a single polypeptide and cleaved into N- and C-terminal subunits in the endoplasmic reticulum (Ligtenberg et al., 1992; Macao et al., 2006; Levitin et al., 2005). Aberrant overexpression of MUC1, as found in most human carcinomas (Kufe et al., 1984), confers anchorage-independent growth and tumorigenicity (Li et al., 2003a; Huang et al., 2003; Schroeder et al., 2004; Huang et al., 2005). Other studies have demonstrated that overexpression of MUC1 confers resistance to apoptosis induced by oxidative stress and genotoxic anti-cancer agents (Yin and Kufe, 2003; Ren et al., 2004; Raina et al., 2004; Yin et al., 2004; Raina et al., 2006; Yin et al., 2007).

The family of tethered and secreted mucins functions in providing a protective barrier of the epithelial cell surface. With damage to the epithelial layer, the tight junctions between neighboring cells are disrupted, and polarity is lost as the cells initiate a heregulin-induced repair program (Vermeer et al., 2003). MUC1-N is shed from the cell surface (Abe and Kufe, 1989), leaving MUC1-C to function as a transducer of environmental stress signals to the interior of the cell. In this regard, MUC1-C forms cell surface complexes with members of the ErbB receptor family, and MUC1-C is targeted to the nucleus in the response to heregulin stimulation (Li et al., 2001; Li et al., 2003c). MUC1-C also functions in integrating the ErbB receptor and Wnt signaling pathways through direct interactions between the MUC1 cytoplasmic domain (CD) and members of the catenin family (Huang et al., 2005; Li et al., 2003c; Yamamoto et al., 1997; Li et al., 1998; Li et al., 2001; Li and Kufe, 2001). Other studies have demonstrated that MUC1-CD is phosphorylated by glycogen synthase kinase 3β, c-Src, protein kinase Cδ, and c-Abl (Raina et al., 2006; Li et al., 1998; Li et al., 2001; Ren et al., 2002).

The mechanisms responsible for nuclear targeting of MUC1-C are unclear. Proteins containing a classical nuclear localization signal (NLS) are imported into the nucleus by first binding to importin α and then, in turn, importin β (Weis, 2003). The cargo-importin α/β complex docks to the nuclear pore by binding to nucleoporins and is transported through the pore by a mechanism dependent on the Ran GTPase. Classical NLSs are monopartite with a single cluster of 4-5 basic amino acids or bipartite with two clusters of basic amino acids separated by a linker of 10-12 amino acids. MUC1-CD contains a RRK motif that does not conform to a prototypical monopartite NLS (Hodel et al., 2002). However, certain proteins containing non-classical NLSs are transported through the nuclear pore by binding directly to importin β (Kau et al., 2004). Importin β associates with several nucleoporins (Ryan and Wente, 2000), including Nup62, which is located on both the cytoplasmic and nucleoplasmic faces of nuclear pore complexes (Percipalle et al., 1997). Other studies have indicated that β-catenin is imported into the nucleus by an importin- and nucleoporin-independent mechanism (Suh and Gumbiner, 2003).

In 2006, the inventors reported that MUC1 is imported into the nucleus by a mechanism involving binding to Nup62 (Leng et al., 2007). They also demonstrate that MUC1 forms oligomers through a CQC motif in the MUC1 cytoplasmic domain and that MUC1 oligomerization is necessary for nuclear import. In 2007, they also demonstrated that overexpression of MUC1 in human carcinoma cells is associated with constitutive activation of NF-kappaB p65 (Ahmad et al. 2007). MUC1 was shown to interact with the high-molecular-weight IκB kinase (IKK) complex in vivo, and that the MUC1 cytoplasmic domain binds directly to IKKβ and IKKγ. Interaction of MUC1 with both IKKβ and IKKγ is necessary for IKK activation, resulting in phosphorylation and degradation of IκBα. These findings indicated that MUC1 is important for physiological activation of IKKβ and that overexpression of MUC1, as found in human cancers, confers sustained induction of the IKKβ-NF-κB p65 pathway.

In recent work, the inventors have extended their research to encompass a further elucidation of the role that the CQC motif plays in oligomer formation. They also have demonstrated that short peptides corresponding to this region are able to disrupt MUC1 oligomer formation, preventing transport into the nucleus of tumor cells. These peptides are able to inhibit tumor cell growth, as well as induce apoptosis in such cells and even necrosis of tumor tissue. The inventors also demonstrated that MUC1-CD binds directly to NF-κB p65 and blocks the interaction between NF-κB p65 and IκBα, and showed that the MUC1-C subunit associates with NF-κB p65 on the promoters of NF-κB target genes and promotes NF-κB-mediated transcription. Their results also demonstrate that an inhibitor of MUC1-C oligomerization blocks the MUC1 interaction with NF-κB p65 and constitutive activation of the inflammatory NF-κB pathway. A similar interaction with STAT3, another inflammatory signaling factor, has been demonstrated, even further implicating MUC1 in this process.

The present inventors now have taken advantage of the MUC1 oligomerization phenomenon, and the additional knowledge that MUC1-derived peptides can interfere with this process by binding the MUC1 oligomerization domain, to create a high-throughput screening assay for additional oligomerization inhibitors. Such assays, and small molecules identified using these assays, are described in detail below.

I. MUC1 PEPTIDES AND ASSAYS

A. MUC1 Structure and Function

MUC1 is a mucin-type glycoprotein that is expressed on the apical borders of normal secretory epithelial cells (Kufe et al., 1984). MUC1 forms a heterodimer following synthesis as a single polypeptide and cleavage of the precursor into two subunits in the endoplasmic reticulum (Ligtenberg et al., 1992). The cleavage may be mediated by an autocatalytic process (Levitan et al., 2005). The >250 kDa MUC1 N-terminal (MUC1 N-ter, MUC1-N) subunit contains variable numbers of 20 amino acid tandem repeats that are imperfect with highly conserved variations and are modified by O-linked glycans (Gendler et al., 1988; Siddiqui et al., 1988). MUC1-N is tethered to the cell surface by dimerization with the ~23 kDa C-terminal subunit (MUC1 C-ter, MUC1-C), which includes a 58 amino acid extracellular region, a 28 amino acid transmembrane domain and a 72-amino acid cytoplasmic domain (CD; SEQ ID NO:1) (Merlo et al., 1989). The human MUC1 sequence is shown below:

(SEQ ID NO: 2)
GSVVVQLTLAFREGTINVHDVETQFNQYKTEAASRYNLTISDVSVSDVPF

PFSAQSGAGVPGWGIALLVLVCVLVALAIVYLIALAVCQCRRKNYGQLD

IFPARDTYHPMSEYPTYHTHGRYVPPSSTDRSPYEKVSAGNGGSSLSY

TNPAVAATSANL

The bold sequence indicates the CD, and the underlined portion is an oligomer-inhibiting peptide (SEQ ID NO:3). With transformation of normal epithelia to carcinomas, MUC1 is aberrantly overexpressed in the cytosol and over the entire cell membrane (Kufe et al., 1984; Perey et al., 1992). Cell membrane-associated MUC1 is targeted to endosomes by clathrin-mediated endocytosis (Kinlough et al., 2004). In addition, MUC1-C, but not MUC1-N, is targeted to the nucleus (Baldus et al., 2004; Huang et al., 2003; Li et al., 2003a; Li et al., 2003b; Li et al., 2003c; Wei et al., 2005; Wen et al., 2003) and mitochondria (Ren et al., 2004).

MUC1 interacts with members of the ErbB receptor family (Li et al., 2001b; Li et al., 2003c; Schroeder et al., 2001) and with the Wnt effector, β-catenin (Yamamoto et al., 1997). The epidermal growth factor receptor and c-Src phosphorylate the MUC1 cytoplasmic domain (MUC1-CD) on Y-46 and thereby increase binding of MUC1 and β-catenin (Li et al., 2001a; Li et al., 2001b). Binding of MUC1 and β-catenin is also regulated by glycogen synthase kinase 3β and protein kinase Cδ (Li et al., 1998; Ren et al., 2002). MUC1 colocalizes with β-catenin in the nucleus (Baldus et al., 2004; Li et al., 2003a; Li et al., 2003c; Wen et al., 2003) and coactivates transcription of Wnt target genes (Huang et al., 2003). Other studies have shown that MUC1 also binds directly to p53 and regulates transcription of p53 target genes (Wei et al., 2005). Notably, overexpression of MUC1 is sufficient to induce anchorage-independent growth and tumorigenicity (Huang et al., 2003; Li et al., 2003b; Ren et al., 2002; Schroeder et al., 2004).

Most mitochondrial proteins are encoded in the nucleus and are imported into mitochondria by translocation complexes in the outer and inner mitochondrial membranes. Certain mitochondrial proteins contain N-terminal mitochondrial targeting sequences and interact with Tom20 in the outer mitochondrial membrane (Truscott et al., 2003). Other mitochondrial proteins contain internal targeting sequences and interact with the Tom70 receptor (Truscott et al., 2003). Recent work showed that mitochondrial proteins without internal targeting sequences are delivered to Tom70 by a complex of HSP70 and HSP90 (Young et al., 2003).

B. MUC1 Peptides

The present invention involves, in one aspect, the use of MUC1 peptides that are capable of binding to the MUC1 oligomerization domain. The structural features of these peptides are as follows.

First, the peptides have no more than 75, including those peptides of 20 or less, 15 or less, 10 or less, 9 or less, 8 or less, 7 or less, 6 or less, 5 or less and even only 4 consecutive residues of MUC1. Thus, the term "a peptide having no more than 75 consecutive residues," even when including the term "comprising," cannot be understood to comprise a greater number of consecutive MUC1 residues.

Second, the peptides will contain the CQC motif, and may further comprise the CQCR, CQCRR, or CQCRRK motifs. Thus, the peptides will have, at a minimum, these four, five or six consecutive residues of the MUC1-C domain.

Third, the peptides will have at least one amino acid residue attached to the NH₂-terminal side of the first C residue in the CQCRRK motif, such that the first C residue is "covered" by that at least one amino acid attached thereto. This residue may be native to MUC1 (i.e., from the transmembrane domain), may be selected at random (any of the twenty naturally-occurring amino acids or analogs thereof), or may be part of another peptide sequence (e.g., a tag sequence for purification, a stabilizing sequence, or a cell delivery domain).

In general, the peptides will be 75 residues or less, again, comprising no more than 20 consecutive residues of MUC1. The overall length may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75 residues. Ranges of peptide length of 4-75 residues, 7-75 residues, 4-50 residues, 7-50 residues, 4-25 residues 7-25, residues, 4-20 residues, 7-20 residues, and 4-15 residues, and 7-15 residues are contemplated. The number of consecutive MUC1 residues may be 3, 4, 5, 6, 7, 8, 9, 10, 11, 12, 13, 14, 15, 16, 17, 18, 19 or 20. Ranges of consecutive residues of 4-20 residues, 5-20 residues, 6-20 residues, 7-20 residues, 4-15 residues, 5-15 residues, 6-15 residues and 7-15 residues are contemplated.

C. Peptide Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the twenty standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

D. Supports

In various contexts, some discussed further below, it may prove useful to attach a MUC1 polypeptide, MUC1 fragment (e.g., MUC1 CD) or MUC1 peptide to a support. A wide variety of supports are known in the art, and include polystyrene dishes, multi-well (6-, 24-, 96-, 384-well) plates, filter paper, membranes, dipsticks and various beads or particles, including nanoparticles.

In certain embodiments, the MUC1 moiety can be attached to the support simply by electrostatic charges. In others, the support and/or MUC1 moiety is derivatized to permit covalent bonding of the two entities. In yet a third for, the MUC1 moiety is "linked" to the support through an intermediate agent, such as a linker, discussed below. In general, the principle behind all such attachments is to avoid disturbance of the MUC1 moiety's structure such that at least one relevant property (e.g., dimerization) retains intact.

E. Linkers

Linkers or cross-linking agents may be used to fuse MUC1 peptides to supports. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

F. Design, Variants and Analogs

In one aspect, the present invention focuses on peptides comprising the sequence CQCRRK. Having identified this key structure in MUC1 oligomer formation, the inventors also contemplate that variants of the CQCRRK sequence may be employed. For example, certain non-natural amino acids that satisfy the structural constraints of the CQCRRK sequence may be substituted without a loss, and perhaps with an improvement in, biological function. In addition, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993).

The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the invention also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention (e.g., Cohen et al., 1990; Navia et al., 1992), the disclosures of which are incorporated herein by reference in their entirety). All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy.

G. Assay Formats

A variety of different assay formats are contemplated in accordance with the present invention. Exemplary but non-limiting formats are discussed in the following paragraphs.

Plate- and Bead-Based MUC1-CD Dimerization Inhibition Assay for Primary Screening.

As discussed, the MUC1-CD CQC motif is necessary for the formation of dimers or oligomers. To develop a HTS assay for compounds that inhibit MUC1-CD dimerization, the inventors have generated purified His-tagged MUC1-CD, which can then be further labeled with biotin using a standard biotinylation kit. Biotinylated and non-biotinylated proteins are purified through Ni columns.

Multi-well (96- or 384-well) plates are coated with non-biotinylated MUC1-CD, and biotinylated MUC1-CD is added to the plates to initiate MUC1-CD dimerization or oligomerization. A luminescent substrate for biotin binding is added to the plate, followed by washing. Resulting fluorescence is detected by luminescence detection at absorbance 405 nM. A complete schematic illustration of this assay is described in FIG. 1. Test compounds are added at multiple concentrations to the plates and, following incubation and washing, the plates are read for luminescent detection. The formation of MUC1-CD dimers is detected.

A similar approach can be used but, instead of having MUC1-CD bound to a plate, the MUC1-CD is attached to the surface of a bead or "nanoparticle."

In-Gel In Vitro MUC1-CD Dimerization Assay.

Purified His-tagged MUC1-CD protein also forms dimers and oligomers when incubated in a buffer in vitro, and these can be detected by electrophoresis in polyacrylamide gels. Selected compounds from primary screening assays are incubated with purified His-tagged MUC1-CD protein for 60 min at room temperature. Following extensive washings, the proteins are separated in a non-reducing SDS-polyacrylamide gel and analyzed by immunoblotting with anti-MUC1-CD antibody.

As a positive control for validation of this assay for secondary screening, purified His-MUC1-CD is incubated with either PBS or with GO-201 (CQC peptide) for 1 hr at room temperature. The proteins are separated in a non-reducing SDS-polyacrylamide gel and analyzed by immunoblotting with anti-MUC1-CD antibody. Purified His-tagged MUC1-CD forms oligomers are detected by electrophoresis, and incubation of His-tagged MUC1-CD protein with GO-201 substantially decreases oligomer formation with a significant increase in monomer (FIG. 2).

Inhibition of Dimerization of MUC1-CD in Cyto.

Two different versions of MUC1-CD vectors have been generated for transformation of cells: GFP-MUC1-CD and Flag-MUC1-CD. HEK 293 cells, which do not express endogenous MUC1, can be transiently transfected to express an empty vector, GFP-MUC1-CD and/or Flag-MUC1-CD. At 48 hr post-transfection, cells are incubated with the selected compounds from the primary and/or secondary screening assays. Cells are then harvested and used for immunoblotting with anti-MUC1-C. Total cell lysates are subjected to immunoprecipitation with anti-GFP antibody and the adsorbates are analyzed by immunoblotting with anti-Flag antibody.

As a positive control for the validation of this assay, HEK 293 cells are transfected with vectors expressing GFP-MUC1-CD and Flag-MUC1-CD. Complexes of GFP-MUC1-CD and Flag-MUC1-CD are detectable by coprecipitation of lysates from cells not exposed to GO-201 peptide (FIG. 3). However, incubation of the transfected HEK 293 cells with 5 mM GO-201 is associated with the disruption of the interaction between Flag-MUC1-CD and GFP-MUC1-CD (FIG. 3). In addition, a control peptide, CP-1, has no apparent effect. Thus, a specific compound that will bind to MUC1-CD can inhibit formation of MUC1-CD oligomerization in cells, and therefore this assay can confirm the advancement of the selected compounds.

Assays for Detection of Endogenous MUC1 Expression in Human Breast Carcinoma Cells.

Western blot analysis for expression of MUC1 protein in MCF-7 cells can be used to test multiple concentrations of selected inhibitors daily for 6 days. Total cell lysates are then analysed by immunoblotting with ant-MUC1-C antibody to detect the protein levels. Also, a luciferase assay for transcriptional inhibition of MUC1 is used. A luciferase construct under the control of the MUC1 promoter has been placed into a pGL3 vector. As a validation of the assay, luciferase activity from MCF-7 cells with integrated MUC1 or pGL3 vector promoter reporter is shown in FIG. 4. These cells are treated with different concentrations of the selected inhibitors, and luciferase activity is measured by standard protocol.

III. SMALL MOLECULE INHIBITORS OF MUC1 OLIGOMERIZATION AND FUNCTION

A. MUC1 Inhibitory Flavones

Flavones are a class of flavonoids based on the backbone of 2-phenylchromen-4-one (2-phenyl-1-benzopyran-4-one). Natural flavones include Apigenin (4',5,7-trihydroxyflavone), Luteolin (3',4',5,7-tetrahydroxyflavone) and Tangeritin (4',5,6,7,8-pentamethoxyflavone), chrysin (5,7-OH), 6-hydroxyflavone, baicalein (5,6,7-trihydroxyflavone), scutellarein (5,6,7,4'-tetrahydroxyflavone), wogonin (5,7-OH, 8-$OCH_3$). Synthetic flavones are Diosmin and Flavoxate.

Flavones are mainly found in cereals and herbs. In the West, the estimated daily intake of flavones is in the range 20-50 mg per day. In recent years, scientific and public interest in flavones has grown enormously due to their putative beneficial effects against atherosclerosis, osteoporosis, diabetes mellitus and certain cancers. Flavones intake in the form of dietary supplements and plant extracts has been steadily increasing. Flavones have effects on CYP (P450) activity which are enzymes that metabolize most drugs in the body.

Apigenin is a flavone that is the aglycone of several glycosides. It is a yellow crystalline solid that has been used to dye wool. Apigenin is a potent inhibitor of CYP2C9, an enzyme responsible for the metabolism of many pharmaceutical drugs in the body. Apigenin (4',5,7-trihydroxyflavone) is commonly recognized as to mediated at least part of this chemopreventive action of vegetables and fruits in the cancerous process. Recently it was shown that Apigenin induces a process called autophagy (a kind of cellular dormancy) which may well explain it chemopreventive properties but at the same time induces resistance against chemotherapy.

Apigenin also has been shown to reverse the adverse effects of cyclosporine. Research has been conducted to study the effects of apigenin on reversal of cyclosporine A induced damage, and this was assessed by immunohistochemical estimation of expression of bcl-2, and estimation of apoptosis in histopathological sections. Cyclosporine A enhances the expression of transforming growth factor-β in the rat kidney, which signifies accelerated apoptosis. Therefore, transforming growth factor-β and apoptotic index may be used to assess apigenin and its effect on cyclosporine A induced renal damage.

PD98059.

2-(2'-amino-3'-methoxyphenyl)-oxanaphthalen-4-one, or PD98059, is a flavonoid and a potent inhibitor of mitogen-activated protein kinase kinase (MEK). Addition of PD98059 to rat liver cytosol just before the addition of TCDD suppressed TCDD binding and aryl hydrocarbon receptor (AHR) transformation, as measured by sucrose gradient centrifugation and electrophoretic mobility shift assays. These results suggest that PD98059 is a ligand for the AHR and functions as an AHR antagonist at concentrations commonly used to inhibit MEK and signaling processes that entail MEK activation.

Kaempferol.

Kaempferol is a natural flavonoid that has been isolated from tea, broccoli, Delphinium, Witch-hazel, grapefruit, brussel sprouts, apples and other plant sources. Kaempferol is a yellow crystalline solid with a melting point of 276-278° C. It is slightly soluble in water but soluble in hot ethanol and diethyl ether. Many glycosides of kaempferol, such as kaempferitrin and astragalin, have been isolated as natural products from plants. Kaempferol consumption in tea and broccoli has been associated with reduced risk of heart disease and has antidepressant properties. An 8-year study found that three flavonols (kaempferol, quercetin, and myricetin) reduced the risk of pancreatic cancer by 23%.

Fisetin.

Fisetin, an analogue of quercetin, is a brown pigment found in woody plants. It has antioxidant properties which protect cells against oxygen radical damage. It is also reported to inhibit xanthine oxidase, a free-radical generating enzyme and show and inhibit the oxidation of LDL (low density lipoprotein) by free radicals.

Morin.

Morin (3,5,7,2',4'-pentahydroxyflavone) is a flavonoid yellow color substance that can be isolated from *Maclura pomifera* (Osage orange), *Maclura tinctoria* (old fustic) and from leaves of *Psidium guajava* (common guava). It is an important bioactive compound interacting with nucleic acids, enzymes and protein. Oral administration offers protection against hyperammonemia by means of reducing blood ammonia, oxidative stress and enhancing antioxidant status in ammonium chloride-induced hyperammonemic rats. Enhanced blood ammonia, plasma urea, lipid peroxidation in circulation and tissues (liver and brain) of ammonium chloride-treated rats was accompanied by a significant decrease in the tissues levels of superoxide dismutase (SOD), catalase, reduced glutathione (GSH) and glutathione peroxidase (GPx). Morin administered to rats showed a significant reduction in ammonia, urea, lipid peroxidation with a simultaneous elevation in antioxidant levels.

Other Flavones.

The general structure below provides additional/similar flavone structures for use in accordance with the present invention:

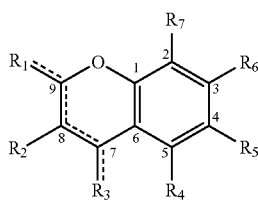

wherein
- R₁ is H, —OH, =O, substituted or unsubstituted alkyl (C$_{1-8}$), alkoxy(C$_{1-8}$), haloalkyl(C$_{1-8}$), substituted phenyl or unsubstituted phenyl, wherein if R₁ is =O, C₇-C₈ is a double bond;
- R₂ is H, —OH, alkyl(C$_{1-8}$), substituted phenyl, unsubstituted phenyl, phenyl, phenyl thiazole, imidazole, pyrazole or furan;
- R₃ is H, —OH, =O, halogen, haloalkyl(C$_{1-8}$), substituted or unsubstituted alkyl(C$_{1-8}$), substituted phenyl or unsubstituted phenyl, wherein if R₃ is =O, C₈-C₉ is a double bond;
- R₄ is H or —OH;
- R₅ is H, —OH, substituted or unsubstituted alkyl(C$_{1-8}$) or alkoxy(C$_{1-8}$), or OR₈, wherein R₈ is alkyl(C$_{1-8}$), an ester or an amide;
- R₆ is H, —OH, substituted or unsubstituted alkyl(C$_{1-8}$) or alkoxy(C$_{1-8}$), or OR₈, wherein R₈ is alkyl(C$_{1-8}$), an ester or an amide; and
- R₇ is H, —OH, or substituted or unsubstituted alkyl(C$_{1-8}$), with the proviso that R₁ and R₃ cannot both be =O.

B. Chemical Group Definitions

When used in the context of a chemical group, "hydrogen" means —H; "hydroxy" means —OH; "oxo" means =O; "halo" means independently —F, —Cl, —Br or —I; "amino" means —NH₂ (see below for definitions of groups containing the term amino, e.g., alkylamino); "hydroxyamino" means —NHOH; "nitro" means —NO₂; imino means =NH (see below for definitions of groups containing the term imino, e.g., alkylimino); "cyano" means —CN; "azido" means —N₃; in a monovalent context "phosphate" means —OP(O)(OH)₂ or a deprotonated form thereof; in a divalent context "phosphate" means —OP(O)(OH)O— or a deprotonated form thereof; "mercapto" means —SH; "thio" means =S; "thioether" means —S—; "sulfonamido" means —NHS(O)₂— (see below for definitions of groups containing the term sulfonamido, e.g., alkylsulfonamido); "sulfonyl" means —S(O)₂— (see below for definitions of groups containing the term sulfonyl, e.g., alkylsulfonyl); "sulfinyl" means —S(O)— (see below for definitions of groups containing the term sulfinyl, e.g., alkylsulfinyl); and "silyl" means —SiH₃ (see below for definitions of group(s) containing the term silyl, e.g., alkylsilyl).

The symbol "—" means a single bond, "=" means a double bond, and "≡" means triple bond. The symbol "----" represents a single bond or a double bond. The symbol "∼∼∼", when drawn perpendicularly across a bond indicates a point of attachment of the group. It is noted that the point of attachment is typically only identified in this manner for larger groups in order to assist the reader in rapidly and unambiguously identifying a point of attachment. The symbol "◂▬" means a single bond where the group attached to the thick end of the wedge is "out of the page." The symbol "▬▮▮▮" means a single bond where the group attached to the thick end of the wedge is "into the page". The symbol "∼∼∼" means a single bond where the conformation is unknown (e.g., either R or S), the geometry is unknown (e.g., either E or Z) or the compound is present as mixture of conformation or geometries (e.g., a 50%/50% mixture).

When a group "R" is depicted as a "floating group" on a ring system, for example, in the formula:

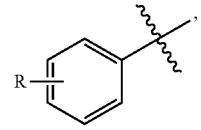

then R may replace any hydrogen atom attached to any of the ring atoms, including a depicted, implied, or expressly defined hydrogen, so long as a stable structure is formed.

When a group "R" is depicted as a "floating group" on a fused ring system, as for example in the formula:

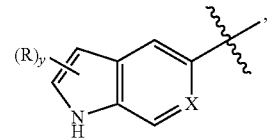

then R may replace any hydrogen attached to any of the ring atoms of either of the fuzed rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

When y is 2 and "(R)$_y$" is depicted as a floating group on a ring system having one or more ring atoms having two replaceable hydrogens, e.g., a saturated ring carbon, as for example in the formula:

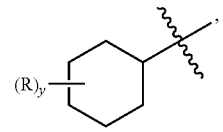

then each of the two R groups can reside on the same or a different ring atom. For example, when R is methyl and both R groups are attached to the same ring atom, a geminal dimethyl group results. Where specifically provided for, two R groups may be taken together to form a divalent group, such as one of the divalent groups further defined below. When such a divalent group is attached to the same ring atom, a spirocyclic ring structure will result.

When the point of attachment is depicted as "floating", for example, in the formula:

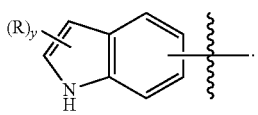

then the point of attachment may replace any replaceable hydrogen atom on any of the ring atoms of either of the fuzed rings unless specified otherwise.

In the case of a double-bonded R group (e.g., oxo, imino, thio, alkylidene, etc.), any pair of implicit or explicit hydrogen atoms attached to one ring atom can be replaced by the R group. This concept is exemplified below:

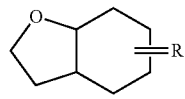

represents

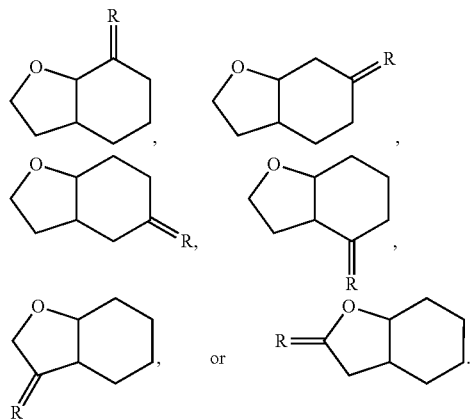

For the groups below, the following parenthetical subscripts further define the groups as follows: "(Cn)" defines the exact number (n) of carbon atoms in the group. "(C≤n)" defines the maximum number (n) of carbon atoms that can be in the group, with the minimum number of carbon atoms in such at least one, but otherwise as small as possible for the group in question, e.g., it is understood that the minimum number of carbon atoms in the group "alkenyl$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkanediyl" when used without the "substituted" modifier refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, CH$_2$C(CH$_3$)$_2$CH$_2$—, —CH$_2$CH$_2$CH$_2$, and

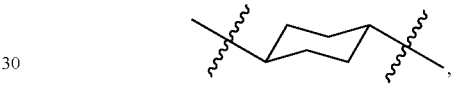

are non-limiting examples of alkanediyl groups. The term "substituted alkanediyl" refers to a non-aromatic monovalent group, wherein the alkylenediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH═CH$_2$ (vinyl), —CH═CHCH$_3$, —CH═CHCH$_2$CH$_3$, —CH$_2$CH═CH$_2$ (allyl), —CH$_2$CH═CHCH$_3$, and —CH═CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH═CHF, —CH═CHCl and —CH═CHBr, are non-limiting examples of substituted alkenyl groups.

The term "alkenediyl" when used without the "substituted" modifier refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH═CH—, —CH═C(CH₃)CH₂—, —CH═CHCH₂—, and

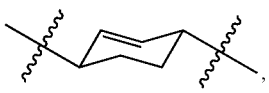 [SMILES: *C1C=CC(*)CC1]

are non-limiting examples of alkenediyl groups. The term "substituted alkenediyl" refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and at least one atom independently selected from the group consisting of N, O, F, Cl, Br, I, Si, P, and S. The following groups are non-limiting examples of substituted alkenediyl groups: —CF═CH—, —C(OH)═CH—, and —CH₂CH═C(Cl)—.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH₃, —C≡CC₆H₅ and —CH₂C≡CCH₃, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH₃)₃, is a non-limiting example of a substituted alkynyl group.

The term "alkynediyl" when used without the "substituted" modifier refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH₂—, and —C≡CCH(CH₃)— are non-limiting examples of alkynediyl groups. The term "substituted alkynediyl" refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and at least one atom independently selected from the group consisting of N, O, F, Cl, Br, I, Si, P, and S. The groups —C≡CCFH— and —C≡CHCH(Cl)— are non-limiting examples of substituted alkynediyl groups.

The term "aryl" when used without the "substituted" modifier refers to a monovalent group with an aromatic carbon atom as the point of attachment, said carbon atom forming part of one or more six-membered aromatic ring structure(s) wherein the ring atoms are all carbon, and wherein the monovalent group consists of no atoms other than carbon and hydrogen. Non-limiting examples of aryl groups include phenyl (Ph), methylphenyl, (dimethyl)phenyl, —C₆H₄—CH₂CH₃ (ethylphenyl), —C₆H₄—CH₂CH₂CH₃ (propylphenyl), —C₆H₄—CH(CH₃)₂, —C₆H₄—CH(CH₂)₂, —C₆H₃(CH₃)CH₂CH₃ (methylethylphenyl), —C₆H₄—CH═CH₂ (vinylphenyl), —C₆H₄—CH═CHCH₃, —C₆H₄C≡CH, naphthyl, and the monovalent group derived from biphenyl. The term "substituted aryl" refers to a monovalent group with an aromatic carbon atom as the point of attachment, said carbon atom forming part of one or more six-membered aromatic ring structure(s) wherein the ring atoms are all carbon, and wherein the monovalent group further has at least one atom independently selected from the group consisting of N, O, F, Cl, Br, I, Si, P, and S, Non-limiting examples of substituted aryl groups include the groups: —C₆H₄F, —C₆H₄Cl, —C₆H₄Br, —C₆H₄I, —C₆H₄OH, —C₆H₄OCH₃, —C₆H₄OCH₂CH₃, —C₆H₄OC(O)CH₃, C₆H₄NH₂, C₆H₄NHCH₃, —C₆H₄N(CH₃)₂, —C₆H₄—CH₂OH, —C₆H₄—CH₂OC(O)CH₃, —C₆H₄—CH₂NH₂, —C₆H₄CF₃, —C₆H₄CN, —C₆H₄—CHO, —C₆H₄—CHO, —C₆H₄C(O)CH₃, —C₆H₄C(O)C₆H₅, —C₆H₄CO₂H, —C₆H₄CO₂CH₃, —C₆H₄CONH₂, —C₆H₄CONHCH₃, and —C₆H₄CON(CH₃)₂.

The term "arenediyl" when used without the "substituted" modifier refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of arenediyl groups include:

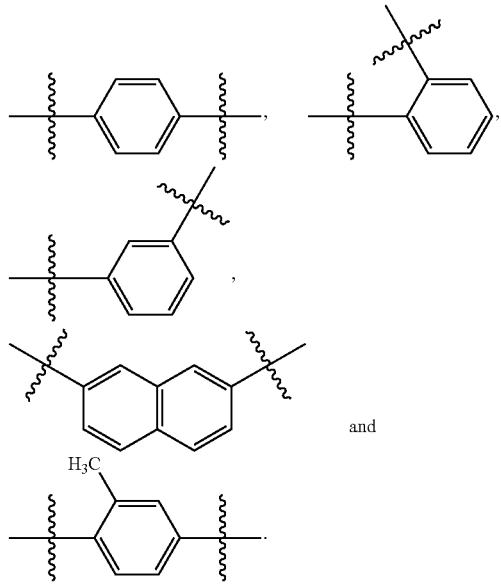

and

The term "substituted arenediyl" refers to a divalent group, wherein the arenediyl group is attached with two σ-bonds, with two aromatic carbon atoms as points of attachment, said carbon atoms forming part of one or more six-membered aromatic rings structure(s), wherein the ring atoms are carbon, and wherein the divalent group further has at least one atom independently selected from the group consisting of N, O, F, Cl, Br, I, Si, P, and S.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroarenediyl" when used without the "substituted" modifier refers to a divalent group, wherein the heteroarenediyl group is attached with two σ-bonds, with an aromatic carbon atom or nitrogen atom as the point of attachment, said carbon atom or nitrogen atom forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. Non-limiting examples of heteroarenediyl groups include:

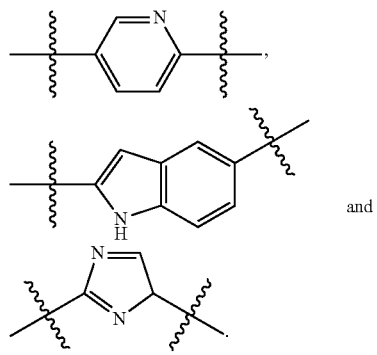

and

The term "substituted heteroarenediyl" refers to a divalent group, wherein the heteroarenediyl group is attached with two σ-bonds, with an aromatic carbon atom or nitrogen atom as points of attachment, said carbon atom or nitrogen atom forming part of one or more six-membered aromatic ring structure(s), wherein at least one of the ring atoms is nitrogen, oxygen or sulfur, and wherein the divalent group further has at least one atom independently selected from the group consisting of non-aromatic nitrogen, non-aromatic oxygen, non aromatic sulfur F, Cl, Br, I, Si, and P.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$—CH$_3$, —C(O)C$_6$H$_4$—CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H (carboxyl), —CO$_2$CH$_3$ (methylcarboxyl), —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups.

The term "alkylidene" when used without the "substituted" modifier refers to the divalent group =CRR', wherein the alkylidene group is attached with one σ-bond and one π-bond, in which R and R' are independently hydrogen, alkyl, or R and R' are taken together to represent alkanediyl. Non-limiting examples of alkylidene groups include: =CH$_2$, =CH(CH$_2$CH$_3$), and =C(CH$_3$)$_2$. The term "substituted alkylidene" refers to the group =CRR', wherein the alkylidene group is attached with one σ-bond and one π-bond, in which R and R' are independently hydrogen, alkyl, substituted alkyl, or R and R' are taken together to represent a substituted alkanediyl, provided that either one of R and R' is a substituted alkyl or R and R' are taken together to represent a substituted alkanediyl.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

Similarly, the terms "alkenyloxy", "alkynyloxy", "aryloxy", "aralkoxy", "heteroaryloxy", "heteroaralkoxy" and "acyloxy", when used without the "substituted" modifier, refers to groups, defined as —OR, in which R is alkenyl, alkynyl, aryl, aralkyl, heteroaryl, heteroaralkyl and acyl, respectively, as those terms are defined above. When any of the terms alkenyloxy, alkynyloxy, aryloxy, aralkyloxy and acyloxy is modified by "substituted," it refers to the group —OR, in which R is substituted alkenyl, alkynyl, aryl, aralkyl, heteroaryl, heteroaralkyl and acyl, respectively.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

The terms "alkoxyamino", "alkenylamino", "alkynylamino", "arylamino", "aralkylamino", "heteroarylamino", "heteroaralkylamino", and "alkylsulfonylamino" when used without the "substituted" modifier, refers to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$. When any of the terms alkoxyamino, alkenylamino, alkynylamino, arylamino, aralkylamino, heteroarylamino, heteroaralkylamino and alkylsulfonylamino is modified by "substituted," it refers to the group —NHR, in which R is substituted alkoxy, alkenyl, alkynyl, aryl, aralkyl, heteroaryl, heteroaralkyl and alkylsulfonyl, respectively.

The term "amido" (acylamino), when used without the "substituted" modifier, refers to the group —NHR, in which R is acyl, as that term is defined above. A non-limiting example of an acylamino group is —NHC(O)CH$_3$. When the term amido is used with the "substituted" modifier, it refers to groups, defined as —NHR, in which R is substituted acyl, as that term is defined above. The groups —NHC(O)OCH$_3$ and —NHC(O)NHCH$_3$ are non-limiting examples of substituted amido groups.

The term "alkylimino" when used without the "substituted" modifier refers to the group =NR, wherein the alkylimino group is attached with one σ-bond and one π-bond, in which R is an alkyl, as that term is defined above. Non-limiting examples of alkylimino groups include: =NCH$_3$, =NCH$_2$CH$_3$ and =N-cyclohexyl. The term "substituted alkylimino" refers to the group =NR, wherein the alkylimino group is attached with one σ-bond and one π-bond, in which R is a substituted alkyl, as that term is defined above. For example, =NCH$_2$CF$_3$ is a substituted alkylimino group.

Similarly, the terms "alkenylimino", "alkynylimino", "arylimino", "aralkylimino", "heteroarylimino", "heteroaralkylimino" and "acylimino", when used without the "substituted" modifier, refers to groups, defined as =NR, wherein the alkylimino group is attached with one σ-bond and one π-bond, in which R is alkenyl, alkynyl, aryl, aralkyl, heteroaryl, heteroaralkyl and acyl, respectively, as those terms are defined above. When any of the terms alkenylimino, alkynylimino, arylimino, aralkylimino and acylimino is modified by "substituted," it refers to the group =NR, wherein the alkylimino group is attached with one σ-bond and one π-bond, in which R is substituted alkenyl, alkynyl, aryl, aralkyl, heteroaryl, heteroaralkyl and acyl, respectively.

The term "fluoroalkyl" when used without the "substituted" modifier refers to an alkyl, as that term is defined above, in which one or more fluorines have been substituted for hydrogens. The groups, —CH$_2$F, —CF$_2$H, —CF$_3$, and —CH$_2$CF$_3$ are non-limiting examples of fluoroalkyl groups. The term "substituted fluoroalkyl" refers to a non-aromatic monovalent group with a saturated carbon atom as the point of attachment, a linear or branched, cyclo, cyclic or acyclic structure, at least one fluorine atom, no carbon-carbon double or triple bonds, and at least one atom independently selected from the group consisting of N, O, Cl, Br, I, Si, P, and S. The following group is a non-limiting example of a substituted fluoroalkyl: —CFHOH.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "substituted alkylphosphate" refers to the group —OP(O)(OH)(OR), in which R is a substituted alkyl, as that term is defined above.

The term "dialkylphosphate" when used without the "substituted" modifier refers to the group —OP(O)(OR)(OR'), in which R and R' can be the same or different alkyl groups, or R and R' can be taken together to represent an alkanediyl having two or more saturated carbon atoms, at least two of which are attached via the oxygen atoms to the phosphorus atom. Non-limiting examples of dialkylphosphate groups include: —OP(O)(OMe)$_2$, —OP(O)(OEt)(OMe) and —OP(O)(OEt)$_2$. The term "substituted dialkylphosphate" refers to the group —OP(O)(OR)(OR'), in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached via the oxygen atoms to the phosphorous.

The term "alkylthio" when used without the "substituted" modifier refers to the group —SR, in which R is an alkyl, as that term is defined above. Non-limiting examples of alkylthio groups include: —SCH$_3$, —SCH$_2$CH$_3$, —SCH$_2$CH$_2$CH$_3$, —SCH(CH$_3$)$_2$, —SCH(CH$_2$)$_2$, —S-cyclopentyl, and —S-cyclohexyl. The term "substituted alkylthio" refers to the group —SR, in which R is a substituted alkyl, as that term is defined above. For example, —SCH$_2$CF$_3$ is a substituted alkylthio group.

Similarly, the terms "alkenylthio", "alkynylthio", "arylthio", "aralkylthio", "heteroarylthio", "heteroaralkylthio", and "acylthio", when used without the "substituted" modifier, refers to groups, defined as —SR, in which R is alkenyl, alkynyl, aryl, aralkyl, heteroaryl, heteroaralkyl and acyl, respectively, as those terms are defined above. When any of the terms alkenylthio, alkynylthio, arylthio, aralkylthio, heteroarylthio, heteroaralkylthio, and acylthio is modified by "substituted," it refers to the group —SR, in which R is substituted alkenyl, alkynyl, aryl, aralkyl, heteroaryl, heteroaralkyl and acyl, respectively.

The term "thioacyl" when used without the "substituted" modifier refers to a monovalent group with a carbon atom of a thiocarbonyl group as the point of attachment, further having a linear or branched, cyclo, cyclic or acyclic structure, further having no additional atoms that are not carbon or hydrogen, beyond the sulfur atom of the carbonyl group. The groups, —CHS, —C(S)CH$_3$, —C(S)CH$_2$CH$_3$, —C(S)CH$_2$CH$_2$CH$_3$, —C(S)CH(CH$_3$)$_2$, —C(S)CH(CH$_2$)$_2$, —C(S)C$_6$H$_5$, —C(S)C$_6$H$_4$C$_{1-13}$, —C(S)C$_6$H$_4$—CH$_2$CH$_3$, —C(S)C$_6$H$_3$(CH$_3$)$_2$, and —C(S)CH$_2$C$_6$H$_5$, are non-limiting examples of thioacyl groups. The term "thioacyl" therefore encompasses, but is not limited to, groups sometimes referred to as "alkyl thiocarbonyl" and "aryl thiocarbonyl" groups. The term "substituted thioacyl" refers to a radical with a carbon atom as the point of attachment, the carbon atom being part of a thiocarbonyl group, further having a linear or branched, cyclo, cyclic or acyclic structure, further having at least one atom, in addition to the sulfur atom of the carbonyl group, independently selected from the group consisting of N, O, F, Cl, Br, I, Si, P, and S. The groups, —C(S)CH$_2$CF$_3$, —C(S)O$_2$H, —C(S)OCH$_3$, —C(S)OCH$_2$CH$_3$, —C(S)OCH$_2$CH$_2$CH$_3$, —C(S)OC$_6$H$_5$, —C(S)OCH(CH$_3$)$_2$, —C(S)OCH(CH$_2$)$_2$, —C(S)NH$_2$, and —C(S)NHCH$_3$, are non-limiting examples of substituted thioacyl groups. The term "substituted thioacyl" encompasses, but is not limited to, "heteroaryl thiocarbonyl" groups.

The term "alkylsulfonyl" when used without the "substituted" modifier refers to the group —S(O)$_2$R, in which R is an alkyl, as that term is defined above. Non-limiting examples of alkylsulfonyl groups include: —S(O)$_2$CH$_3$, —S(O)$_2$CH$_2$CH$_3$, —S(O)$_2$CH$_2$CH$_2$CH$_3$, —S(O)$_2$CH(CH$_3$)$_2$, —S(O)$_2$CH(CH$_2$)$_2$, —S(O)$_2$ cyclopentyl, and —S(O)$_2$-cyclohexyl. The term "substituted alkylsulfonyl" refers to the group —S(O)$_2$R, in which R is a substituted alkyl, as that term is defined above. For example, —S(O)$_2$CH$_2$CF$_3$ is a substituted alkylsulfonyl group.

Similarly, the terms "alkenylsulfonyl", "alkynylsulfonyl", "arylsulfonyl", "aralkylsulfonyl", "heteroarylsulfonyl", and "heteroaralkylsulfonyl" when used without the "substituted" modifier, refers to groups, defined as —S(O)$_2$R, in which R is alkenyl, alkynyl, aryl, aralkyl, heteroaryl, and heteroaralkyl, respectively, as those terms are defined above. When any of the terms alkenylsulfonyl, alkynylsulfonyl, arylsulfonyl, aralkylsulfonyl, heteroarylsulfonyl, and heteroaralkylsulfonyl is modified by "substituted," it refers to the group —S(O)$_2$R, in which R is substituted alkenyl, alkynyl, aryl, aralkyl, heteroaryl and heteroaralkyl, respectively.

The term "alkylsulfinyl" when used without the "substituted" modifier refers to the group —S(O)R, in which R is an alkyl, as that term is defined above. Non-limiting examples of alkylsulfinyl groups include: —S(O)CH$_3$, —S(O)CH$_2$CH$_3$, —S(O)CH$_2$CH$_2$CH$_3$, —S(O)CH(CH$_3$)$_2$, —S(O)CH(CH$_2$)$_2$, —S(O)-cyclopentyl, and —S(O)-cyclohexyl. The term "substituted alkylsulfinyl" refers to the group —S(O)R, in which R is a substituted alkyl, as that term is defined above. For example, —S(O)CH$_2$CF$_3$ is a substituted alkylsulfinyl group.

Similarly, the terms "alkenylsulfinyl", "alkynylsulfinyl", "arylsulfinyl", "aralkylsulfinyl", "heteroarylsulfinyl", and "heteroaralkylsulfinyl" when used without the "substituted" modifier, refers to groups, defined as —S(O)R, in which R is alkenyl, alkynyl, aryl, aralkyl, heteroaryl, and heteroaralkyl, respectively, as those terms are defined above. When any of the terms alkenylsulfinyl, alkynylsulfinyl, arylsulfinyl, aralkylsulfinyl, heteroarylsulfinyl, and heteroaralkylsulfinyl is modified by "substituted," it refers to the group —S(O)R, in which R is substituted alkenyl, alkynyl, aryl, aralkyl, heteroaryl and heteroaralkyl, respectively.

The term "alkylammonium" when used without the "substituted" modifier refers to a group, defined as —NH$_3$R$^+$, —NHRR'$^+$, or —NRR'R''$^+$, in which R, R' and R'' are the same or different alkyl groups, or any combination of two of R, R' and R'' can be taken together to represent an alkanediyl. Non-limiting examples of alkylammonium cation groups include: —NH$_2$(CH$_3$)$^+$, —NH$_2$(CH$_2$CH$_3$)$^+$, —NH$_2$(CH$_2$CH$_2$CH$_3$)$^+$, —NH(CH$_3$)$_2$$^+$, —NH(CH$_2$CH$_3$)$_2$$^+$, —NH(CH$_2$CH$_2$CH$_3$)$_2$$^+$, —N(CH$_3$)$_3$$^+$, —N(CH$_3$)(CH$_2$CH$_3$)$_2$$^+$, —N(CH$_3$)$_2$(CH$_2$CH$_3$)$^+$, —NH$_2$C(CH$_3$)$_3$$^+$, —NH(cyclopentyl)$_2$$^+$, and —NH$_2$(cyclohexyl)$^+$. The term "substituted alkylammonium" refers —NH$_3$R$^+$, —NHRR'$^+$, or —NRR'R''$^+$, in which at least one of R, R' and R'' is a substituted alkyl or two of R, R' and R'' can be taken together to represent a substituted alkanediyl. When more than one of R, R' and R'' is a substituted alkyl, they can be the same of different. Any of R, R' and R'' that are not either substituted alkyl or substituted alkanediyl, can be either alkyl, either the same or different, or can be taken together to represent a alkanediyl with two or more carbon atoms, at least two of which are attached to the nitrogen atom shown in the formula.

The term "alkylsulfonium" when used without the "substituted" modifier refers to the group —SRR'$^+$, in which R and R' can be the same or different alkyl groups, or R and R' can be taken together to represent an alkanediyl. Non-limiting examples of alkylsulfonium groups include: —SH(CH$_3$)$^+$, —SH(CH$_2$CH$_3$)$^+$, —SH(CH$_2$CH$_2$CH$_3$)$^+$, —S(CH$_3$)$_2$$^+$, —S(CH$_2$CH$_3$)$_2$$^+$, —S(CH$_2$CH$_2$CH$_3$)$_2$$^+$, —SH(cyclopentyl)$^+$, and —SH(cyclohexyl)$^+$. The term "substituted alkylsulfonium" refers to the group —SRR'$^+$, in which R and R' can be the same or different substituted alkyl groups, one of R or R' is an alkyl and the other is a substituted alkyl, or R and R' can be taken together to represent a substituted alkanediyl. For example, —SH(CH$_2$CF$_3$)$^+$ is a substituted alkylsulfonium group.

The term "alkylsilyl" when used without the "substituted" modifier refers to a monovalent group, defined as —SiH$_2$R, —SiHRR', or —SiRR'R'', in which R, R' and R'' can be the same or different alkyl groups, or any combination of two of R, R' and R'' can be taken together to represent an alkanediyl. The groups, —SiH$_2$CH$_3$, —SiH(CH$_3$)$_2$, —Si(CH$_3$)$_3$ and —Si(CH$_3$)$_2$C(CH$_3$)$_3$, are non-limiting examples of unsubstituted alkylsilyl groups. The term "substituted alkylsilyl" refers to —SiH$_2$R, —SiHRR', or —SiRR'R'', in which at least one of R, R' and R'' is a substituted alkyl or two of R, R' and R'' can be taken together to represent a substituted alkanediyl. When more than one of R, R' and R'' is a substituted alkyl, they can be the same of different. Any of R, R' and R'' that are not either substituted alkyl or substituted alkanediyl, can be either alkyl, either the same or different, or can be taken together to represent a alkanediyl with two or more saturated carbon atoms, at least two of which are attached to the silicon atom.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

A compound having a formula that is represented with a dashed bond is intended to include the formulae optionally having zero, one or more double bonds. Thus, for example, the structure

includes the structures

, , ,  and

.

As will be understood by a person of skill in the art, no one such ring atom forms part of more than one double bond.

Any undefined valency on an atom of a structure shown in this application implicitly represents a hydrogen atom bonded to the atom.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties*, and Use (P. H. Stahl & C. G. Wermuth eds., Verlag Helvetica Chimica Acta, 2002), As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methane-sulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—$CH_2CH_2$—]$_n$—, the repeat unit is —$CH_2CH_2$—. The subscript "n" denotes the degree of polymerisation, that is, the number of repeat units linked together. When the value for "n" is left undefined, it simply designates repetition of the formula within the brackets as well as the polymeric nature of the material. The concept of a repeat unit applies equally to where the connectivity between the repeat units extends three dimensionally, such as in metal organic frameworks, cross-linked polymers, thermosetting polymers, etc.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

The invention contemplates that for any stereocenter or axis of chirality for which stereochemistry has not been defined, that stereocenter or axis of chirality can be present in its R form, S form, or as a mixture of the R and S forms, including racemic and non-racemic mixtures.

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—$C(O)OC(CH_3)_3$), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), tert-butoxycarbonyl groups (—$C(O)OC(CH_3)_3$), and the like. Suitable peptide residues include peptide residues comprising two to five, and optionally amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), tert-butoxycarbonyl groups (—$C(O)OC(CH_3)_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxybenzyloxycarbonyl); and haloethoxycarbonyl groups (such as β,β,β-trichloroethoxycarbonyl and β-iodoethoxycarbonyl).

"Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the term "water soluble" means that the compound dissolves in water at least to the extent of 0.010 mole/liter or is classified as soluble according to literature precedence.

Other abbreviations used herein are as follows: DMSO, dimethyl sulfoxide; NO, nitric oxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFNγ or IFN-γ, interferon-γ; LPS, bacterial endotoxic lipopolysaccharide; TNFα or TNF-α, tumor necrosis factor-α; IL-1β, interleukin-1β; GAPDH, glyceraldehyde-3-phosphate dehydrogenase; MTT, 3-[4,5-dimethylthiazol-2-yl]-2,5-diphenyltetrazolium bromide; TCA, trichloroacetic acid; HO-1, inducible heme oxygenase.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

C. Synthesis

Several methods exist for the synthesis of flavones, including the Allan-Robinson reaction, the Auwers synthesis, the Baker-Venkataraman rearrangement, the Algar-Flynn-Oyamada reaction, the Wessely-Moser rearrangement (Wessely & Moser, 1930), and the dehydrative cyclization of certain 1,3-diaryl diketones (Sarda et al., 2006).

IV. THERAPIES

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render agents stable and allow for uptake by target cells. Aqueous compositions of the present invention comprise an effective amount of the compounds, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Inflammatory Disease States and Conditions i. Sepsis

Sepsis is a serious medical condition characterized by a whole-body inflammatory state caused by infection. Traditionally the term sepsis has been used interchangeably with septicaemia and septicemia ("blood poisoning"). However, these terms are no longer considered synonymous; septicemia is considered a subset of sepsis.

Symptoms of sepsis are often related to the underlying infectious process. When the infection crosses into sepsis, the resulting symptoms are that of systemic inflammatory response syndrome (SIRS): general inflammation, fever, elevated white blood cell count (leukocytosis), and raised heart rate (tachycardia) and breathing rate (tachypnea). Secondary to the above, symptoms also include flu like chills.

The immunological response that causes sepsis is a systemic inflammatory response causing widespread activation of inflammation and coagulation pathways. This may progress to dysfunction of the circulatory system and, even under optimal treatment, may result in the multiple organ dysfunction syndrome and eventually death.

Sepsis is considered present if infection is highly suspected or proven and two or more of the following systemic inflammatory response syndrome (SIRS) criteria are met:

heart rate >90 beats per minute
body temperature <36 (96.8° F.) or >38° C. (100.4° F.)
hyperventilation (high respiratory rate) >20 breaths per minute or, on blood gas, a $P_aCO_2$ less than 32 mm Hg
white blood cell count <4000 cells/mm$^3$ or >12000 cells/mm$^3$ (<4×10$^9$ or >12×10$^9$ cells/L), or greater than 10% band forms (immature white blood cells).

Consensus definitions however continue to evolve with the latest expanding the list of signs and symptoms of sepsis to reflect clinical bedside experience.

The more critical subsets of sepsis are severe sepsis (sepsis with acute organ dysfunction) and septic shock (sepsis with refractory arterial hypotension). Alternatively, when two or more of the systemic inflammatory response syndrome criteria are met without evidence of infection, patients may be diagnosed simply with "SIRS." Patients with SIRS and acute organ dysfunction may be termed "severe SIRS."

Patients are defined as having "severe sepsis" if they have sepsis plus signs of systemic hypoperfusion; either end organ dysfunction or a serum lactate greater than 4 mmol/dL. Patient are defined as having septic shock if they have sepsis plus hypotension after an appropriate fluid bolus (typically 20 ml/kg of crystalloid). The criteria for diagnosing an adult with sepsis do not apply to infants under one month of age. In infants, only the presence of infection plus a "constellation" of signs and symptoms consistent with the systemic response to infection are required for diagnosis.

The therapy of sepsis rests on antibiotics, surgical drainage of infected fluid collections, fluid replacement and appropriate support for organ dysfunction. This may include hemodialysis in kidney failure, mechanical ventilation in pulmonary dysfunction, transfusion of blood products, and drug and fluid therapy for circulatory failure. Ensuring adequate nutrition, if necessary by parenteral nutrition, is important during prolonged illness.

A problem in the adequate management of septic patients has been the delay in administering therapy after sepsis has been recognized. Published studies have demonstrated that for every hour delay in the administration of appropriate antibiotic therapy there is an associated 7% rise in mortality. A large international collaboration was established to educate people about sepsis and to improve patient outcomes with sepsis, entitled the "Surviving Sepsis Campaign." The Campaign has published an evidence-based review of management strategies for severe sepsis, with the aim to publish a complete set of guidelines in subsequent years.

Most therapies aimed at the inflammatory process itself have failed to improve outcome, however drotrecogin alfa (activated protein C, one of the coagulation factors) has been shown to decrease mortality from about 31% to about 25% in severe sepsis. To qualify for drotrecogin alfa, a patient must have severe sepsis or septic shock with an APACHE II score of 25 or greater and a low risk of bleeding. Low dose hydrocortisone treatment has shown promise for septic shock patients with relative adrenal insufficiency as defined by ACTH stimulation testing.

Standard treatment of infants with suspected sepsis consists of supportive care, maintaining fluid status with intravenous fluids, and the combination of a β-lactam antibiotic (such as ampicillin) with an aminoglycoside such as gentamicin.

ii. Trauma

Physical trauma is a serious and body-altering physical injury, such as the removal of a limb. Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to subsequent infection, including sepsis. The present invention provides to treatment of trauma, including both pre-treatment (in the case of a medical procedure) and treatment after trauma injury as occurred.

Surgery.

Surgery uses operative manual and instrumental techniques on a patient to investigate and/or treat a pathological condition such as disease or injury, to help improve bodily function or appearance, or sometimes for some other reason. The present invention can address trauma resulting from surgeries, as defined further below.

As a general rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anesthesia, antiseptic conditions, typical surgical instruments, and suturing or stapling. All forms of surgery are considered invasive procedures; so-called noninvasive surgery usually refers to an excision that does not penetrate the structure being addressed (e.g., laser ablation of the cornea) or to a radiosurgical procedure (e.g., irradiation of a tumor). Surgery can last from minutes to hours.

Surgical procedures are commonly categorized by urgency, type of procedure, body system involved, degree of invasiveness, and special instrumentation. Elective surgery is done to correct a non-life-threatening condition, and is carried out at the patient's request, subject to the surgeon's and the surgical facility's availability. Emergency surgery is surgery which must be done quickly to save life, limb, or functional capacity. Exploratory surgery is performed to aid or confirm a diagnosis. Therapeutic surgery treats a previously diagnosed condition.

Amputation involves cutting off a body part, usually a limb or digit. Replantation involves reattaching a severed body part. Reconstructive surgery involves reconstruction of an injured, mutilated, or deformed part of the body. Cosmetic surgery is done to improve the appearance of an otherwise normal structure. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

When surgery is performed on one organ system or structure, it may be classed by the organ, organ system or tissue involved. Examples include cardiac surgery (performed on the heart), gastrointestinal surgery (performed within the digestive tract and its accessory organs), and orthopedic surgery (performed on bones and/or muscles).

Minimally invasive surgery involves smaller outer incision(s) to insert miniaturized instruments within a body cavity or structure, as in laparoscopic surgery or angioplasty. By contrast, an open surgical procedure requires a large incision to access the area of interest. Laser surgery involves use of a laser for cutting tissue instead of a scalpel or similar surgical instruments. Microsurgery involves the use of an operating microscope for the surgeon to see small structures. Robotic surgery makes use of a surgical robot, such as Da Vinci or Zeus surgical systems, to control the instrumentation under the direction of the surgeon.

Traumatic Hemorrhage.

Traumatic hemorrhage accounts for much of the wide ranging international impact of injury, causing a large proportion of deaths and creating great morbidity in the injured. Despite differences in pre-hospital care, the acute management of traumatic hemorrhage is similar around the world and follows well accepted published guidelines. A critically injured patient's care occurs as four, often overlapping segments: the resuscitative, operative, and critical care phases. The diagnosis and control of bleeding should be a high priority during all of the phases of trauma care and is especially important in the patient who is in hemorrhagic shock. Early attempts at hemorrhage control include direct control of visible sources of severe bleeding with direct pressure, pressure dressings, or tourniquets; stabilization of long bone and pelvic fractures; and keeping the patient warm. During the resuscitative phase, warmed intravenous fluids, hypotensive resuscitation prior to surgical control of hemorrhage, and appropriate transfusion of blood and blood products are provided. In the operative phase, surgical control of the hemorrhage and any other injury, and additional transfusion is provide. Finally, the critical care phase provides for postoperative support and tissue perfusion.

iii. Acute Pancreatitis

Acute pancreatitis is rapidly-onset inflammation of the pancreas. Depending on its severity, it can have severe complications and high mortality despite treatment. While mild cases are often successfully treated with conservative measures or laparoscopy, severe cases require invasive surgery (often more than one intervention) to contain the disease process.

iv. Acute Respiratory Distress Syndrome

Acute respiratory distress syndrome (ARDS), also known as respiratory distress syndrome (RDS) or adult respiratory distress syndrome (in contrast with IRDS) is a serious reaction to various forms of injuries to the lung. This is the most important disorder resulting in increased permeability pulmonary edema.

ARDS is a severe lung disease caused by a variety of direct and indirect insults. It is characterized by inflammation of the lung parenchyma leading to impaired gas exchange with concomitant systemic release of inflammatory mediators causing inflammation, hypoxemia and frequently resulting in multiple organ failure. This condition is life threatening and often lethal, usually requiring mechanical ventilation and admission to an intensive care unit. A less severe form is called acute lung injury (ALI).

ARDS can occur within 24 to 48 hours of an injury or attack of acute illness. In such a case the patient usually presents with shortness of breath, tachypnea, and symptoms related to the underlying cause, i.e., shock. Long term illnesses can also trigger it, such as malaria. The ARDS may then occur sometime after the onset of a particularly acute case of the infection.

An arterial blood gas analysis and chest X-ray allow formal diagnosis by inference using the aforementioned criteria. Although severe hypoxemia is generally included, the appropriate threshold defining abnormal $PaO_2$ has never been systematically studied. Any cardiogenic cause of pulmonary edema should be excluded. This can be done by placing a pulmonary artery catheter for measuring the pulmonary artery wedge pressure. However, this is not necessary and is now rarely done as abundant evidence has emerged demonstrating that the use of pulmonary artery catheters does not lead to improved patient outcomes in critical illness including ARDS. Plain chest X-rays are sufficient to document bilateral alveolar infiltrates in the majority of cases. While CT scanning leads to more accurate images of the pulmonary parenchyma in ARDS, its has little utility in the clinical management of patients with ARDS, and remains largely a research tool.

Acute respiratory distress syndrome is usually treated with mechanical ventilation in the Intensive Care Unit. Ventilation is usually delivered through oro-tracheal intubation, or tracheostomy whenever prolonged ventilation ($\geq 2$ weeks) is deemed inevitable. The possibilities of non-invasive ventilation are limited to the very early period of the disease or, better, to prevention in individuals at risk for the development of the disease (atypical pneumonias, pulmonary contusion, major surgery patients). Treatment of the underlying cause is imperative, as it tends to maintain the ARDS picture. Appropriate antibiotic therapy must be administered as soon as microbiological culture results are available. Empirical therapy may be appropriate if local microbiological surveillance is efficient. More than 60% ARDS patients experience a (nosocomial) pulmonary infection either before or after the onset of lung injury. The origin of infection, when surgically treatable, must be operated on. When sepsis is diagnosed, appropriate local protocols should be enacted.

v. Ischemia-Reperfusion Injury

Reperfusion injury refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

The damage of reperfusion injury is due in part to the inflammatory response of damaged tissues. White blood cells carried to the area by the newly returning blood release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. Leukocytes may also build up in small capillaries, obstructing them and leading to more ischemia.

Reperfusion injury plays a part in the brain's ischemic cascade, which is involved in stroke and brain trauma. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

In prolonged ischemia (60 min or more), hypoxanthine is formed as breakdown product of ATP metabolism. The enzyme xanthine dehydrogenase is converted to xanthine oxidase as a result of the higher availability of oxygen. This oxidation results in molecular oxygen being converted into highly reactive superoxide and hydroxyl radicals. Xanthine oxidase also produces uric acid, which may act as both a prooxidant and as a scavenger of reactive species such as peroxinitrite. Excessive nitric oxide produced during reperfusion reacts with superoxide to produce the potent reactive species peroxynitrite. Such radicals and reactive oxygen species attack cell membrane lipids, proteins, and glycosaminoglycans, causing further damage. They may also initiate specific biological processes by redox signaling.

vi. Cardiovascular Disease

Cardiovascular disease refers to the class of diseases that involve the heart or blood vessels (arteries and veins). While the term technically refers to any disease that affects the cardiovascular system, it is usually used to refer to those related to atherosclerosis (arterial disease). These conditions have similar causes, mechanisms, and treatments. Treatment of cardiovascular disease depends on the specific form of the disease in each patient, but effective treatment always includes preventive lifestyle changes discussed above. Medications, such as blood pressure reducing medications, aspirin and the statin cholesterol-lowering drugs may be helpful. In some circumstances, surgery or angioplasty may be warranted to reopen, repair, or replace damaged blood vessels Most Western countries face high and increasing rates of cardiovascular disease. Each year, heart disease kills more Americans than cancer. Diseases of the heart alone caused 30% of all deaths, with other diseases of the cardiovascular system causing substantial further death and disability. Up until the year 2005, it was the number 1 cause of death and disability in the United States and most European countries. A large histological study (PDAY) showed vascular injury accumulates from adolescence, making primary prevention efforts necessary from childhood.

Some biomarkers are thought to offer a more detailed risk of cardiovascular disease. However, the clinical value of these biomarkers is questionable. Currently, biomarkers which may reflect a higher risk of cardiovascular disease include:

higher fibrinogen and PAI-1 blood concentrations
elevated homocysteine, or even upper half of normal
elevated blood levels of asymmetric dimethylarginine
high inflammation as measured by C-reactive protein
elevated blood levels of B-type natriuretic peptide (BNP)

Various forms of cardiovascular disease include aneurysms, angina, arrhythmia, atherosclerosis, cardiomyopathy, cerebrovascular disease, congenital heart disease, congestive heart failure, myocarditis, valve disease, coronary artery disease, dilated cardiomyopathy, diastolic dysfunction, endocarditis, high blood pressure (hypertension), hypertrophic cardiomyopathy, nitral valve prolapse, myocardial infarction, and venous thromboembolism.

vii. Autoimmune/Inflammatory Disease

The present invention contemplates the treatment of a variety of autoimmune and/or inflammatory disease states such as spondyloarthropathy, ankylosing spondylitis, psoriatic arthritis, reactive arthritis, enteropathic arthritis, ulcerative colitis, Crohn's disease, irritable bowel disease, inflammatory bowel disease, rheumatoid arthritis, juvenile rheumatoid arthritis, familial Mediterranean fever, amyotrophic lateral sclerosis, Sjogren's syndrome, early arthritis, viral arthritis, multiple sclerosis, or psoriasis. The diagnosis and treatment of these diseases are well documented in the literature.

viii. Chemotherapy, Radiotherapy and Cytokine Therapy Toxicity

Various forms of cancer therapy, including chemotherapy, radiation, and cytokines, are associated with toxicity, sometimes severe, in the cancer patient. To the extent that the toxicity is caused at least in part by the extracellular actions of histones, the present invention seeks to reduce this toxicity using the pharmaceutical compositions of the present invention, thereby reducing or alleviating discomfort on the part of the patient, as well as permitting higher doses of the therapy.

ix. Burns

In medicine, a burn may be an injury caused by heat, cold, electricity, chemicals, friction or radiation. First-degree burns are usually limited to redness (erythema), a white plaque, and minor pain at the site of injury. These burns usually extend only into the epidermis. Second-degree burns additionally fill with clear fluid, have superficial blistering of the skin, and can involve more or less pain depending on the level of nerve involvement. Second-degree burns involve the superficial (papillary) dermis and may also involve the deep (reticular) dermis layer. Third-degree burns additionally have charring of the skin, and produce hard, leather-like eschars. An eschar is a scab that has separated from the unaffected part of the body. Frequently, there is also purple fluid. These types of burns are often painless, because nerve endings have been destroyed in the burned areas. Serious burns, especially if they cover large areas of the body, can cause death; any hint of burn injury to the lungs (e.g., through smoke inhalation) is a medical emergency.

Burns that injure the tissues underlying the skin, such as the muscles or bones, are sometimes categorized as fourth-degree burns. These burns are broken down into three additional degrees: fourth-degree burns result in the skin being irretrievably lost, fifth-degree burns result in muscle being irretrievably lost, and sixth-degree burns result in bone being charred.

A newer classification of "Superficial Thickness," "Partial Thickness" (which is divided into superficial and deep categories) and "Full Thickness" relates more precisely to the epidermis, dermis and subcutaneous layers of skin and is used to guide treatment and predict outcome.

Chemical burns are usually caused by chemical compounds, such as sodium hydroxide (lye), silver nitrate, and more serious compounds (such as sulfuric acid). Most chemicals (but not all) that can cause moderate to severe chemical burns are strong acids or bases. Nitric acid, as an oxidizer, is possibly one of the worst burn-causing chemicals. Hydrofluoric acid can eat down to the bone and its burns are often not immediately evident. Most chemicals that can cause moderate to severe chemical burns are called caustic.

Electrical burns are generally symptoms of electric shock, being struck by lightning, being defibrillated or cardioverted without conductive gel, etc. The internal injuries sustained may be disproportionate to the size of the "burns" seen—as these are only the entry and exit wounds of the electrical current.

Burns are assessed in terms of total body surface area (TBSA), which is the percentage affected by partial thickness or full thickness burns (superficial thickness burns are not counted). The rule of nines is used as a quick and useful way to estimate the affected TBSA. The first step in managing a person with a burn is to stop the burning process. With dry powder burns, the powder should be brushed off first. With other burns, the affected area should be rinsed with a large amount of clean water to remove foreign bodies and help stop the burning process. Cold water should never be applied to any person with extensive burns, as it may severely compromise the burn victim's temperature status. At this stage of management, it is also critical to assess the airway status. If the patient was involved in a fire, then it must be assumed that he or she has sustained inhalation injury until proven otherwise, and treatment should be managed accordingly.

Once the burning process has been stopped, and airway status is ensured, the patient should be volume resuscitated according to the Parkland formula. This formula dictates that the amount of Lactated Ringer's solution to deliver in the first twenty four hours after time of injury is:

fluid=4 cc×% TBSA×weight in kg

% TBSA excludes any first degree burn

Half of this fluid should be given in the first eight hours post injury and the rest in the subsequent sixteen hours. The formula is a guide only and infusions must be tailored to urine output and central venous pressure. Inadequate fluid resuscitation causes renal failure and death. Severe edema in full thickness burns may be treated by escharotomy.

x. Cancer

Cancer results from the outgrowth of a clonal population of cells from tissue. The development of cancer, referred to as carcinogenesis, can be modeled and characterized in a number of ways. An association between the development of cancer and inflammation has long-been appreciated. The inflammatory response is involved in the host defense against microbial infection, and also drives tissue repair and regeneration. Considerable evidence points to a connection between inflammation and a risk of developing cancer, i.e., chronic inflammation can lead to dysplasia.

Studies have estimated that nearly 15% of worldwide cancer is associated with microbial infection. Organisms such as human papilloma virus (HPV), hepatitis B and C virus, HIV, and *Helicobacter pylori* all have been linked to cancer. In other cases, environmental conditions causing chronic irritation and subsequent inflammation can also predispose to cancer, including cigarette smoke, asbestos and silica.

In the case of some types of viral infection, virally-encoded genes can contribute to cellular transformation. An example is the HPV oncoproteins E6 and E7. However, other microbes associated with cancer do not operate in this fashion as they are not transforming. For example, certain strains of *H. pylori* contain factors that affect host cell signaling but do not contain oncogenes. Interestingly, it has been observed that *H. pylori* induces MUC1.

Other ways in which chronic inflammatory states can lead to genomic lesions and tumor initiation are chemical. For example, host cells fight microbial infection by the production of free radicals. In addition to their anti-microbial effects, these molecules lead to oxidative damage and nitration of DNA bases which increases the risk of DNA mutations even in host cells.

Yet another path to cellular dysregulation may result from the cell death that occurs in infection or other inflammatory insult. Lost cells must be repopulated by the expansion of other cells, sometimes undifferentiated precursor cells such as tissue stem cells. Not surprisingly, many inflammatory pathways function to mediate survival and proliferation. Thus, in attempting to mediating tissue repair, the inflammatory response may unwittingly provide excessive survival and proliferative signals to cells, thus leading to tumorigenesis.

Because of the link between cancer and inflammation, the ability of the peptides and peptide analogs of the present invention to reduce inflammatory signalling pathways can be exploited in a pre-cancer or cancer risk situation to prevent or delay the onset of dysplastic growth.

C. Treatment Methods

Compounds that inhibit MUC1 oligomer formation are generally useful as anti-inflammatories. They can be administered to mammalian subjects (e.g., human patients) alone or in conjunction with other drugs that modulate inflammation. The compounds can also be administered to subjects that are genetically and/or due to, for example, physiological and/or environmental factors, susceptible to inflammation, e.g., subjects with a family history of inflammatory disease, or subjects with chronic inflammation or subject to chronic stress.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more times). Encapsulation of the polypeptide in a suitable delivery vehicle (e.g., polymeric microparticles or implantable devices) may increase the efficiency of delivery, particularly for oral delivery.

D. Combination Therapies

It is common in many fields of medicine to treat a disease with multiple therapeutic modalities, often called "combination therapies." Inflammatory disease are no exception.

To treat inflammatory disorders using the methods and compositions of the present invention, one would generally contact a target cell or subject with a MUC1 antagonist and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the MUC1 antagonist and the other includes the other agent.

Alternatively, the MUC1 antagonist may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the MUC1 antagonist or the other therapy will be desired. Various combinations may be employed, where the MUC1 antagonist is "A," and the other therapy is "B," as exemplified below:

| |
|---|
| A/B/A B/A/B B/B/A A/A/B B/A/A A/B/B B/B/B/A B/B/A/B |
| A/A/B/B A/B/A/B A/B/B/A B/B/A/A B/A/B/A B/A/A/B B/B/B/A |
| A/A/A/B B/A/A/A A/B/A/A A/A/B/A A/B/B/B B/A/B/B B/B/A/B |

Other combinations are contemplated. The skilled artisan is directed to "Remingtons Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating inflammation, cancer, etc.

Inflammation.

Agents or factors suitable for use in a combined therapy against an inflammatory disorder include steroids, glucocorticoids, non-steroidal anti-inflammatory drugs (NSAIDS; including COX-1 and COX-2 inhibitors), aspirin, ibuprofen, and naproxen. Analgesics are commonly associated with anti-inflammatory drugs but which have no anti-inflammatory effects. An example is paracetamol, called acetaminophen in the U.S. and sold under the brand name of Tylenol. As opposed to NSAIDS, which reduce pain and inflammation by inhibiting COX enzymes, paracetamol has recently been shown to block the reuptake of endocannabinoids, which only reduces pain, likely explaining why it has minimal effect on inflammation.

Cancer.

Agents or factors suitable for use in a combined therapy include any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic" or "genotoxic agents," are intended to be of use in the combined treatment methods disclosed herein. In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition.

Various classes of chemotherapeutic agents are comtemplated for use with in combination with peptides of the present invention. For example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use, include, e.g., camptothecin, actinomycin-D, mitomycin C. The invention also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with a MUC1 peptide, as described above.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include Adriamycin, also known as Doxorubicin, Etoposide, Verapamil, Podophyllotoxin, and the like. Widely used in a clinical setting for the treatment of neoplasms, these compounds are administered through bolus injections intravenously at doses ranging from 25-75 mg/m$^2$ at 21 day intervals for Doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

Epidermal growth factor receptor inhibitors, such as Iressa, mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in combination cancer therapy in accordance with the present invention.

Another possible combination therapy with the peptides claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the local or regional delivery of MUC1 peptides to patients with cancer will be a very efficient method for treating the clinical disease. Similarly, the chemo- or radiotherapy may be directed to a particular, affected region of the subject's body. Alternatively, regional or systemic delivery of expression construct and/or the agent may be appropriate in certain circumstances, for example, where extensive metastasis has occurred.

In addition to combining MUC1 therapies with chemo- and radiotherapies, it also is contemplated that combination with immunotherapy, hormone therapy, toxin therapy and surgery. In particular, one may employ targeted therapies such as Avastin, Erbitux, Gleevec, Herceptin and Rituxan.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell Culture.

Human breast cancer ZR-75-1, ZR-75-1/vector, ZR-75-1/MUC1siRNA (Ren et al., 2004) cell lines were grown in RPMI1640 medium supplemented with 10% heat-inactivated fetal bovine serum (HI-FBS), 100 U/ml penicillin, and 100 µg/ml streptomycin (Invitrogen) in a humidified incubator at 37° C. and 5% $CO_2$. Human MCF-7 breast cancer cells and 293 cells were grown in Dulbecco's modified Eagle's medium with 10% HI-FBS, antibiotics and 2 mM L-glutamine. Human MCF-10A breast epithelial cells were grown in mammary epithelial cell growth medium (MEGM; Lonza). Cells were treated with the MUC1/CQC or MUC1/AQA peptides synthesized by the MIT Biopolymer Laboratory, Cambridge, Mass. Viability was determined by trypan blue exclusion.

Immunoprecipitation and Immunoblot Analysis.

Whole cell and nuclear lysates were prepared as described (Leng et al., 2007). Soluble proteins were subjected to immunoprecipitation with anti-Flag (Sigma, St. Louis, Mo.). Immunoprecipitates and soluble proteins were analyzed by immunoblotting with anti-His (Cell Signaling Technology, Danvers, Mass.), anti-GFP (Millipore, Danvers, Mass.), anti-Flag, anti-MUC1-C (Ab1; NeoMarkers, Fremont, Calif.), anti-lamin B (EMD, La Jolla, Calif.) or anti-β-actin (Sigma). Reactivity was detected with horseradish peroxidase-conjugated second antibodies and chemiluminescence.

Cell Transfection.

293 cells were transfected with vectors expressing GFP, GFP-MUC1-CD or Flag-MUC1-CD in the presence of Lipofectamine as described (Leng et al., 2007).

Peptide Uptake.

Cells were incubated with FITC-labeled MUC1/CQC peptide (MIT Biopolymer Laboratory), washed with cold PBS, fixed in 1% paraformaldehyde/PBS and analyzed for fluorescence by flow cytometry.

Analysis of Cell Cycle Distribution, Apoptosis and Necrosis.

Cells were harvested, washed with PBS, fixed with 80% ethanol, and incubated in PBS containing 40 µg/ml RNAse and 40 µg/ml propidium iodide for 30 min at 37° C. Cell cycle distribution was determined by flow cytometry. Sub-G1 DNA content was assessed by staining ethanol-fixed and citrate buffer-permeabilized cells with propidium iodide and monitoring by flow cytometry as described (Yin et al., 2007). For assessment of necrosis, cells were incubated with 1 µg/ml propidium iodide/PBS for 5 min at room temperature and then monitored by flow cytometry as described (Yin et al., 2007).

Example 2

Results

Effects of the MUC1/CQC Peptide on MUC1 Oligomer Formation.

Figure 1C:
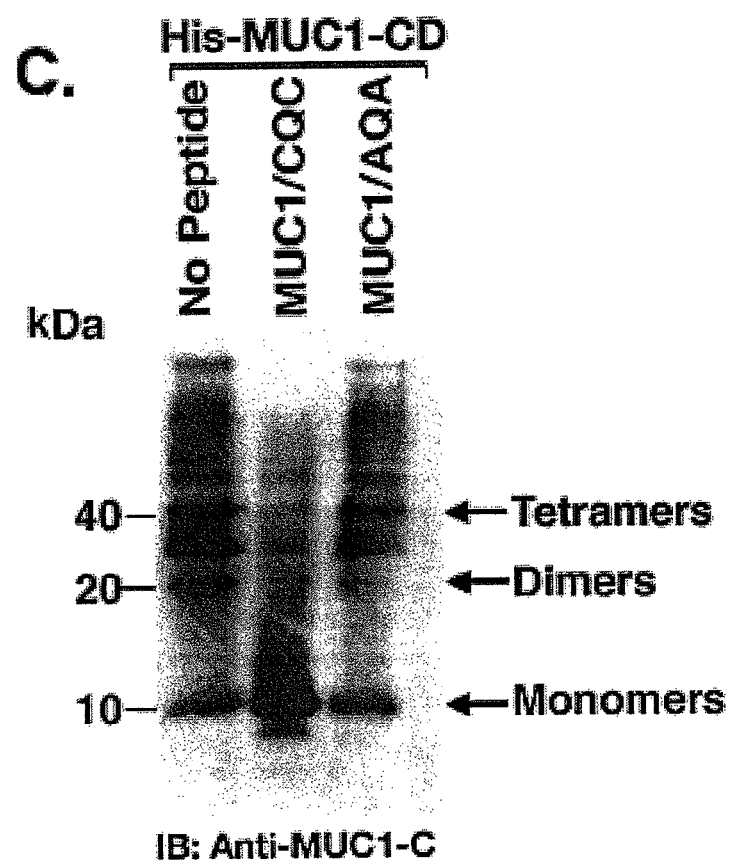
Figure 1D:
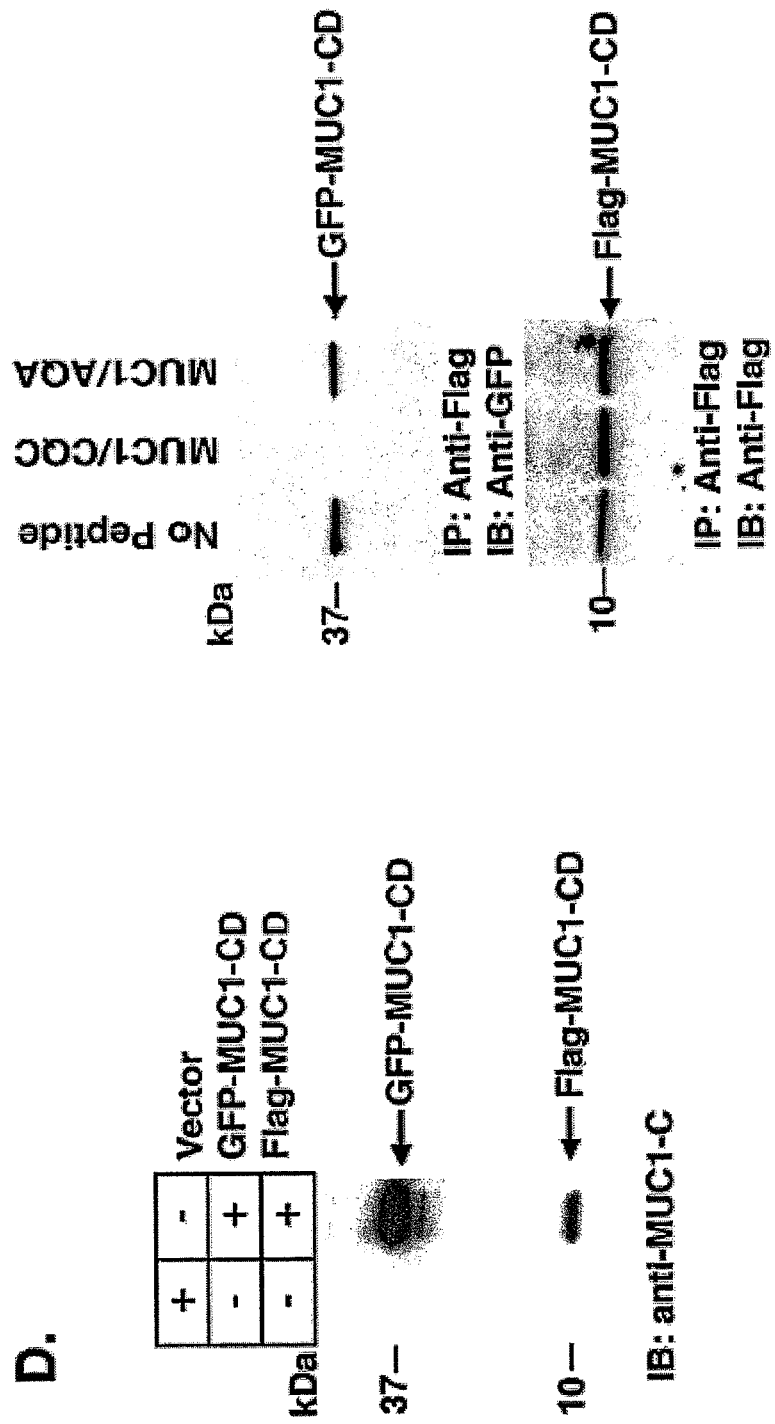

The MUC1 cytoplasmic domain (MUC1-CD) contains a CQC motif that is necessary for the formation of oligomers and nuclear localization (Leng et al., 2007). To determine whether a small molecule can be designed to block oligomerization, the inventors synthesized a peptide derived from the N-terminal region of MUC1-CD that contains the CQC motif (MUC1/CQC peptide; FIG. 1A). A poly D-arginine transduction domain was included in the synthesis to facilitate entry of the peptide into cells (Fischer, 2007) (FIG. 1A). As a control, a similar peptide was synthesized in which the CQC motif was altered to AQA (MUC1/AQA peptide; FIG. 1A). To assess binding of the peptides to MUC1-CD, the inventors immobilized His-tagged MUC1-CD to a BIAcore sensor chip. The MUC1/CQC peptide bound to His-MUC1-CD with a dissociation constant (Kd) of 30 nM (FIG. 1B), which is similar to that obtained with MUC1-CD oligomers (Leng et al., 2007). By contrast, there was no apparent binding of the MUC1/AQA peptide (data not shown). Purified His-tagged MUC1-CD forms oligomers as detected by electrophoresis in polyacrylamide gels (FIG. 1C). Incubation of His-MUC1-CD with the MUC1/CQC peptide substantially decreased oligomer formation and increased the monomers (FIG. 1C). Moreover, incubation with the MUC1/AQA peptide had little if any effect (FIG. 1C). To assess effects on MUC1 oligomerization in vivo, 293 cells were transfected with vectors expressing GFP-MUC1-CD and Flag-MUC1-CD (FIG. 1D, left). Complexes of GFP-MUC1-CD and Flag-MUC1-CD were detectable by coprecipitation of lysates from cells not exposed to peptide (FIG. 1D, right). In concert with the in vitro results, incubation of the transfected 293 cells with MUC1/CQC peptide was associated with disruption of the interaction between Flag-MUC1-CD and GFP-MUC1-CD (FIG. 1D, right). In addition, the MUC1/AQA peptide had no apparent effect (FIG. 1D, right). These results indicate that the MUC1/CQC peptide binds to MUC1-CD and blocks formation of MUC1-CD oligomers in vitro and in cells.

MUC1/CQC Peptide Blocks Targeting of MUC1-C to the Nucleus.

Figure 2A:
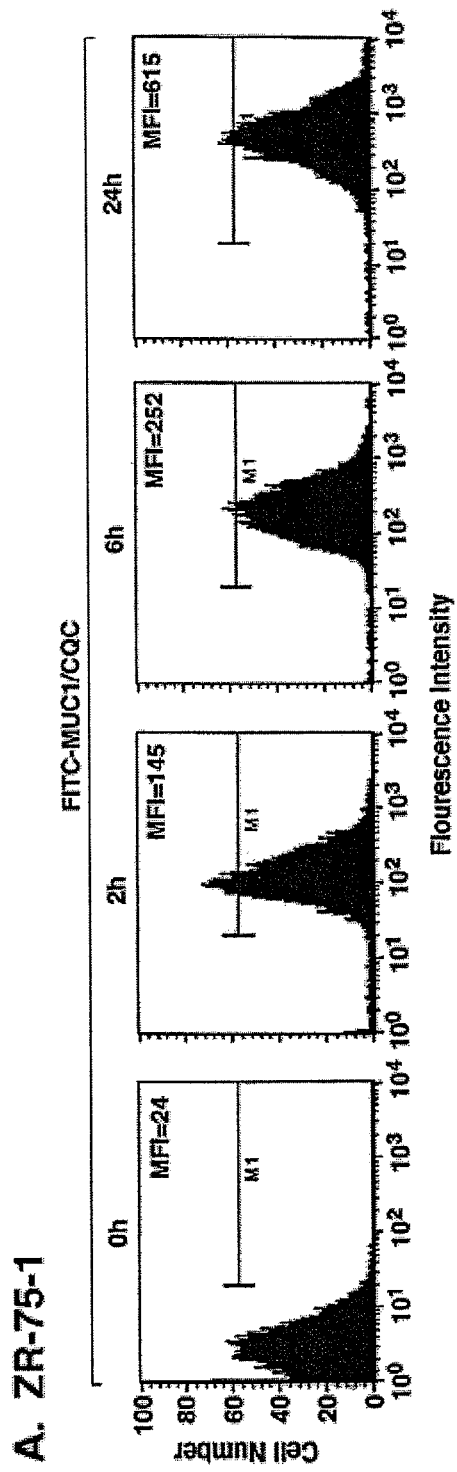
FIGS. 2A-C. MUC1/CQC peptide blocks nuclear localization of MUC1-C.
Figure 2B:
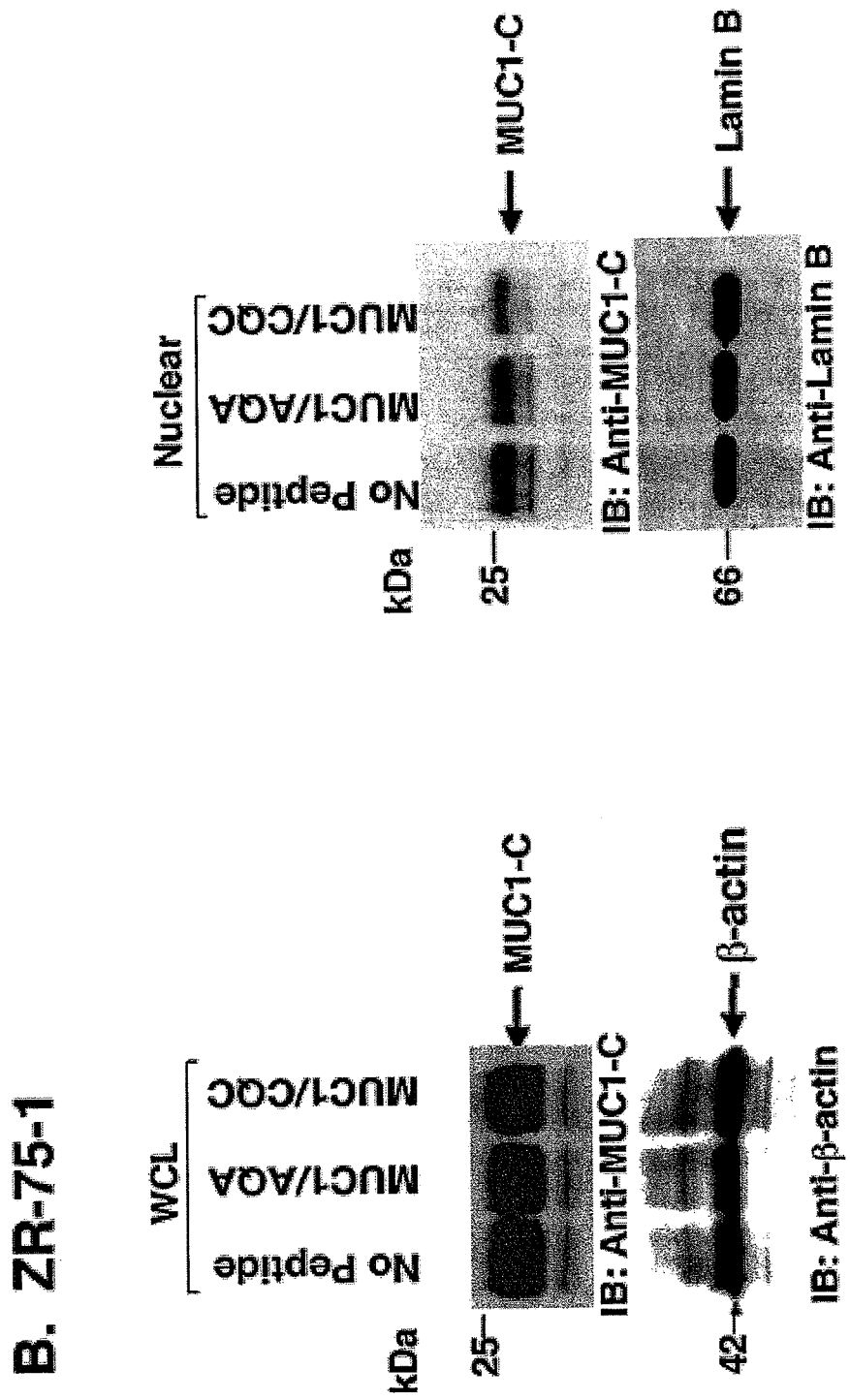
Figure 2C:
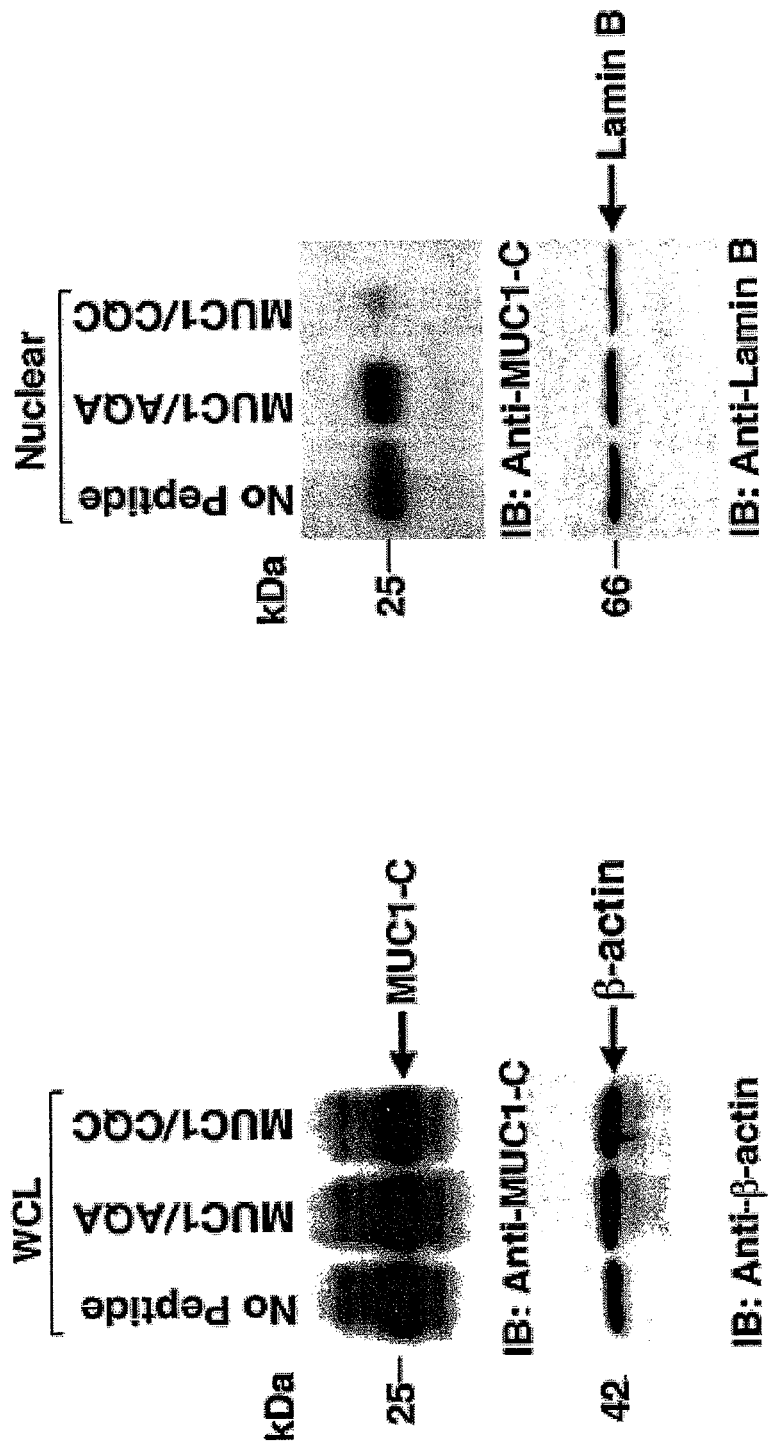

Human ZR-75-1 and MCF-7 breast cancer cells overexpress endogenous MUC1, and thus represent potential models for evaluating effects of the MUC1/CQC peptide (Ramasamy et al., 2007). To assess uptake, the ZR-75-1 cells were incubated with 5 μM FITC-MUC1/CQC peptide (FIG. 2A). At 2 h, analysis of the cells by flow cytometry showed a substantial increase in fluorescence intensity with a mean (MFI) of 145 (FIG. 2A). Further increases in MFI were identified at 6 and 24 h (FIG. 2A). Oligomerization of MUC1-C is necessary for its nuclear import (Leng et al., 2007). Treatment of ZR-75-1 cells with the MUC1/CQC or the MUC1/AQA peptide had no effect on cellular MUC1-C levels (FIG. 2B). However, in concert with effects on oligomerization, treatment with the MUC1/CQC, and not the MUC1/AQA, peptide was associated with decreases in nuclear MUC1-C levels (FIG. 2B). Similar effects were observed in MCF-7 cells with down-regulation of nuclear MUC1-C levels in response to treatment with the MUC1/CQC peptide (FIG. 2C). These findings indicate that the MUC1/CQC peptide blocks MUC1-C oligomerization and thereby targeting of MUC1-C to the nucleus.

MUC1/CQC Peptide Blocks Growth and Induces Necrosis.

Figure 3A:
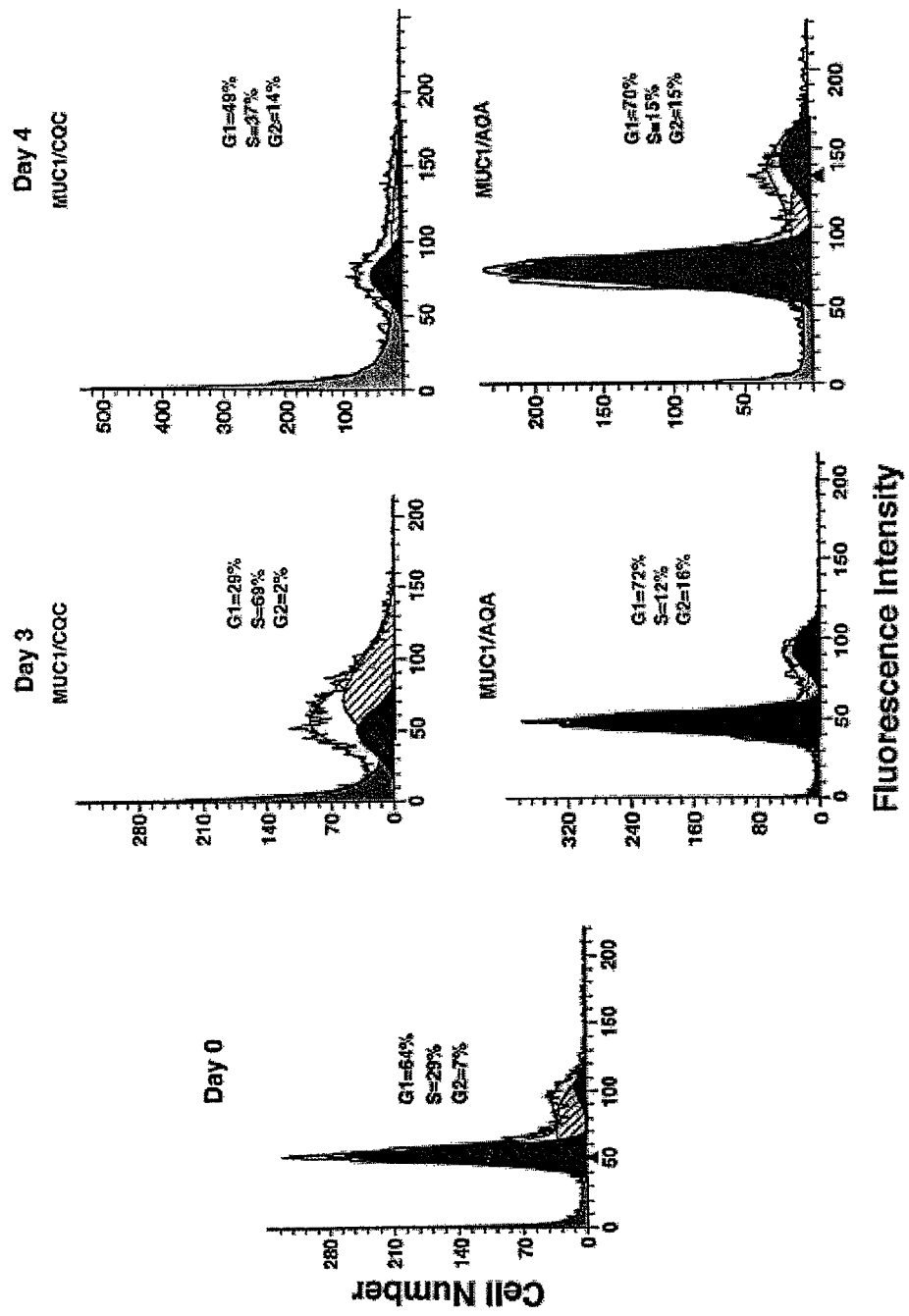
FIGS. 3A-D. MUC1/CQC peptide induces S phase arrest and necrosis. ZR-75-1 (FIGS. 2A-B) and MCF-7 (FIGS. 2C-D) cells were treated with 5 µM MUC1/CQC or MUC1/AQA for 3 and 4 d. Cells were fixed and analyzed for cell cycle distribution by flow cytometry (FIGS. 2A and 2C). The percentage of cells in G1, S and G2/M phases is included in the panels. Cells were also stained with propidium iodide and analyzed by flow cytometry for necrosis (FIGS. 2B and 2D). The percentage of necrotic cells is included in the panels.
Figure 3B:
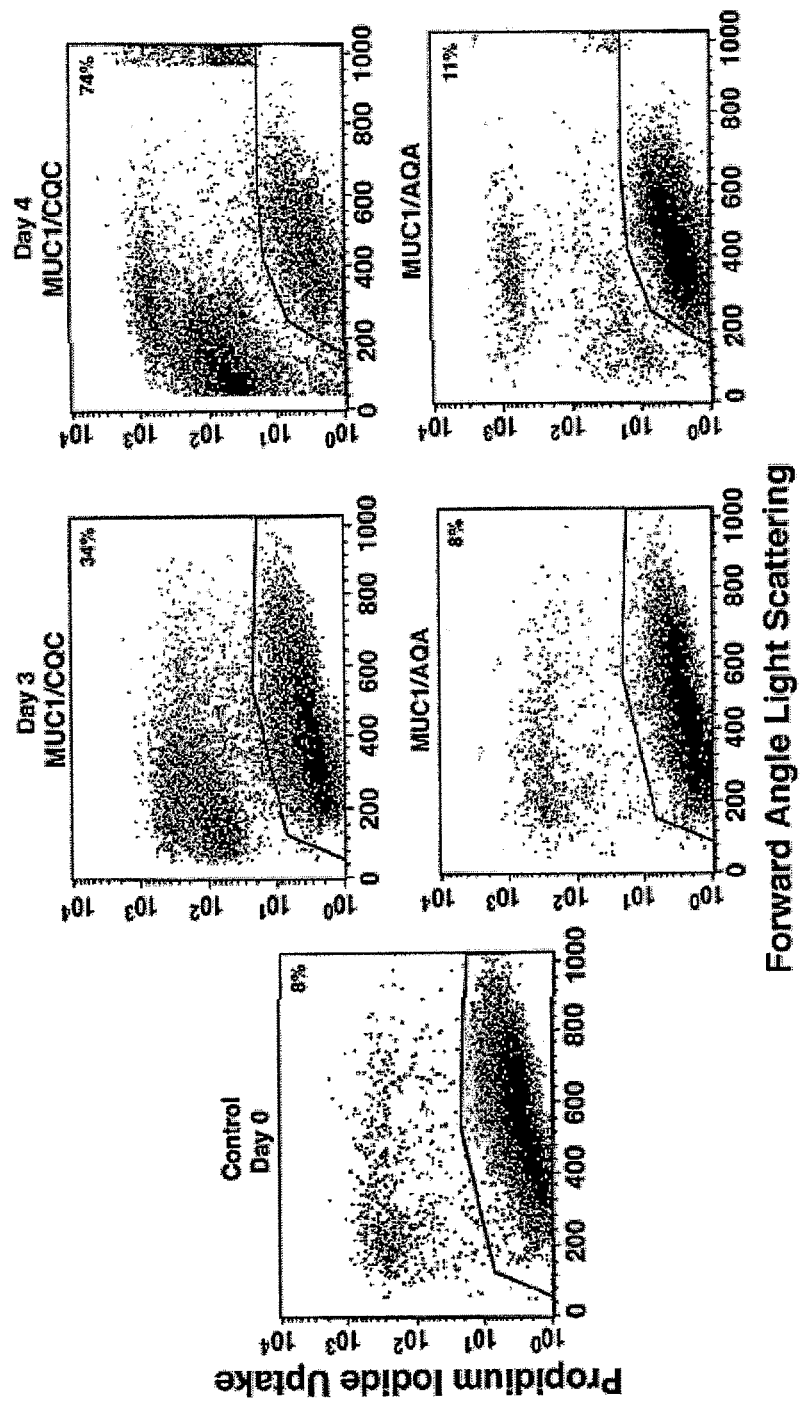
Figure 3C:
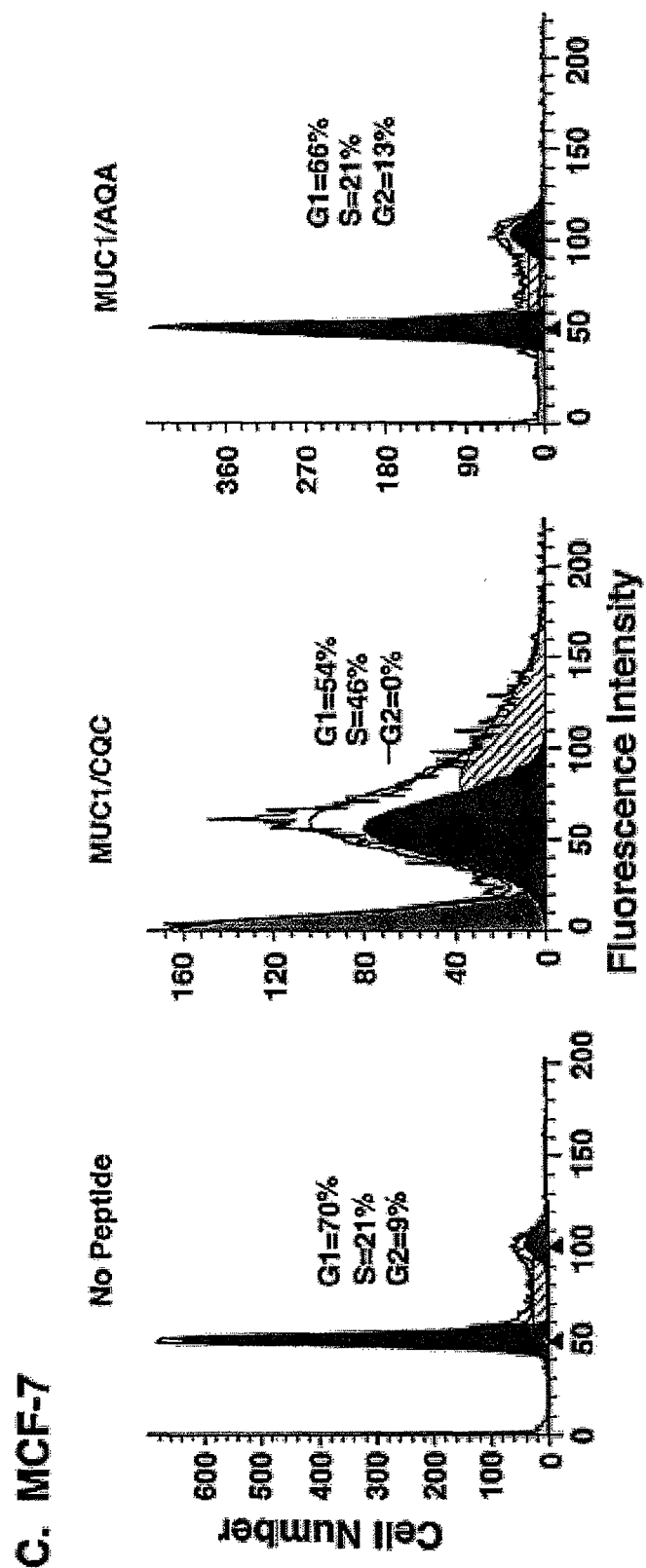
Figure 3D:
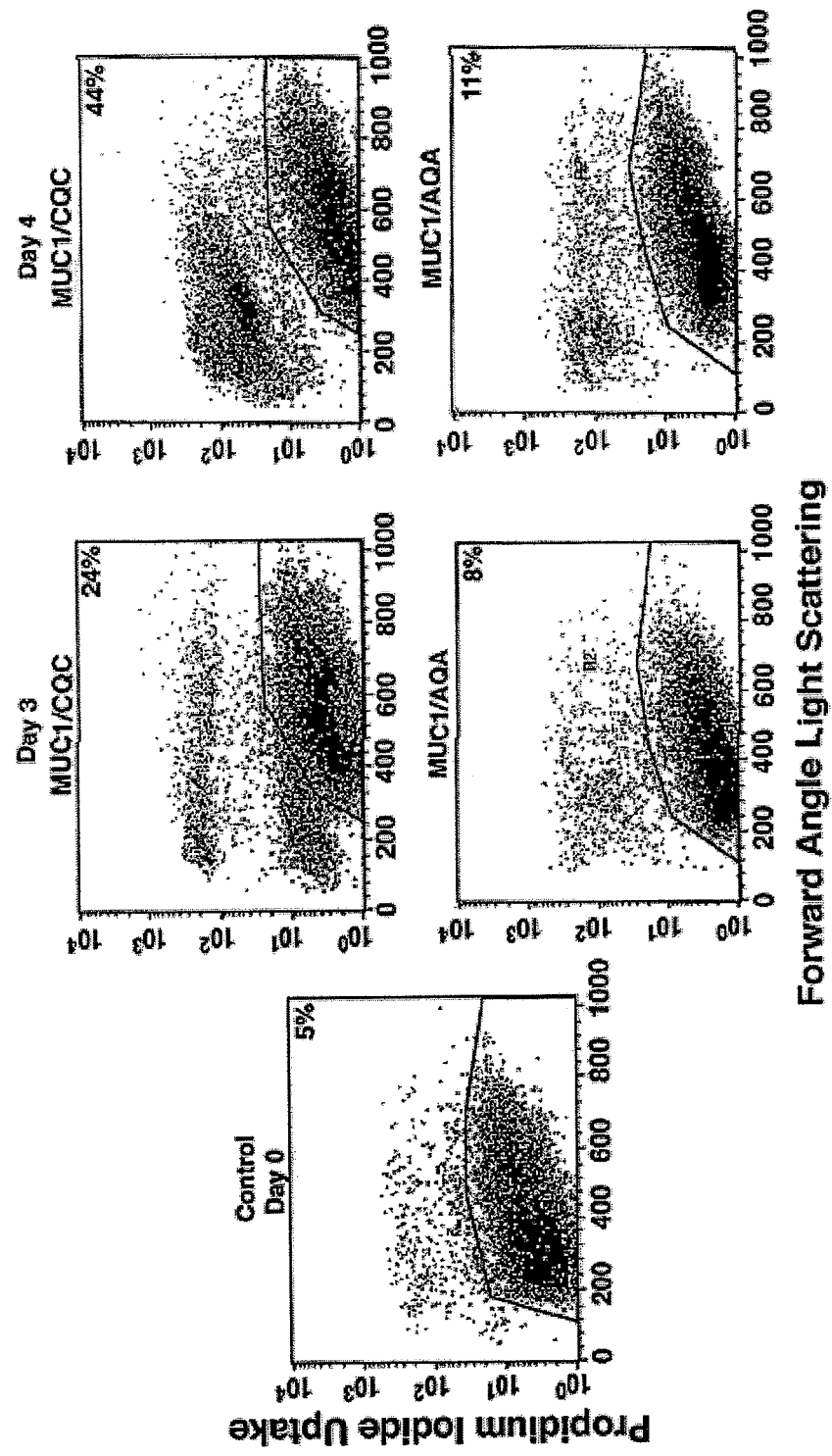

To determine whether the MUC1/CQC peptide affects growth, ZR-75-1 cells were treated with 5 μM MUC1/CQC for 72 h and monitored for cell cycle distribution. Significantly, there was a substantial arrest in S phase as compared to that in cells left untreated or treated with the MUC1/AQA peptide (FIG. 3A). By 96 h, the S phase population was decreased, potentially through attrition by cell death (FIG. 3A). There was little if any accumulation of cells with sub-G1 DNA content to support the induction of apoptosis (FIG. 3A). However, treatment of ZR-75-1 cells with the MUC1/CQC, and not the MUC1/AQA, peptide was associated with the induction of necrosis, which was detectable at 72 h and more prominent at 96 h (FIG. 3B). The MCF-7 cells responded similarly to the MUC1/CQC peptide with arrest of growth in S phase (FIG. 3C) and the induction of necrosis (FIG. 3D). These findings indicate that the MUC1/CQC peptide inhibits growth and induces necrosis of human breast cancer cells.

Specificity of MUC1/CQC Peptide for MUC1 Expressing Carcinoma Cells.

Figure 4A:
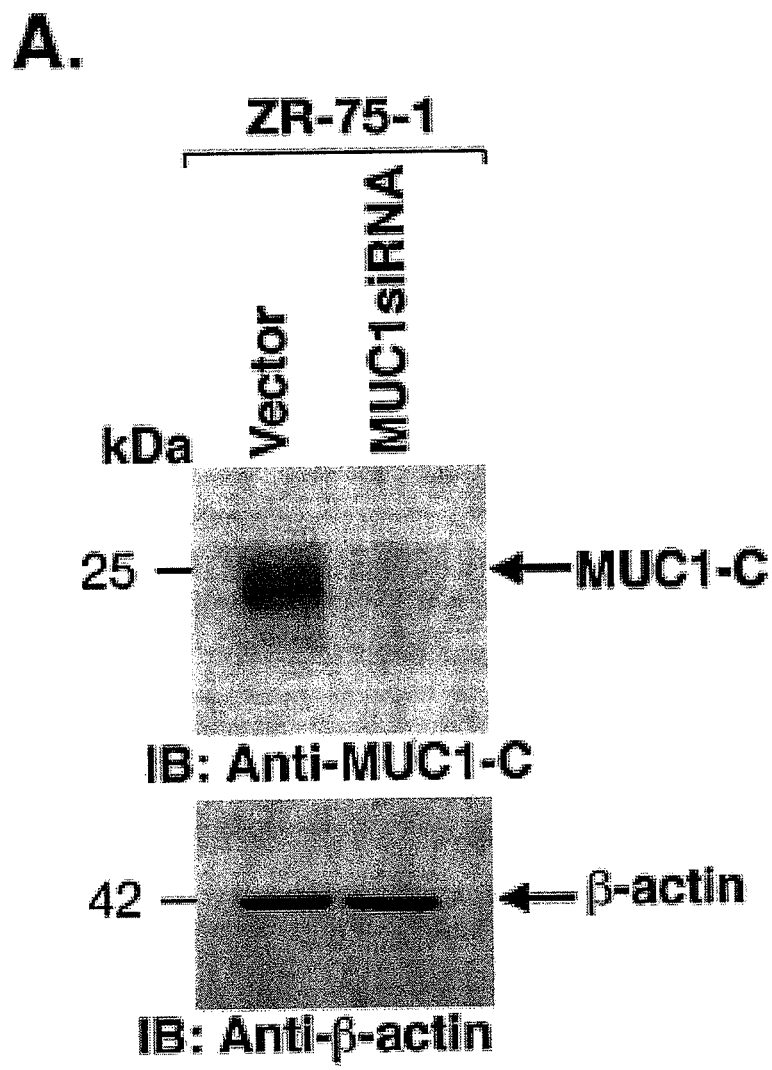
FIGS. 4A-E. Selectivity of MUC1/CQC for MUC1 expressing breast cancer cells.
Figure 4B:
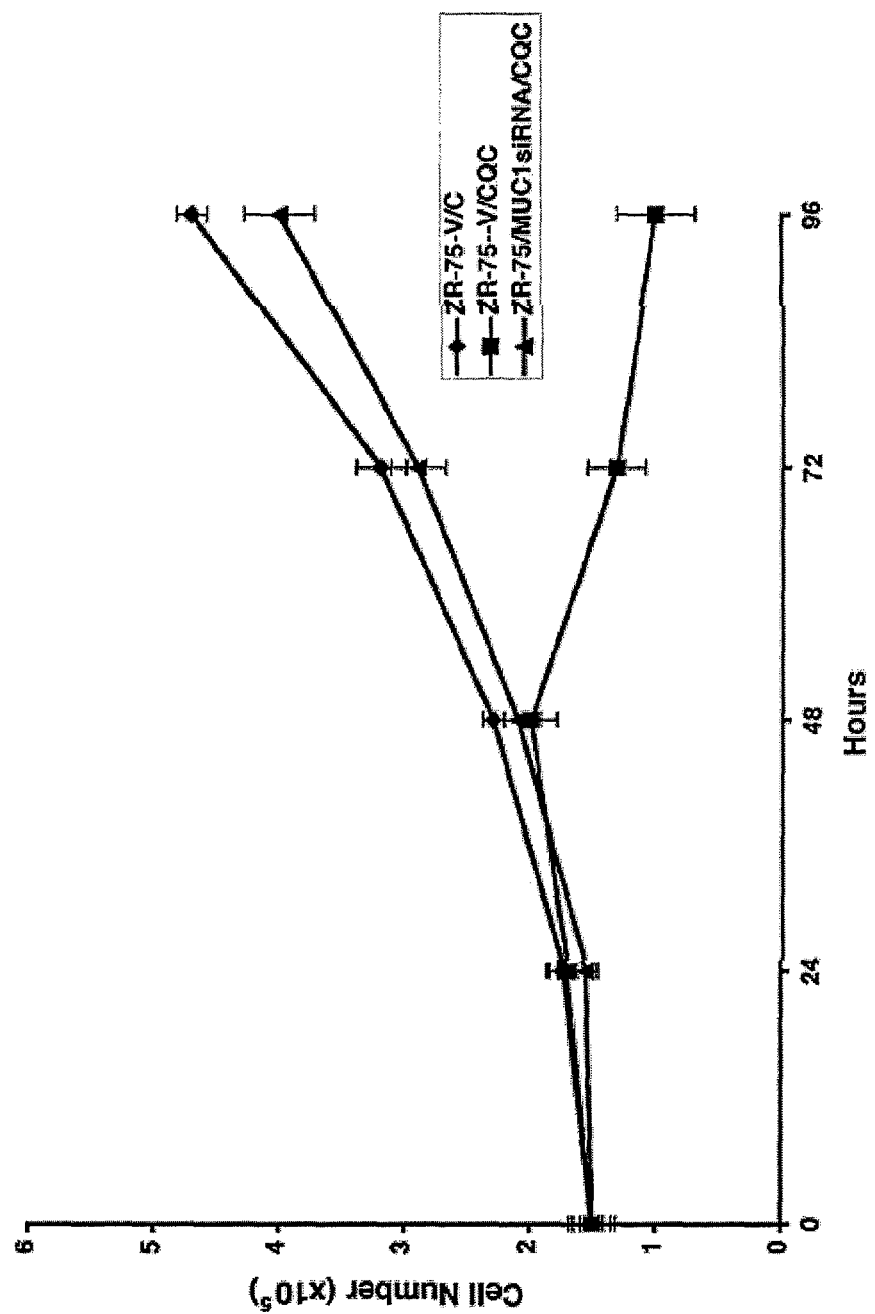
Figure 4C:
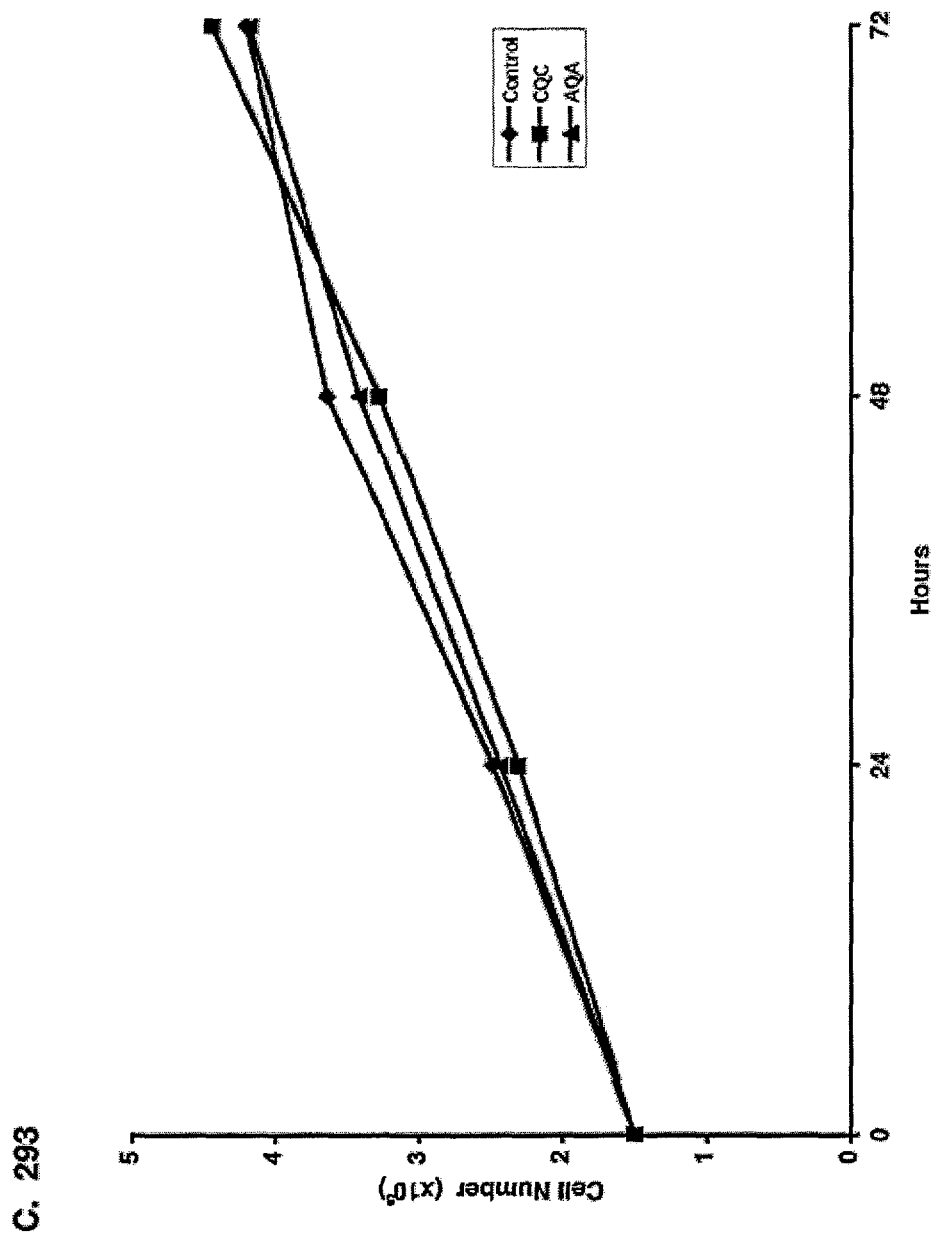
Figure 4D:
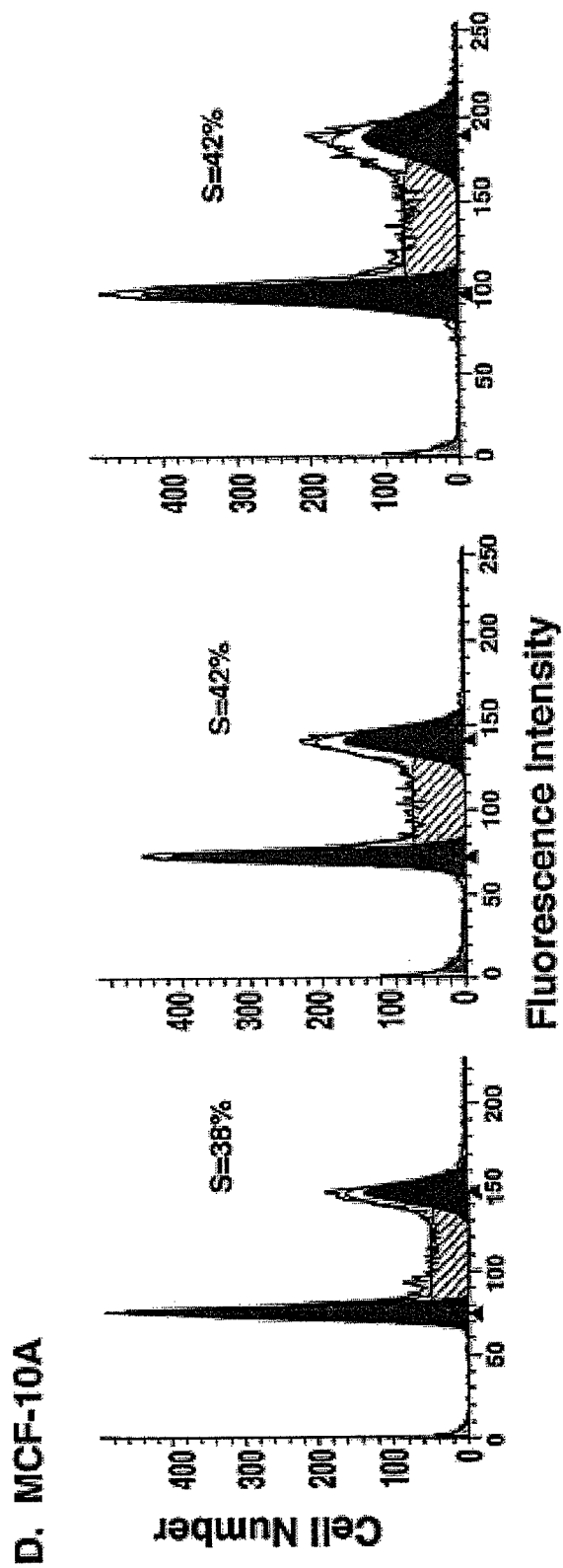
Figure 4E:
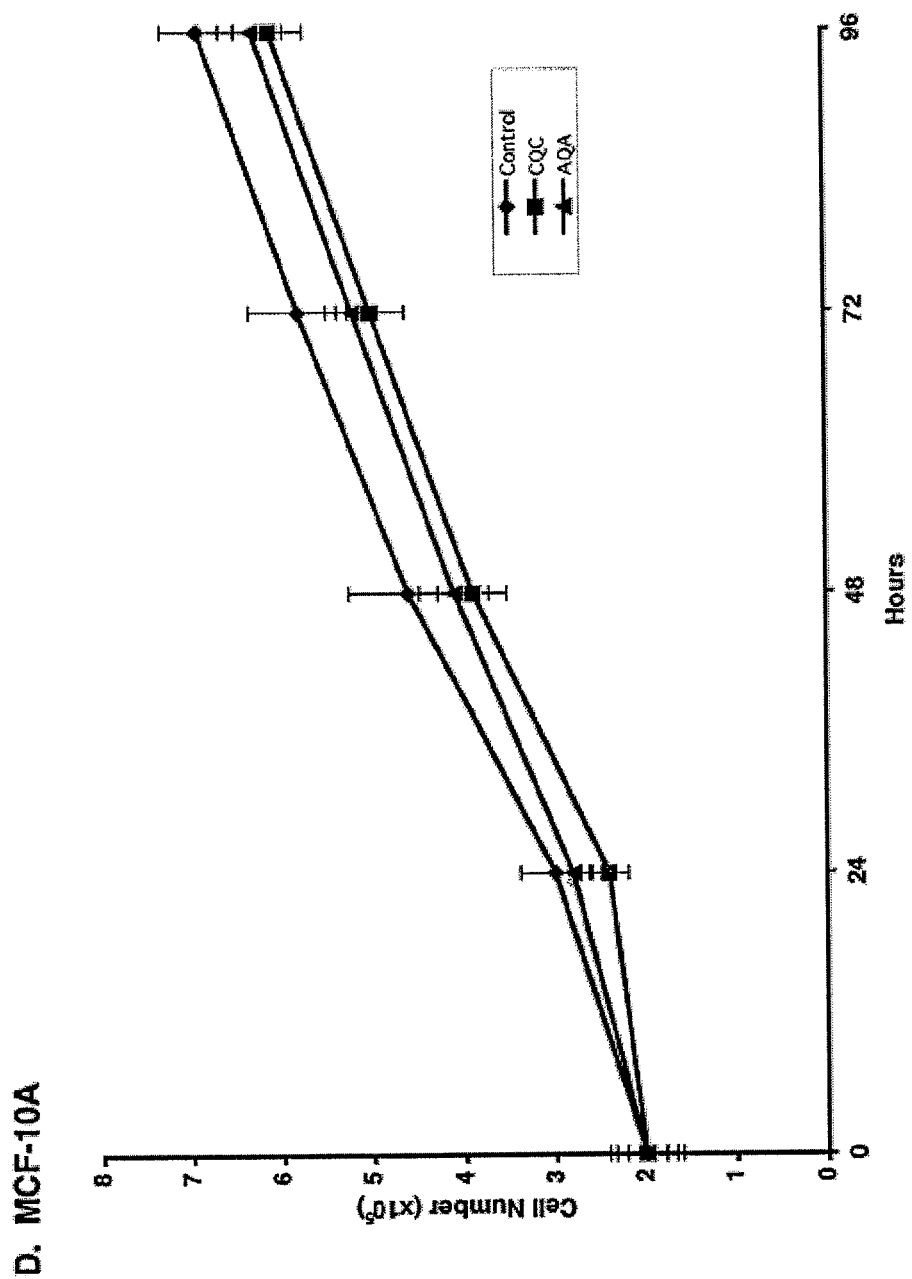

To determine whether the MUC1/CQC peptide has selective activity against breast carcinoma cells that overexpress endogenous MUC1, the inventors treated ZR-75-1 cells that are stably silenced for MUC1 expression with a MUC1siRNA (FIG. 4A). In contrast to growth arrest and death of the control ZR-75-1/vector cells, the MUC1/CQC peptide had substantially less effect on the ZR-75-1/MUC1siRNA cells (FIG. 4B). In addition, the MUC1/CQC peptide had no apparent effect on growth of MUC1-negative 293 cells (FIG. 4C). Studies were also performed on the MCF-10A non-transformed mammary epithelial cell line (Muthuswamy, 2001; Soule, 1990), which expresses MUC1, but at levels lower than that found in ZR-75-1 and MCF-7 cells (Ahmad et al., 2007). Notably, in contrast to ZR-75-1 and MCF-7 cells, the MUC1/CQC peptide had no effect on MCF-10A cell cycle distribution (FIG. 4D) and growth (FIG. 4E). These findings indicate that the MUC1/CQC peptide has selective activity against breast carcinoma cells that overexpress endogenous MUC1.

MUC1/CQC Peptide Inhibits Tumorigenicity In Vivo.

Figure 5A:
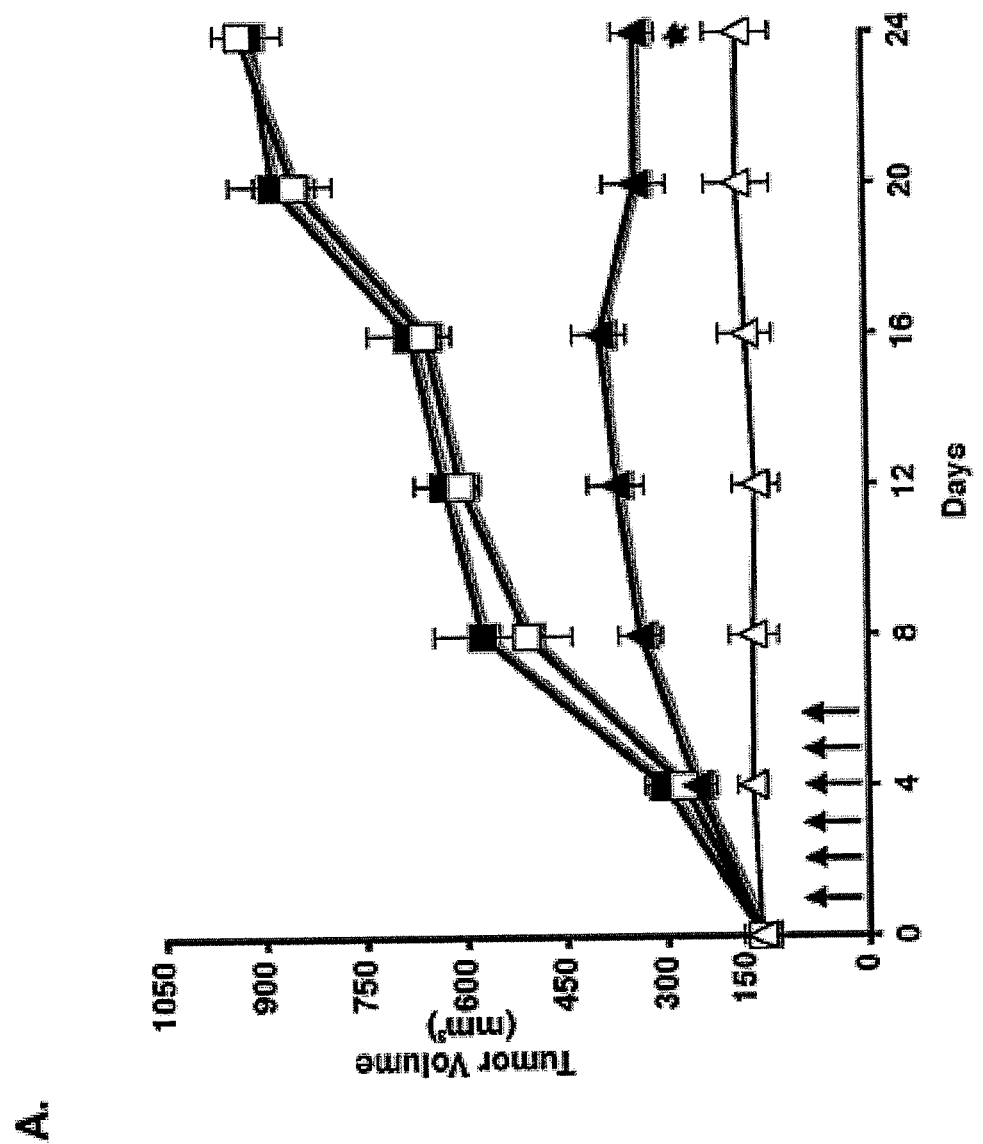
FIGS. 5A-C. MUC1/CQC peptide blocks growth of ZR-75-1 breast tumor xenografts.
Figure 5B:
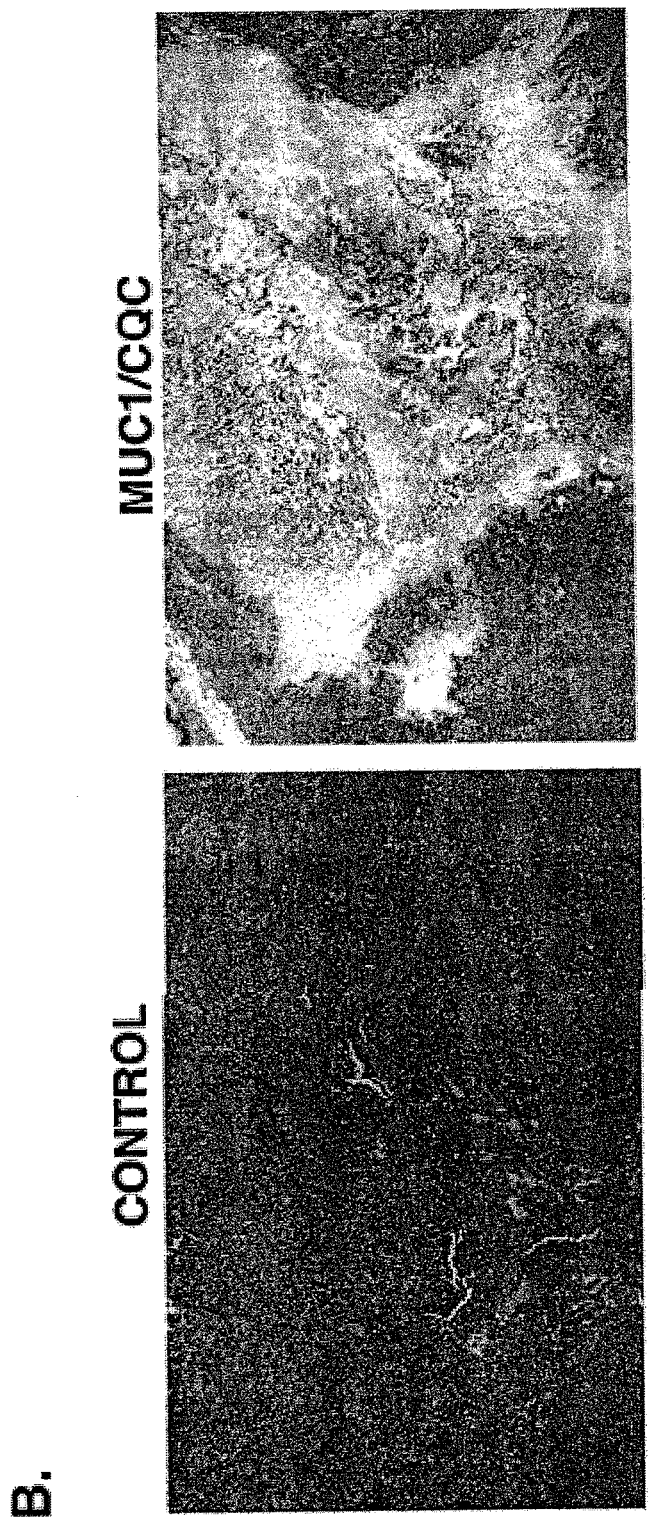
Figure 5C:
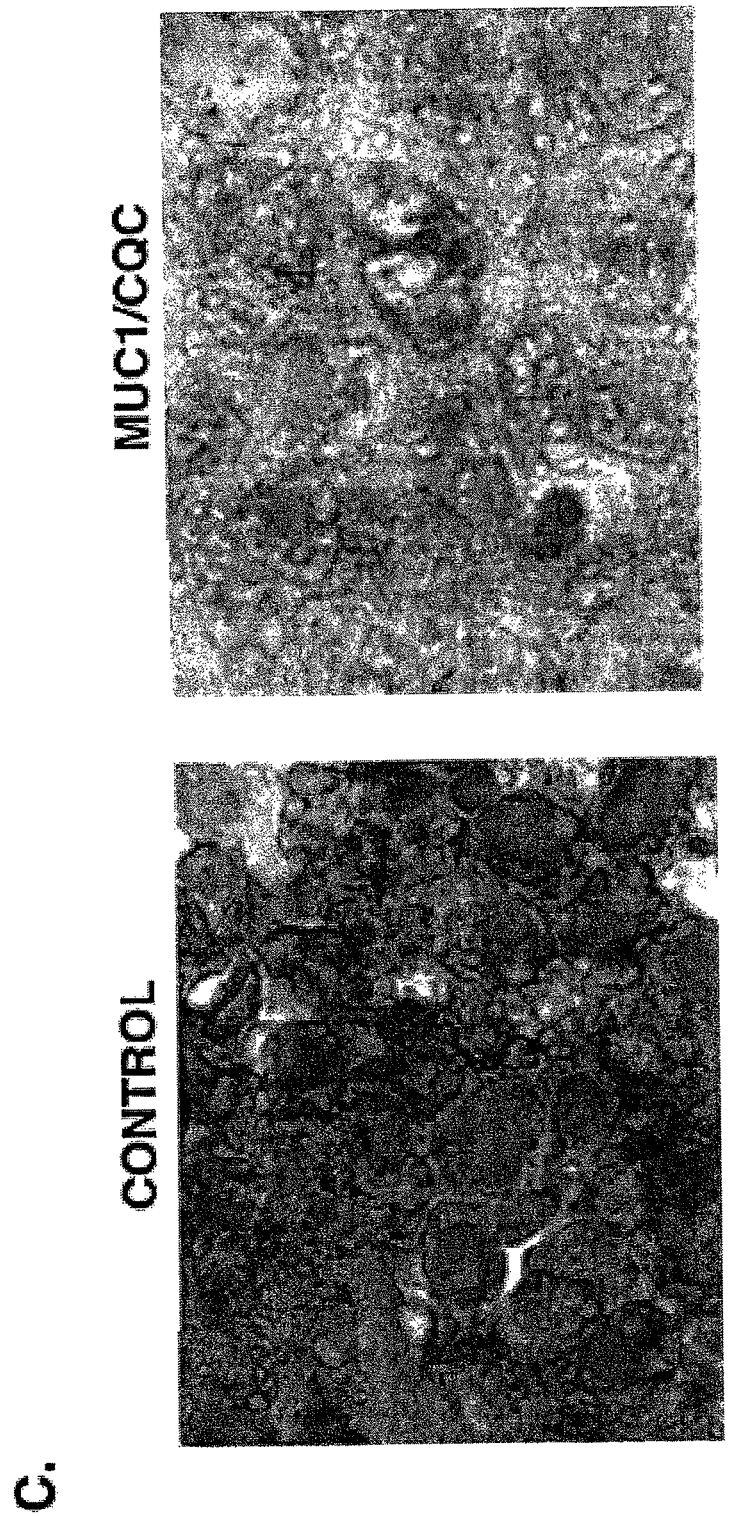

To determine if administration of the MUC1/CQC peptide is associated with effects on body weight, five female nude (nu/nu) mice were injected intraperitoneally (IP) once each day at a dose of 50 mg/kg. Administration of the peptide over 11 d had no apparent effect on weight of the individual mice. Moreover, there was no subsequent effect on bodyweight over the next 28 d after stopping MUC1/CQC administration (data not shown). To assess anti-tumor activity, ZR-75-1 cells ($1 \times 10^7$) were implanted subcutaneously into the flanks of nude mice. After 12 d, mice bearing tumors of approximately 150 mm$^3$ were treated with the MUC1/CQC peptide at doses of 10 and 50 mg/kg/d. As controls, mice were treated with vehicle alone or with the MUC1/AQA peptide. Administration of the MUC1/CQC peptide at 10 mg/kg/d×21 d slowed growth as compared to that obtained with the MUC1/AQA peptide given at 50 mg/kg/d (FIG. 5A). In addition, administration of the MUC1/CQC peptide at 50 mg/kg/d blocked growth over the initial 7 d of treatment (FIG. 5A). Consequently, treatment was stopped and the mice were monitored for regrowth. Significantly, there was no detectable growth of the tumors over the next 17 d (FIG. 5A). To assess in part the basis for the activity, tumors harvested from control and treated mice were examined by histopathology. Tumors from the MUC1/CQC (10 and 50 mg/kg) treated mice were markedly necrotic compared to that from mice treated with the vehicle or MUC1/AQA peptide (FIG. 5B and data not shown). Notably, however, tumor cells were also detectable around the areas of necrosis (FIG. 5B). Sections of the tumors were also stained with an antibody against MUC1. Treatment with the MUC1/AQA peptide was associated with a marked down-regulation of MUC1 expression compared to that in control tumors and those treated with the MUC1/AQA peptide (FIG. 5C and data not shown).

Plate-Based MUC1-CD Dimerization Inhibition Assay for Primary Screening.

To develop a HTS assay for compounds that inhibit MUC1-CD dimerization, the inventors generated purified His-tagged MUC1-CD protein. They also generated a biotin-labeled His-tagged MUC1-CD protein using a standard biotinylation kit. Biotinylated and non-biotinylated proteins were purified through Nickel columns.

The inventors coated 96- or 384-well plates with non-biotinylated MUC1-CD protein and added biotinylated MUC1-CD protein to the plates to initiate MUC1-CD/MUC1-CD dimerization or oligomerization. They then added a substrate to the plate which will bind to the biotinylated protein (only at the dimer or oligomer state) and the resultant fluorescence was detected by luminescence detection at absorbance 405 nM. A complete schematic illustration of this assay is described in FIG. 6.

Individual compounds from the chemical libraries were then added at multiple concentrations (0.01 μM to 100 μM) to the plates and following incubation and washing, the plates were read by luminescence detection at 405 nM. The formation of MUC1-CD/MUC1-CD dimers were detected when wells were incubated with DMSO (solvent for compounds). This value was normalized and considered as 100% dimerization. The hits were selected based on significant inhibition in Absorbance at 405 nM.

TABLE 1

Harvard Chemical Libraries Screened using Primary Screening Assay

| Library Name | Number of Compounds |
| --- | --- |
| Biomol ICCB Known Bioactives 3 | 480 |
| Ninds Custom Collection 2 | 1040 |
| Prestwick 1 Collection | 1120 |
| Microsource 1 | 1040 |
| NIH Clinical Collection 1 | 450 |
| Biomol 4 | 640 |
| TOTAL | 4770 |

In-Gel In Vitro MUC1-CD Dimerization Assay.

Purified His-tagged MUC1-CD protein forms dimers and oligomers when incubated in a buffer in vitro, as detected by electrophoresis in polyacrylamide gels. Selected compounds are incubated with purified His-tagged MUC1-CD protein for 60 min at room temperature. Following extensive washings, the proteins are separated in a non-reducing SDS-polyacrylamide gel and analyzed by immunoblotting with anti-MUC1-CD antibody.

Figure 7:
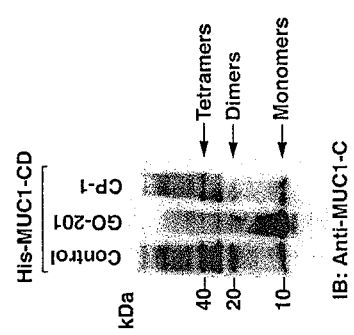
FIG. 7—GO-201 blocks MUC1 oligomerization. Purified His-MUC1-CD was incubated with PBS (control), GO-201, or CP-1 for 1 hr at room temperature. The proteins were separated in a non-reducing SDS-polyacrylamide gel (SDS-PAGE) and analyzed by immunoblotting with anti-MUC1-C antibodies. The formation of dimers and tetramers was inhibited by incubation with GO-201.

As a positive control for validation of this assay, purified His-MUC1-CD was incubated with either PBS or with GO-201 (CQC peptide) for 1 h at room temperature. The proteins were separated in a non-reducing SDS-polyacrylamide gel and analyzed by immunoblotting with anti-MUC1-CD antibody. Purified His-tagged MUC1-CD forms oligomers as detected by electrophoresis. Incubation of His-tagged MUC1-CD protein with GO-201 substantially decreased oligomer formation with a significant increase in monomer (FIG. 7).

Inhibition of Dimerization of MUC1-CD in Cyto.

The inventors generated two different versions of MUC1-CD vectors for transfecting into cells: GFP-MUC1-CD and Flag-MUC1-CD. HEK 293 cells, which do not express endogenous MUC1, were transiently transfected to express an empty vector, or GFP-MUC1-CD and Flag-MUC1-CD. At 48 hours post-transfection, cells are incubated with selected compounds. The cells were harvested for immunoblotting with anti-MUC1-C. Total cell lysates are subjected to immunoprecipitation with anti-GFP antibody and the adsorbates are analyzed by immunoblotting with anti-Flag antibody. An inhibitor of MUC1-CD dimerization will inhibit dimerization of MUC1-CD in cyto.

Figure 8:

As a positive control for the validation of this assay, HEK 293 cells were transfected with vectors expressing GFP-MUC1-CD and Flag-MUC1-CD. Complexes of GFP-MUC1-CD and Flag-MUC1-CD were detectable by coprecipitation of lysates from cells not exposed to GO-201 peptide (FIG. 8). However, incubation of the transfected HEK 293 cells with 5 µM GO-201 was associated with the disruption of the interaction between Flag-MUC1-CD and GFP-MUC1-CD (FIG. 8). In addition, a control peptide, CP-1 had no apparent effect. These results indicate that a specific compound that will bind to MUC1-CD and inhibit formation of MUC1-CD oligomerization in cells. Therefore this assay can confirm the advancement of selected compounds.

Assays for Detection of Endogenous MUC1 Expression in Human Breast Carcinoma Cells.

Western Blot Analysis for expression of MUC1 protein. MCF-7 cells were treated with multiple concentrations of the selected compounds daily for 6 days. Total cell lysates were be analysed by immunoblotting with ant-MUC1-C antibody to detect the protein levels.

Luciferase Assay for Transcriptional Inhibition of MUC1.

Figure 9:
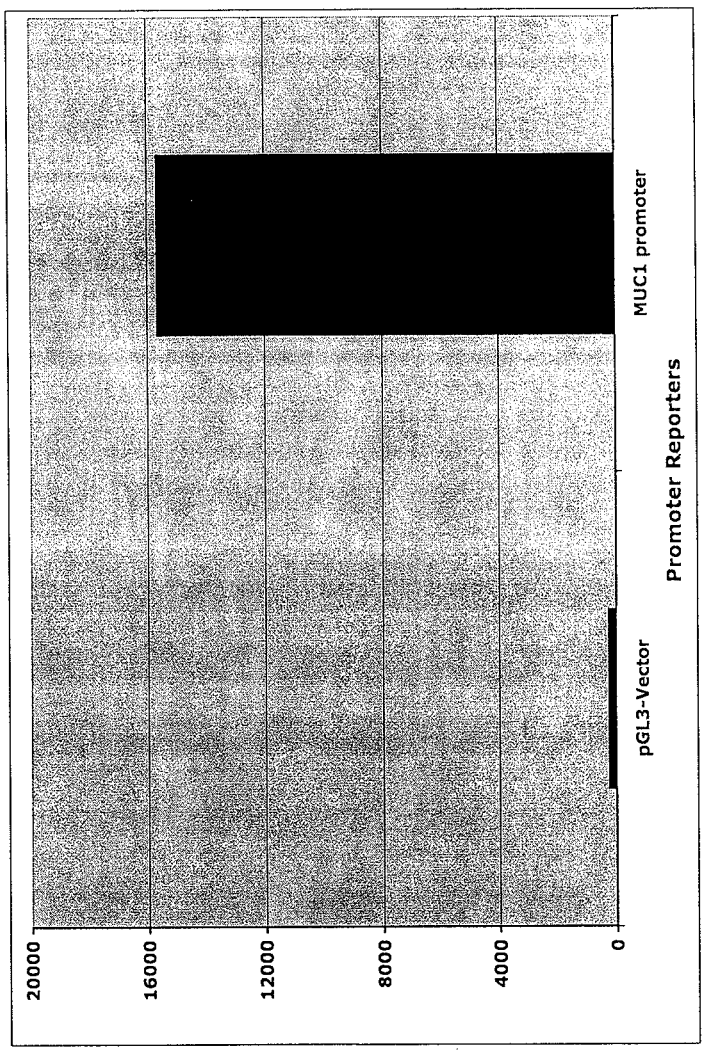
FIG. 9—Stable cell line expressing a detectable marker under the control of the MUC1 promoter. MUC1 gene promoter was introduced in front of luciferase reporter gene in pGL3 cassette and MCF-7 cells were transfected with this construct. A stable cell line was developed by selecting the transfectants with hygromycin. MUC1 promoter activity was measured in the stable cell line by measuring the luminescence from the luciferase expression driven by MUC1 promoter.

The inventors have generated luciferase linked MUC1 promoter in pGL3 vector. As a validation of the assay, luciferase activity from MCF-7 cells with integrated MUC1 or pGL3 vector promoter reporter is shown in FIG. 9. These cells are treated with different concentrations of the selected compounds. Luciferase activity is measured by standard protocol.

Screening for Compounds that Inhibit MUC1-CD Dimerization.

Figure 6:
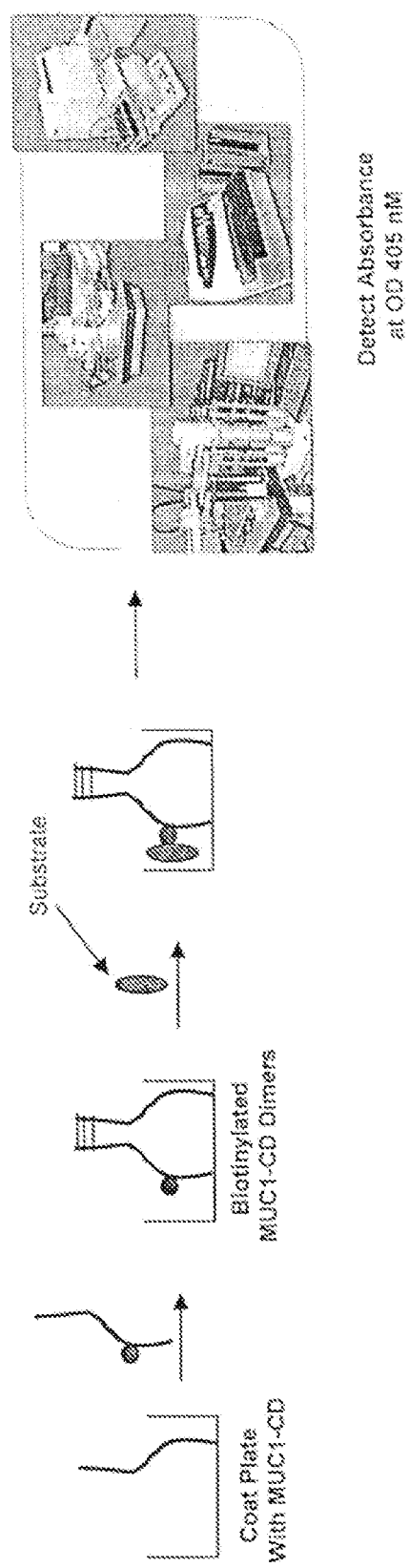
FIG. 6—Schematic Illustration of Primary HTS Screening Assay for MUC1-CD Dimerization. MUC1-CD protein was coated on a 96 well plate and then incubated with Biotinylated MUC1-CD that binds to non-biotinylated MUC1-CD protein by dimer formation. Bound biotinylated MUC1-CD protein was detected by incubation with Streptavin-HRP+peroxidase substrate system. While screening for an inhibitory compound, a positive inhibitor will be the one which yields a substantially lowered signal to that compared with wells incubated with buffer.

As discussed above, MUC1-C cytoplasmic domain (MUC1-CD) contains Cys residues at positions 1 and 3 that are necessary for its dimerization (FIG. 1A) (Kufe, 2009; Leng et al., 2007). To develop an assay for identifying inhibitors of MUC1-CD dimerization, 96-well plates were first coated with purified MUC1-CD (FIG. 6). Biotinylated MUC1-CD was then added to the wells and its interaction with bound MUC1-CD was detected with streptavidin-HRP (FIG. 6). Quantitation of the signals was determined with EnVision.

Figure 17A:
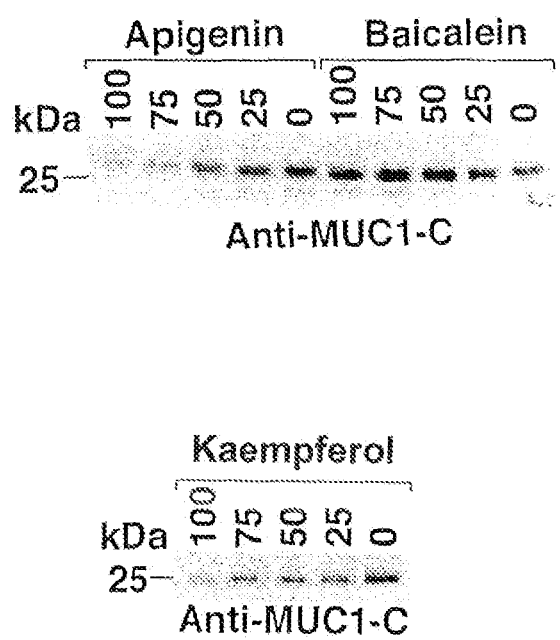
FIGS. 17A-B—Kaempterol inhibiting breast cancer cells. ZR-75-1 breast carcinoma cells were treated with 0-100 mM Kaempterol for 2 days. Total cell lysates were then analyzed by immunoblotting with anti-MUC1-C antibody (FIG. 17A) or with anti-Actin antibodies (FIG. 17B).
Figure 17B:
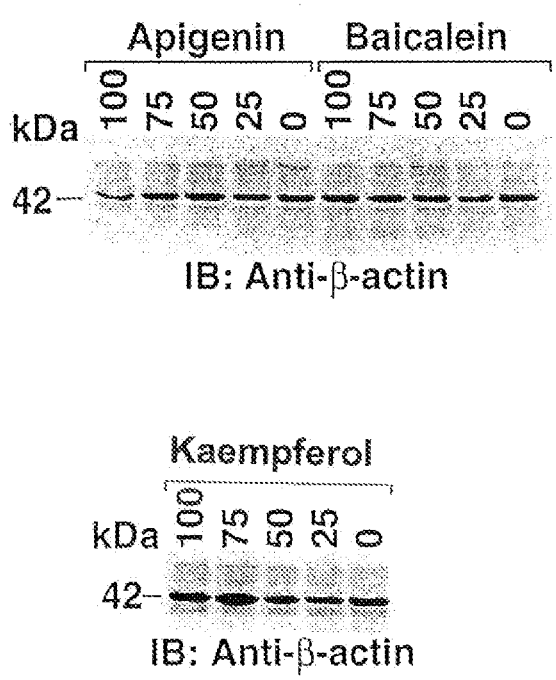

An initial screen of the library shown in Table 1 resulted in the identification of a number of MUC1 dimerization inhibitory compounds from the flavone family, including Morin, Apigenin, Fisetin and PD98059. With this information, the inventors obtained of a flavone-centric library that was screened for inhibition of MUC1 dimer formation. Using this approach, six libraries containing over 5,000 compounds were screened for molecules that block the formation of MUC1-CD dimmers (FIG. 11). Initial screens were performed in the presence of compounds at a concentration of 100 µM. Compounds that inhibited dimerization by greater than 50% were selected as positive hits. Using these criteria, the percentage of positive compounds ranged from ~1% to nearly 4% depending on the library. The seven compounds shown in FIG. 10 further screened against MUC1-expressing cancer cells in vitro. Dose response curves were generated for each of these compounds, with the best showing an $LC_{50}$ of below 2.5 µM. FIGS. 17A-B illustrate this same assay comparing three closely related flavones—Apigenin, Kaempferol and Baicalein. Interestingly, while Apigenin and Kaempferol showed inhibition, Baicalein did not.

Identification of Apigenin as an Inhibitor of MUC1-CD Dimerization.

Based on the screening results, the inventors identified apigenin (4',5,7-trihydroxyflavone) as one candidate inhibitor (FIG. 12A). Compared to vehicle (DMSO), 100 µM apigenin inhibited MUC1-CD dimerization by approximately 80% (FIG. 12A). By contrast, the structurally related baicalein (5,6,7-trihydroxyflavone) had little if any effect (FIG. 12A). Analysis of apigenin over a range of concentrations further demonstrated 50% inhibition ($IC_{50}$) of MUC1-CD dimerization at 76 µM (FIG. 12B). To extend these observations, studies of MUC1-CD dimerization were performed using soluble unbound protein. Previous work showed that the 10 kDa MUC1-CD monomer forms 20 kDa dimers in solution (Raina et al., 2009). As detected by immunoblot analysis, the formation of MUC1-CD dimers was completely blocked by apigenin, whereas baicalein had little effect (FIG. 12C). Transfection of cells with GFP-MUC1-CD and Flag-MUC1-CD has also been used to assess the formation of MUC1-CD dimers in coimmunoprecipitation assays (Raina et al., 2009). In this regard, immunoblot analysis of anti-Flag precipitates with anti-GFP readily detected MUC1-CD dimerization in the absence of treatment (FIG. 12D). Moreover, the formation of MUC1-CD dimers was completely blocked by apigenin, but not baicalein, treatment (FIG. 12D). These findings indicated that apigenin functions as an inhibitor of MUC1-CD dimerization in vitro and in cells.

Effects of Apigenin on MUC1 Expression in MCF-10A Mammary Epithelial Cells.

MUC1-C localizes to the nucleus by a mechanism dependent on its dimerization and thereby promotes induction of the MUC1 gene in an auto-catalytic loop (Leng et al., 2007; Ahmad et al., 2009). Accordingly, studies were performed to assess the effects of apigenin on localization of MUC1-C to the nucleus. Treatment of immortalized MCF-10A mammary epithelial cells with 50 to 100 µM apigenin was associated with downregulation of MUC1-C levels (FIG. 13A). By contrast, baicalein had no apparent effect on expression of the MUC1-C subunit (FIG. 13A). In association with the downregulation of MUC1-C, apigenin decreased MCF-10A cell number, whereas baicalein was substantially less effective (FIG. 13B). MUC1-C protects against the induction of cell death (Ren et al., 2004; Yin and Kufe, 2003; Yin et al., 2007; Yin et al., 2009). In this context, treatment of MCF-10A cells with apigenin, and not baicalein, was also associated with caspase-9 cleavage (FIG. 13C) and loss of cell membrane integrity as determined by PI uptake (FIG. 13D), consistent with the induction of apoptotic cell death.

Apigenin, but not Baicalein, Downregulates MUC1 in MCF-7 Breast Cancer Cells.

In MCF-7 cells, treatment with apigenin was associated with downregulation of MUC1 mRNA levels, whereas baicalein had no apparent effect compared to control (FIG. 14A). In concert with these results, apigenin and not baicalein decreased expression of the MUC1-C protein in the nucleus (FIG. 14B) and in whole cell lysates (FIG. 14C). To assess MUC1-dependent effects of apigenin, the MCF-7 cells were transduced with an empty lentiviral vector or one expressing a MUC1 shRNA that was associated with a substantial decrease in MUC1-C levels (FIG. 14D). Silencing MUC1 partially decreased sensitivity of the MCF-7 cells to apigenin-induced decreases in cell number, consistent in part with a MUC1-dependent effect (FIG. 14E).

Downregulation of MUC1-C expression in MCF-7 cells is associated with loss of viability (Jin et al., 2010). By extension, apigenin treatment was associated with cleavage of caspase-9 (FIG. 15A) and loss of cell membrane integrity (FIG. 15B). To assess the effects on survival, MCF-7 cells were treated with apigenin and then analyzed for colony formation (FIG. 15C). In concert with the loss of cell membrane integrity, treatment with 25 µM apigenin was associated with a substantial decrease in colonies and complete loss of survival at higher concentrations (FIG. 15D).

MUC1-Dependent Effects of Apigenin on Survival of HCC1937 and BT474 Breast Cancer Cells.

Other studies were performed with HCC1937 breast cancer cells that have low to undetectable MUC1-C levels and BT474 breast cancer cells that express MUC1-C at levels comparable to those in MCF-7 cells (FIG. 16A). As found in MCF-7 cells, treatment of BT474 cells with apigenin was associated with downregulation of MUC1-C expression (FIG. 16B). In addition, apigenin treatment of BT474 cells, but not HCC1937 cells, was associated with loss of viability (FIG. 16C). Treatment of BT474 cells was also associated with concentration dependent decreases in clonogenic survival (FIG. 16D). These findings indicated that apigenin downregulates MUC1-C expression in association with apigenin-induced loss of viability.

Example 3

Discussion

MUC1/CQC Peptide Blocks MUC1 Oligomerization.

Overexpression of MUC1 is sufficient for the induction of anchorage-independent growth and tumorigenicity (Li et al., 2003a; Huang et al., 2003; Huang et al., 2005). Notably, however, the MUC1 transforming function is abrogated by mutation of the CQC motif in the cytoplasmic domain to AQA (Leng et al., 2007). MUC1 forms oligomers and the CQC motif is necessary for this oligomerization (Leng et al., 2007). Moreover, oligomer formation is necessary for targeting of the MUC1-C subunit to the nucleus (Leng et al., 2007). Other functions of the MUC1-C subunit, such as activation of the Wnt/β-catenin and IKKβ→NF-κB pathways, are also dependent on the formation of MUC1-C oligomers (unpublished data). Based on these findings, the inventors reasoned that disruption of MUC1 oligomerization by a small molecule would have the potential to block the MUC1 transforming function. In that context, they synthesized a MUC1-derived peptide that contains the CQC motif and a poly-Arg cell delivery domain for entry into cells. Initial studies with this MUC1/CQC peptide showed that it inhibits oligomerization of MUC1-CD in vitro. As shown previously by BIAcore analysis, MUC1-CD forms dimers with a dissociation constant (Kd) of 33 nM (Leng et al., 2007). The MUC1/CQC peptide similarly bound to MUC1-CD with a Kd of 30 nM. In addition, the demonstration that the MUC1/AQA peptide has little if any effect on MUC1 oligomerization provided support for dependence on the CQC motif. MUC1/CQC, and not MUC1/AQA, was also effective in blocking MUC1-CD oligomerization in cells. These findings thus indicated that the MUC1/CQC peptide could be used to disrupt MUC1 oligomerization and potentially thereby MUC1 function in human breast carcinoma cells.

Identification of Small Molecule MUC1-CD Dimerization Inhibitors.

These findings discussed above provided support for the development of a screen to identify small molecule inhibitors of MUC1-C dimerization as an approach to block its oncogenic function. In that line of reasoning, a plate-based assay was developed to screen compounds in selected known bioactives (BIOMOL ICCB3, NINDS2, Prestwick1, Microsource1) and natural product extract (NCDDG8, MMV6) libraries available through the ICCB-Longwood, Harvard Medical School Screening Facility. As scored by over 50% inhibition of MUC1-CD dimerization, the percentage of positive hits was lowest (1%) in the BIOMOL ICCB3 library of known bioactives and highest (>3%) in the MMV6 fungal extract library. The BIOMOL ICCB3 library includes diverse classes of compounds, including ion channel blockers, second messenger modulators, kinase inhibitors, gene regulation agents and other well characterized compounds that disrupt cell pathways. Positive hits were further characterized over a range of concentrations to confirm results in the initial screen and to define an $IC_{50}$. Among other compounds of interest, the inventors selected the naturally-occurring plant flavone, apigenin, as one candidate for further study based in part on its known anti-cancer properties (Shukla and Gupta, 2010). Apigenin has also been widely studied for its anti-inflammatory properties and as a cancer chemopreventive agent. However, to the inventors' knowledge, there has been no evidence for involvement of apigenin in the regulation of MUC1 expression or signaling.

Apigenin Blocks MUC1-C Dimerization and Signaling.

The effects of apigenin on MUC1-CD dimerization observed in the plate-based assay were confirmed using soluble MUC1-CD and in 293 cells expressing Flag and GFP-tagged MUC1-CD. To address the issue of specificity, the inventors compared the inhibition of MUC1-CD dimerization by apigenin with that obtained with the highly related flavone baicalein that also has three hydroxyl groups, but at positions 5, 6 and 7 rather than at 4', 5 and 7 in apigenin. In addition, like apigenin, baicalein has anti-cancer activity (Taniguchi et al., 2008). Surprisingly however, unlike apigenin, baicalein had little if any effect on MUC1-CD dimerization, indicating that positioning of the hydroxyls is of importance for inhibition. Nuclear localization of MUC1-C was also blocked by apigenin, but not baicalein, consistent with the requirement of MUC1-C dimerization for interaction with importin β and import into the nucleus (Leng et al., 2007). Consistent with these results, inhibition of MUC1-C dimerization with a cell-penetrating peptide that blocks the CQC motif in the cytoplasmic domain also decreased localization of MUC1-C to the nucleus (Raina et al., 2009). As noted above, the oncogenic function of MUC1-C relates, at least in part, to its induction of gene signatures that confer tumorigenesis, angiogenesis and extracellular matrix remodeling (Khodarev et al., 2009; Pitroda et al., 2009; MacDermed et al., 2010). Moreover, MUC1-C interacts with NF-κB p65 and STAT1/3 on the MUC1 promoter that, in turn, auto-induces activation of MUC1 expression (Ahmad et al., 2009; Khodarev et al., 2010). In this way, blocking MUC1-C dimerization and nuclear localization with apigenin would be expected to decrease MUC1 expression at the mRNA and protein levels. Indeed, apigenin, and not baicalein, blocked MUC1-C occupancy on the MUC1 promoter and decreased MUC1 transcripts. Apigenin treatment was also associated with downregulation of MUC1-C protein expression. These findings do not exclude the possibility that apigenin, which can affect diverse pathways (Shukla and Gupta, 2010), suppresses MUC1 expression by other mechanisms unrelated to blocking MUC1-C dimerization. Nonetheless, the apigenin-induced inhibition of MUC1-C dimerization and nuclear localization is consistent at least in large part with the observed downregulation of MUC1 expression.

Effects of Blocking MUC1-C Dimerization.

Studies with a cell penetrating peptide drug that binds to the MUC1-C cytoplasmic domain at the CQC motif have demonstrated that blocking MUC1-C dimerization is associated with inhibition of breast cancer cell growth and survival (Ahmad et al., 2009). Moreover, the MUC1-C dimerization peptide inhibitor was ineffective against MUC1-negative carcinoma cells (Joshi et al., 2009), supporting selectivity of this agent. In the present studies, apigenin-induced inhibition of MUC1-C dimerization in MCF-10A mammary epithelial cells was associated with apoptotic cell death. Treatment of MUC1-positive MCF-7 and BT474 breast cancer cells with apigenin was also associated with loss of clonogenic survival, consistent with the effects of the effects of the peptide inhibitor of MUC1-C dimerization. In MCF-7 cells, apigenin has been shown to target ERá-dependent signaling (Long et al., 2008). In this regard, MUC1-C interacts with ERα and promotes ERá-dependent gene expression (Wei et al., 2006). Thus, the inhibitory effects of apigenin on MUC1-C dimerization and nuclear localization could contribute to disruption of ERα signaling. Other studies have reported that apigenin induces apoptosis of breast cancer cells by inhibiting the PI3K→Akt pathway and downregulating ErbB2 expression (Way et al., 2004; Way et al., 2005; Lee et al., 2008). MUC1-C contributes to activation of the PI3K→Akt pathway (Raina et al., 2004) and interacts with the ErbB2 signaling pathway (Yin and Kufe, 2003; Ren et al., 2006). These observations and those in the present work invoke the possibility that apigenin-induced inhibition of MUC1-C dimerization may be responsible, at least in part, for the observed effects of this agent on breast cancer cells. Nonetheless, apigenin has been linked to disruption of diverse pathways in breast and other types of carcinoma cells that are not formally attributable to loss of MUC1-C function. In that line of reasoning, the present finding that apigenin blocks MUC1-C dimerization represents a new mechanism that should be considered when studying the anti-cancer activity of this agent. The present findings also indicate that MUC1-C is a druggable target for the development of small molecule inhibitors of its oncogenic function.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference:

U.S. Pat. No. 5,440,013
U.S. Pat. No. 5,446,128
U.S. Pat. No. 5,475,085
U.S. Pat. No. 5,597,457
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,790,421
U.S. Pat. No. 5,840,833
U.S. Pat. No. 5,859,184
U.S. Pat. No. 5,889,155
U.S. Pat. No. 5,929,237
U.S. Pat. No. 6,093,573
U.S. Pat. No. 6,261,569
U.S. Patent Appln. 2005/0015232
Aaronson and Horvath, *Science*, 296(5573):1653-5, 2002.
Abe and Kufe, *Cancer Res.*, 49(11):2834-2839, 1989.
Agata et al., *Cancer Res.*, 68:6136-44, 2008.
Ahmad et al., *J. Biol. Chem.*, 281:35764-9, 2006.
Ahmad et al., *Nat. Cell Biol.*, 9:1419-1427, 2007.
Ahmad et al., *Cancer Res.*, 68:2920-2926, 2008.
Ahmad et al., *Cancer Res.*, 69:7013-7021, 2009.
Alvarez et al., *Cancer Res.*, 65(12):5054-62, 2005.
Alvarez et al., *Cancer Res.*, 66(6):3162-8, 2006.
Baldus et al., *Clin. Cancer Res.*, 10(8):2790-2796, 2004.

Bodanszky et al., *J. Antibiot.*, 29(5):549-53, 1976.
Bowman et al., *Oncogene*, 19(21):2474-88, 2000.
Bromberg et al., *Cell*, 98(3):295-303, 1999.
Buerger et al., *J. Biol. Chem.*, 278(39):37610-21, 2003.
Chen and Greene, *Mol. Cell. Biol.* 5:392-401, 2004.
Cohen et al., *J. Med. Chem.*, 33:883-894, 1990.
Duraisamy et al., *Gene*, 373:28-34, 2006.
Fischer, *Med. Res. Rev.*, 27(6):755-796, 2007.
Gaemers et al., *J. Biol. Chem.*, 276:6191-6199, 2001.
Gendler et al., *J. Biol. Chem.*, 263:12820-12823, 1988.
Germain and Frank, *Clin. Cancer Res.*, 13(19):5665-9, 2007.
Gerondakis et al., *Oncogene* 25(51):6781-99, 2006.
Ghosh et al., *Annu. Rev. Cell. Dev. Biol.*, 16:225-60, 1998.
Gilmore, available from NF-kB.org, 2008.
Grillot et al., *J. Immunol.*, 158:4750-7, 1997.
Gronenborn et al., *Anal. Chem.*, 62(1):2-15, 1990.
Hayden and Ghosh, *Cell*, 132:344-62, 2008.
Hodel et al., *Mol. Cell*, 10(2):347-58, 2002.
Hoffman et al., *Oncogene*, 25:6706-16, 2006.
Huang et al., *Cancer Biol Ther.*, 2:702-706, 2003.
Huang et al., *Cancer Res.*, 65:10413-10422, 2005.
Huxford et al., *Cell* 95(6):759-70, 1998.
Jackson, *Seminars in Oncology*, 24:L164-172, 1997.
Jacobs et al., *Cell*, 95:749-58, 1998.
Jin et al., *Int. J. Oncol.*, 37:61-69, 2010.
Johnson et al., In: *Biotechnology And Pharmacy*, Pezzuto et al. (Eds.), Chapman and Hall, NY, 1993.
Jones et al., *J. Med. Chem.*, 39:904-917, 1996.
Joshi et al., *Mol. Cancer. Ther.*, 8:3056-3065, 2009.
Karin and Lin, *Nat. Immunol.*, 3:221-7, 2002.
Kau et al., *Nat. Rev. Cancer*, 4(2):106-17, 2004.
Kawano et al., *Cancer Res.*, 67:11576-84, 2007.
Khodarev et al., *Cancer Res.*, 69:2833-2837, 2009.
Khodarev et al., *Oncogene*, 29:920-9, 2010.
Kinlough et al., *J. Biol. Chem.*, 279(51):53071-53077, 2004.
Kufe et al., *Hybridoma*, 3:223-232, 1984.
Kufe, *Nature Rev. Cancer*, 9:874-85, 2009.
Lagow and Carson, *J. Cell. Biochem.*, 86:759-72, 2002.
Lee et al., *Cancer Cell*, 15(4):283-293, 2009.
Lee et al., *Toxicol. Appl. Pharmacol.*, 226:178-191, 2008.
Leng et al., *J. Biol. Chem.*, 282:19321-19330, 2007.
Levitan et al., *J. Biol. Chem.*, 280:33374-33386, 2005.
Li et al., *Oncogene*, 22:6107-6110, 2003a.
Li et al., *Cancer Biol. Ther.*, 2:187-193, 2003b.
Li et al., *Mol. Cancer. Res.*, 1:765-775, 2003c.
Li et al., *J. Biol. Chem.*, 276:35239-35242, 2001.
Li et al., *J. Biol. Chem.*, 276:6061-6064, 2001.
Li et al., *Mol. Cell. Biol.*, 18:7216-7224, 1998.
Ligtenberg et al., *J. Biol. Chem.*, 267, 6171-6177, 1992.
Long et al., *Mol. Cancer. Ther.*, 7:2096-2108, 2008.
Macao, *Nat. Struct. Mol. Biol.*, 13, 71-76, 2006.
MacDermed et al., *BMC Med. Genomics*, 3:16, 2010.
McPherson, *J. Biol. Chem.*, 251:6300-6306, 1976.
Merlo et al., *Cancer Res.*, 49, 6966-6971, 1989.
Merrifield, *J. Am. Chem. Soc.*, 85:2149-2154, 1963.
Micheau & Tschopp, *Cell*, 114:181-90, 2003.
Muthuswamy, *Nat. Cell Biol.*, 3(9):785-92, 2001.
Natoli et al., *Nat. Immunol.*, 6:439-45, 2005.
Navia et al., *Curr. Opin. Struct. Biol.*, 2:202-210, 1992.
Pasparakis et al., *Cell Death Differ.* 13:861-72, 2006.
Patel et al., *Int. J Oncol.*, 30:233-245, 2007.
PCT Appln. PCT/US00/03745
PCT Appln. PCT/US00/14667
PCT Appln. PCT/US99/11913
PCT Appln. PCT/US99/18441 Peptide Synthesis, 1985
Percipalle et al., *J. Mol. Biol.*, (4):722-32, 1997.
Perey et al., *Cancer Res.*, 52(22):6365-6370, 1992.
Pitroda et al., *Proc. Natl. Acad. Sci. USA*, 106:5837-5841, 2009.
Protective Groups in Organic Chemistry, 1973
Protein NMR Spectroscopy, Principles and Practice, J. Cavanagh et al., Academic Press, San Diego, 1996.
Raina et al., *Cancer Res.*, 69:5133-5141, 2009.
Raina et al., *Direct targeting of the MUC1 oncoprotein blocks survival and tumorigenicity of human breast carcinoma cells*. Cancer Res., 2009 (IN PRESS).
Raina et al., *EMBO J.*, 25:3774-3783, 2006.
Raina et al., *J. Biol. Chem.*, 279:20607-20612, 2004.
Ramasamy et al., *Mol. Cell*, 27:992-1004, 2007.
Remington's Pharmaceutical Sciences, 15$^{th}$ Ed., 1035-1038 and 1570-1580, 1990.
Remington's Pharmaceutical Sciences, 15$^{th}$ Ed., 3:624-652, 1990.
Ren et al., *Cancer Cell*, 5:163-175, 2004.
Ren et al., *J. Biol. Chem.*, 277:17616-17622, 2002.
Ren et al., *Oncogene*, 25:20-31, 2006.
Ryan and Wente, *Curr. Opin. Cell Biol.*, 12(3):361-71, 2000.
Sarda et al., In: *A facile synthesis of flavones using recyclable ionic liquid under microwave irradiation*, Arkivoc xvi:43-48, 2006.
Schneider-Brachert et al., *Immunity*, 21:415-28, 2004.
Schroeder et al., *J. Biol. Chem.*, 276(16):13057-13064, 2001.
Schroeder et al., *Oncogene*, 23:5739-5747, 2004.
Shuai, *Oncogene*, 19(21):2638-44, 2000.
Shukla and Gupta, *Pharm. Res.*, 27:962-978, 2010.
Siddiquee et al., *Proc. Natl. Acad. Sci. USA*, 104(18):7391-6, 2007.
Siddiqui et al., *Proc. Natl. Acad. Sci. USA*, 85:2320-2323, 1988.
Solid Phase Peptide Synthelia, 1984
Song et al., *Proc. Natl. Acad. Sci. USA*, 102(13):4700-5, 2005.
Soule et al., *Cancer Res.*, 50(18):6075-6086, 1990.
Suh and Gumbiner, *Exp. Cell Res.*, 290(2):447-56, 2003.
Taniguchi et al., *Cancer Res.*, 68:8918-8927, 2008.
Truscott et al., *J Cell Biol.*, 163(4):707-713, 2003.
Vermeer et al., *Nature*, 422(6929):322-6, 2003.
Way et al., *FEBS Lett.*, 579:145-152, 2005.
Way et al., *J. Biol. Chem.*, 279:4479-4489, 2004.
Weber, *Advances Protein Chem.*, 41:1-36, 1991.
Wegenka et al., *Mol. Cell. Biol.*, 14(5):3186-96, 1994.
Wei et al., *Cancer Cell*, 7:167-178, 2005.
Wei et al., *Cancer Res.*, 67(4):1853-8, 2007.
Wei et al., *Mol. Cell*, 21:295-305, 2006.
Weis, *Cell*, 112(4):441-51, 2003.
Wen et al., *J. Biol. Chem.*, 278:38029-38039, 2003.
Wessely and Moser, *Monatsh. Chem.* 56 (1):97-105, 1930.
Wider, *BioTechniques*, 29:1278-1294, 2000.
Yamamoto et al., *J. Biol. Chem.*, 272:12492-12494, 1997.
Yin et al., *Int. J. Oncol.*, 34:1691-1699, 2009.
Yin et al., *J. Biol. Chem.*, 278:35458-35464, 2003.
Yin et al., *J. Biol. Chem.*, 279:45721-45727, 2004.
Yin et al., *J. Biol. Chem.*, 282:257-266, 2007.
Young et al., *Cell.* 112(1):41-50, 2003.
Yu and Jove, *Nat. Rev. Cancer*, 4(2):97-105, 2004.
Zhang et al., *Mol. Cell. Biol.*, 19:7138-7146, 1999.

What is claimed is:

1. A method of inhibiting inflammatory signaling in a cancer cell comprising:
   (a) assessing MUC1 overexpression in said cancer cell, and;
   (h) further contacting said cancer cell with a flavone having the structure of:

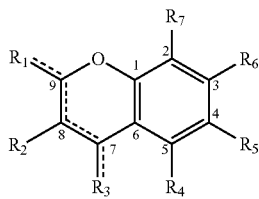

or a salt thereof, wherein
$R_1$ is H, —OH, =O, substituted or unsubstituted alkyl ($C_{1-8}$), alkoxy($C_{1-8}$), haloalkyl($C_{1-8}$), substituted phenyl or unsubstituted phenyl, wherein if $R_1$ is =O, $C_7$-$C_8$ is a double bond;
$R_2$ is H, —OH, alkyl($C_{1-8}$), substituted phenyl, unsubstituted phenyl, phenyl, phenyl thiazole, imidazole, pyrazole or furan;
$R_3$ is H, —OH, =O, halogen, haloalkyl($C_{1-8}$), substituted or unsubstituted alkyl($C_{1-8}$), substituted phenyl or unsubstituted phenyl, wherein if $R_3$ is =O, $C_8$-$C_9$ is a double bond;
$R_4$ is H or —OH;
$R_5$ is H, —OH, substituted or unsubstituted alkyl($C_{1-8}$) or alkoxy($C_{1-8}$), or $OR_8$, wherein $R_8$ is alkyl($C_{1-8}$), an ester or an amide;
$R_6$ is H, —OH substituted or unsubstituted alkyl($C_{1-8}$) or alkoxy($C_{1-8}$), or $OR_8$, wherein $R_8$ is alkyl($C_{1-8}$), an ester or an amide; and
$R_7$ is H, —OH, or substituted or unsubstituted alkyl($C_{1-8}$), with the proviso that $R_1$ and $R_3$ cannot both be =O.

2. The method of claim 1, wherein said flavone in Morin or a salt thereof.

3. The method of claim 1, wherein said flavone is Apigenin or Kaempterol or a salt thereof.

4. The method of claim 1, wherein said flavone in Fisetin or a salt thereof.

5. The method of claim 1, wherein said flavone in PD98059 or a salt thereof.

6. The method of claim 1, wherein said flavone is 7-(benzyloxy)-4-(trifluoromethyl)-2H-chromen-2-one.

7. The method of claim 1, wherein said flavone is 7-[(3-oxobutan-2-yl)oxy]-4-phenyl-2H-chromen-2-one.

8. The method of claim 1, wherein said $R_1$ is =O.

9. The method of claim 1, wherein said $R_3$ is =O.

10. The method of claim 1, wherein the cancer cell is a solid tumor cell.

11. The method of claim 10, wherein the solid tumor cell is a lung cancer cell, a brain cancer cell, a head & neck cancer cell, a breast cancer cell, a skin cancer cell, a liver cancer cell, a pancreatic cancer cell, a stomach cancer cell, a colon cancer cell, a rectal cancer cell, a uterine cancer cell, a cervical cancer cell, an ovarian cancer cell, a testicular cancer cell, a skin cancer cell or a esophageal cancer cell.

12. The method of claim 1, wherein the MUC1 positive cancer cell is a leukemia or myeloma cell.

13. The method of claim 12, wherein the MUC-1 positive cancer cell is an acute myeloid leukemia, chronic myelogenous leukemia or multiple myeloma.

14. The method of claim 1, wherein the cancer cell is located in a subject.

15. The method of claim 14, wherein said subject is a human subject.

16. The method of claim 14, further comprising administering to said subject a second cancer therapy.

17. The method of claim 16, wherein said second cancer therapy is chemotherapy, radiotherapy, immunotherapy, toxin therapy, hormone therapy, gene therapy or surgery.

18. The method of claim 16, wherein said second therapy is given at the same time as said flavone.

19. The method of claim 16, wherein said second therapy is given before or after said flavone.

20. The method of claim 1, further comprising contacting said cell with a second anti-inflammatory agent.

21. The method of claim 20, wherein said second anti-inflammatory agent is contacted prior to or after said compound.

22. The method of claim 20, wherein said second anti-inflammatory agent is contacted at the same time as said compound.

* * * * *

UNITED STATES PATENT AND TRADEMARK OFFICE
CERTIFICATE OF CORRECTION

PATENT NO.        : 8,952,054 B2               Page 1 of 1
APPLICATION NO.   : 13/045033
DATED             : February 10, 2015
INVENTOR(S)       : Kufe et al.

It is certified that error appears in the above-identified patent and that said Letters Patent is hereby corrected as shown below:

In the claims

Claim 1, column 63, line 26, delete "(h)" and insert --(b)-- therefor.

Claim 12, column 64, line 38, delete "MUC1 positive".

Claim 13, column 64, line 40, delete "MUC-1 positive".

Signed and Sealed this
Fifth Day of May, 2015

Michelle K. Lee
*Director of the United States Patent and Trademark Office*

SEQUENCE LISTING

<160> NUMBER OF SEQ ID NOS: 11

<210> SEQ ID NO 1
<211> LENGTH: 72
<212> TYPE: PRT
<213> ORGANISM: Homo sapiens

<400> SEQUENCE: 1

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Ser Tyr Thr Asn Pro Ala
50                  55                  60

Val Ala Ala Thr Ser Ala Asn Leu
65                  70

<210> SEQ ID NO 2
<211> LENGTH: 159
<212> TYPE: PRT
<213> ORGANISM: Homo sapiens

<400> SEQUENCE: 2

Gly Ser Val Val Val Gln Leu Thr Leu Ala Phe Arg Glu Gly Thr Ile
1               5                   10                  15

Asn Val His Asp Val Glu Thr Gln Phe Asn Gln Tyr Lys Thr Glu Ala
            20                  25                  30

Ala Ser Arg Tyr Asn Leu Thr Ile Ser Asp Val Ser Val Ser Asp Val
        35                  40                  45

Pro Phe Pro Phe Ser Ala Gln Ser Gly Ala Gly Val Pro Gly Trp Gly
    50                  55                  60

Ile Ala Leu Leu Val Leu Val Cys Val Leu Val Ala Leu Ala Ile Val
65                  70                  75                  80

Tyr Leu Ile Ala Leu Ala Val Cys Gln Cys Arg Arg Lys Asn Tyr Gly
            85                  90                  95

Gln Leu Asp Ile Phe Pro Ala Arg Asp Thr Tyr His Pro Met Ser Glu
        100                 105                 110

Tyr Pro Thr Tyr His Thr His Gly Arg Tyr Val Pro Pro Ser Ser Thr
    115                 120                 125

Asp Arg Ser Pro Tyr Glu Lys Val Ser Ala Gly Asn Gly Gly Ser Ser
130                 135                 140

Leu Ser Tyr Thr Asn Pro Ala Val Ala Ala Thr Ser Ala Asn Leu
145                 150                 155

<210> SEQ ID NO 3
<211> LENGTH: 15
<212> TYPE: PRT
<213> ORGANISM: Homo sapiens

<400> SEQUENCE: 3

Cys Gln Cys Arg Arg Lys Asn Tyr Gly Gln Leu Asp Ile Phe Pro
1               5                   10                  15

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Cys Gln Cys Arg
1

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Cys Gln Cys Arg Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Cys Gln Cys Arg Arg Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Cys Gln Cys Arg Arg Arg Arg
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Cys Gln Cys Arg Arg Lys
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Cys Gln Cys Arg Arg Lys Asn
1               5

<210> SEQ ID NO 10
<211> LENGTH: 15
<212> TYPE: PRT
<213> ORGANISM: Artificial
<220> FEATURE:

```
<223> OTHER INFORMATION: Synthetic peptide

<400> SEQUENCE: 10

Cys Gln Cys Arg Arg Lys Asn Tyr Gly Gln Leu Asp Ile Phe Pro
1               5                   10                  15

<210> SEQ ID NO 11
<211> LENGTH: 15
<212> TYPE: PRT
<213> ORGANISM: Artificial
<220> FEATURE:
<223> OTHER INFORMATION: Synthetic peptide

<400> SEQUENCE: 11

Ala Gln Ala Arg Arg Lys Asn Tyr Gly Gln Leu Asp Ile Phe Pro
1               5                   10                  15
```